US010555950B2

(12) United States Patent
Young et al.

(10) Patent No.: US 10,555,950 B2
(45) Date of Patent: Feb. 11, 2020

(54) BILE ACID RECYCLING INHIBITORS FOR TREATMENT OF OBESITY AND DIABETES

(71) Applicant: Satiogen Pharmaceuticals, Inc., San Diego, CA (US)

(72) Inventors: Andrew A. Young, Chapel Hill, NC (US); Bronislava Gedulin, Del Mar, CA (US); Howard E. Greene, Frankfort, MI (US)

(73) Assignee: SATIOGEN PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 15/097,203

(22) Filed: Apr. 12, 2016

(65) Prior Publication Data

US 2016/0220577 A1 Aug. 4, 2016

Related U.S. Application Data

(63) Continuation of application No. 12/623,977, filed on Nov. 23, 2009, now Pat. No. 9,339,480.

(60) Provisional application No. 61/255,205, filed on Oct. 27, 2009, provisional application No. 61/239,636, filed on Sep. 3, 2009, provisional application No. 61/239,657, filed on Sep. 3, 2009, provisional application No. 61/239,663, filed on Sep. 3, 2009, provisional application No. 61/118,356, filed on Nov. 26, 2008.

(51) Int. Cl.

| | |
|---|---|
| *A61K 31/5377* | (2006.01) |
| *A61K 31/155* | (2006.01) |
| *A61K 31/16* | (2006.01) |
| *A61K 31/40* | (2006.01) |
| *A61K 31/452* | (2006.01) |
| *A61K 31/454* | (2006.01) |
| *A61K 31/495* | (2006.01) |
| *A61K 31/554* | (2006.01) |
| *A61K 9/00* | (2006.01) |
| *A61K 9/48* | (2006.01) |
| *A61K 31/4985* | (2006.01) |
| *A61K 31/4995* | (2006.01) |

(52) U.S. Cl.

CPC ........ *A61K 31/5377* (2013.01); *A61K 9/0053* (2013.01); *A61K 9/485* (2013.01); *A61K 9/4808* (2013.01); *A61K 9/4825* (2013.01); *A61K 9/4858* (2013.01); *A61K 9/4866* (2013.01); *A61K 31/155* (2013.01); *A61K 31/16* (2013.01); *A61K 31/40* (2013.01); *A61K 31/452* (2013.01); *A61K 31/454* (2013.01); *A61K 31/495* (2013.01); *A61K 31/4985* (2013.01); *A61K 31/4995* (2013.01); *A61K 31/554* (2013.01)

(58) Field of Classification Search
USPC ........................................................ 514/183
See application file for complete search history.

(56) References Cited

U.S. PATENT DOCUMENTS

| | | |
|---|---|---|
| 5,234,697 A | 8/1993 | Sipos |
| 5,415,872 A | 5/1995 | Sipos |
| 5,589,358 A | 12/1996 | Dawson |
| 5,663,165 A | 9/1997 | Brieaddy |
| 5,723,458 A | 3/1998 | Brieaddy et al. |
| 5,817,652 A | 10/1998 | Brieaddy et al. |
| 5,900,233 A | 5/1999 | Day |
| 5,908,830 A | 6/1999 | Smith et al. |
| 5,910,494 A | 6/1999 | Brieaddy |
| 5,994,391 A | 11/1999 | Lee et al. |
| 5,998,400 A | 12/1999 | Brieaddy et al. |
| 6,020,330 A | 2/2000 | Enhsen et al. |
| 6,107,494 A | 8/2000 | Lee et al. |
| 6,114,322 A | 9/2000 | Enhsen et al. |
| 6,268,392 B1 | 7/2001 | Keller et al. |
| 6,303,661 B1 | 10/2001 | Demuth et al. |
| 6,309,663 B1 | 10/2001 | Patel et al. |
| 6,329,405 B1 | 12/2001 | Kurata et al. |
| 6,387,924 B2 | 5/2002 | Lee et al. |
| 6,420,417 B1 | 7/2002 | Keller et al. |
| 6,458,851 B1 | 10/2002 | Keller et al. |
| 6,465,451 B1 | 10/2002 | Handlon |
| 6,642,268 B2 | 11/2003 | Keller et al. |
| 6,740,663 B2 | 5/2004 | Tremont et al. |
| 6,784,201 B2 | 8/2004 | Lee et al. |
| 6,852,753 B2 | 2/2005 | Koeller et al. |
| 6,861,053 B1 | 3/2005 | Lin et al. |
| 6,875,877 B2 | 4/2005 | Li et al. |
| 6,890,898 B2 | 5/2005 | Bachovchin et al. |
| 6,906,058 B2 | 6/2005 | Starke et al. |
| 6,943,189 B2 | 9/2005 | Keller et al. |
| 7,125,864 B2 | 10/2006 | Starke et al. |
| 7,132,416 B2 | 11/2006 | Starke et al. |
| 7,179,792 B2 | 2/2007 | Glombik et al. |

(Continued)

FOREIGN PATENT DOCUMENTS

| | | |
|---|---|---|
| CN | 1284953 A | 2/2001 |
| CN | 1439638 A | 9/2003 |

(Continued)

OTHER PUBLICATIONS

Kramer et. al. (Current medicinal Chemistry (2006) 13:997-1016).*
Tremont et. al. (Journal of Medicinal Chemistry (2005) 48:5837-5852).*
Huang et. al. (Journal of Medicinal Chemistry (2005) 48:5853-5868).*
J. G. Cannon, Chapter Nineteen in Burger's Medicinal Chemistry and Drug Discovery, Fifth Edition, vol. I: Principles and Practice, Wiley-Interscience 1995, pp. 783-802. (Year: 1995).*
: Kramer et. al. (Current medicinal Chemistry (2006) 13:997-1016). (Year: 2006).*
Tremont et. al. (Journal of Medicinal Chemistry (2005) 48:5837-5852). (Year: 2005).*

(Continued)

*Primary Examiner* — Marcos L Sznaidman
(74) *Attorney, Agent, or Firm* — Wilson Sonsini Goodrich & Rosati

(57) ABSTRACT

Provided herein are methods of utilizing bile acid transport inhibitors for the treatment of obesity and diabetes.

6 Claims, 10 Drawing Sheets

(56) References Cited

U.S. PATENT DOCUMENTS

| | | | |
|---|---|---|---|
| 7,192,945 | B2 | 3/2007 | Starke et al. |
| 7,192,946 | B2 | 3/2007 | Starke et al. |
| 7,226,943 | B2 | 6/2007 | Starke et al. |
| 7,238,684 | B2 | 7/2007 | Starke et al. |
| 7,514,421 | B2 | 4/2009 | Abrahamsson et al. |
| 7,956,085 | B2 | 6/2011 | Frick et al. |
| 8,106,023 | B2 | 1/2012 | Glombik et al. |
| 8,106,026 | B2 | 1/2012 | Nabel et al. |
| 9,339,480 | B2 | 5/2016 | Young et al. |
| 9,345,715 | B2 | 5/2016 | Young et al. |
| 2003/0139434 | A1 | 7/2003 | Balkan et al. |
| 2003/0149010 | A1 | 8/2003 | Keller et al. |
| 2003/0199482 | A1 | 10/2003 | Seibert et al. |
| 2003/0219472 | A1 | 11/2003 | Pauletti et al. |
| 2004/0014806 | A1 | 1/2004 | Bhat et al. |
| 2004/0122033 | A1 | 6/2004 | Nargund et al. |
| 2004/0138145 | A1 | 7/2004 | Canton et al. |
| 2004/0176438 | A1 | 9/2004 | Tremont et al. |
| 2005/0009805 | A1 | 1/2005 | Sasahara et al. |
| 2005/0124557 | A1 | 6/2005 | Lindqvist |
| 2005/0131068 | A1* | 6/2005 | Alstermark ............ A61K 31/16 514/563 |
| 2006/0094884 | A1 | 5/2006 | Starke et al. |
| 2006/0193895 | A1 | 8/2006 | Miura |
| 2006/0269510 | A1 | 11/2006 | Barbier et al. |
| 2007/0025953 | A1 | 2/2007 | Jones |
| 2007/0032420 | A1 | 2/2007 | Polidori et al. |
| 2007/0190041 | A1 | 8/2007 | Sasahara et al. |
| 2008/0031968 | A1 | 2/2008 | Bianco et al. |
| 2008/0065136 | A1 | 3/2008 | Young |
| 2008/0096921 | A1 | 4/2008 | Navas, III et al. |
| 2008/0145453 | A1 | 6/2008 | Lopez et al. |
| 2008/0167356 | A1 | 7/2008 | Caldwell et al. |
| 2008/0221161 | A1 | 9/2008 | Pinkerton et al. |
| 2009/0118201 | A1 | 5/2009 | Chen et al. |
| 2010/0130426 | A1 | 5/2010 | Young et al. |
| 2011/0065676 | A1 | 3/2011 | Perelman et al. |
| 2011/0294767 | A1 | 12/2011 | Gedulin et al. |
| 2012/0157399 | A1 | 6/2012 | Young et al. |
| 2013/0059807 | A1 | 3/2013 | Gedulin et al. |
| 2015/0087642 | A1 | 3/2015 | Gedulin et al. |

FOREIGN PATENT DOCUMENTS

| | | |
|---|---|---|
| EP | 0509335 A1 | 10/1992 |
| EP | 1273659 A1 | 1/2003 |
| EP | 1347052 A1 | 9/2003 |
| EP | 1173205 B1 | 6/2005 |
| EP | 1535913 A1 | 6/2005 |
| GB | 2465677 A | 6/2010 |
| JP | S6396138 A | 4/1988 |
| JP | 2000026300 A | 1/2000 |
| JP | 2002542208 A | 12/2002 |
| JP | 2005097216 A | 4/2005 |
| JP | 2008517921 A | 5/2008 |
| JP | 2008534523 A | 8/2008 |
| KR | 970005178 B1 | 4/1997 |
| WO | WO-9733882 A1 | 9/1997 |
| WO | WO-9838182 A1 | 9/1998 |
| WO | WO 00/01687 * | 1/2000 |
| WO | WO-0001687 A1 | 1/2000 |
| WO | WO-0062810 A1 | 10/2000 |
| WO | WO-0208211 A2 | 1/2002 |
| WO | WO-02078626 A2 | 10/2002 |
| WO | WO-03018024 A1 | 3/2003 |
| WO | WO-2004020421 A1 | 3/2004 |
| WO | WO-2006031931 A2 | 3/2006 |
| WO | WO-2006057637 A1 | 6/2006 |
| WO | WO-2006105912 A2 | 10/2006 |
| WO | WO-2006105913 A1 | 10/2006 |
| WO | WO-2006116814 A1 | 11/2006 |
| WO | WO-2007041368 A2 | 4/2007 |
| WO | WO-2007095174 A2 | 8/2007 |
| WO | WO-2007127505 A2 | 11/2007 |
| WO | WO-2008002573 A2 | 1/2008 |
| WO | WO-2008058628 A1 | 5/2008 |
| WO | WO-2008058631 A1 | 5/2008 |
| WO | WO-2008067219 A2 | 6/2008 |
| WO | WO-2008091540 A2 | 7/2008 |
| WO | WO-2010059853 A1 | 5/2010 |
| WO | WO-2010062861 A2 | 6/2010 |
| WO | WO-2012064266 A1 | 5/2012 |
| WO | WO-2012064267 A1 | 5/2012 |
| WO | WO-2012064268 A1 | 5/2012 |

OTHER PUBLICATIONS

Huang et. al. (Journal of Medicinal Chemistry (2005) 48:5853-5868). (Year: 2005).*
Adrian et al. Deoxycholate is an important releaser of peptide YY and enteroglucagon from the human colon. Gut 34:1219-1224 (1993).
Anand et al. Role of metformin in experimentally-induced inflammatory bowel disease. ARS Pharmaceutica 49(4):267-281. Database Accession No. EMB-2009271947 (2008) Abstract.
Balas et al. The Dipeptidyl Peptidase IV Inhibitor Vildagliptin Suppresses Endogenous Glucose Production and Enhances Islet Function after Single-Dose Administration in Type 2 Diabetic Patients. The Journal of Clinical Endocrinology & Metabolism 92(4):1249-1255 (2007).
Bhat et al. Inhibition of ileal bile acid transport and reduced atherosclerosis in apoE-/- mice by SC-435. J Lipid Res 44(9):1614-2161 (2003).
Brinton. Novel pathways for glycaemic control in type 2 diabetes: focus on bile acid modulation. Diabetes, Obesity and Metabolism 10(11):1004-1011 (May 2008).
Cannon. Chapter Nineteen in Burger's Medicinal Chemistry and Drug Discovery, Fifth Edition, vol. 1: Principles and Practice, Wiley-Interscience 1995, pp. 783-802.
Chen et al. Liver receptor homologue-1 mediates species- and cell line-specific bile acid-dependent negative feedback regulation of the apical sodium-dependent bile acid transporter. J Biol Chem 278:19909-19916 (2003).
Crosignani et al. Clinical pharmacokinetics of therapeutic bile acids. Clin. Pharmacokinet. 30:333-358 (1996).
Deacon. Dipeptidyl peptidase 4 inhibition with sitagliptin: a new therapy for type 2 diabetes. Expert Opin Investig Drugs 16:533-545 (2007).
Definition of 'conceivable,' from the Free Dictionary, [online] 2009 [Retrieved on Jul. 30, 2012] Retrieved from the internet: http://www.thefreedictionary.com/conceivable.
Dowling et al. Biliary Lipid Secretion and Bile Composition after Acute and Chronic Interruption of the Enterohepatic Circulation in the Rhesus Monkey IV. Primate Biliary Physiology. J. Clin Invest 50:1917-1926 (1971).
Dowling et al. Effects of controlled interruption of the enterohepatic circulation of bile salts by biliary diversion and by ileal resection on bile salt secretion, synthesis, and pool size in the rhesus monkey. J Clin Invest 49:232-242 (1970).
Dumoulin et al. Peptide YY, Glucagon-Like Peptide-1, and Neurotensin Responses to Luminal Factors in the Isolated Vascularly Perfused Rat Ileum. Endocrinology 139(9):3780-3786 (1998).
Edney et al. Cholesterol Drugs Have 'Small' Increased Diabetes Risk, U.S. FDA Says. Bloomberg [online] Feb. 28, 2012 [Retrieved on Jul. 30, 2012] Retrieved from the internet: http://www.bloomberg.com/news/2012-02-28/cholesterol-drugs-have-small-increased-diabetes-risk-u-s-fda-says.html.
El-Shattawy et al. Effectiveness of rectal insulin suppositories containing sodium cholate in normal and insulin dependent diabetic subjects. Pharmaceutical Res 8:S157 (1991).
Enhsen et al. Bile acids in drug discovery. Drug Discover Today 3(9):409-418 (1998).
Genet et al. Structure-Activity Relationship Study of Betulinic Acid, A Novel and Selective TGR5 Agonist, and Its Synthetic Derivatives: Potential Impact in Diabetes. J. Med. Chem. 53:178-190 (2010).

(56) References Cited

OTHER PUBLICATIONS

Geyer et al. The solute carrier family SLC10: More than a family of bile acid transporters regarding function and phylogenetic relationships. Naunyn-Schmiedeberg's Archives of Pharmacology 372(6):413-431 (2006).
Green et al. Inhibition of dipeptidylpeptidase IV activity as a therapy of type 2 diabetes. Expert Opin Emerg Drugs 11(3):525-539 (2006).
Holquist et al. FDA safety page: Delayed-release vs. extended release Rxs. Drug Topics [online] Jul. 23, 2007 [Retrieved on Jul. 30, 2012] Retrieved from the internet: http://drugtopics.modernmedicine.com/drugtopics/Top+News/FDA-safety-page-Delayed-release-vs-extended-release/ArticleStandard/Article/detail/442606.
Hosny et al. Effect of different bile salts on the relative hypoglycemia of witepsol W35 suppositories containing insulin in diabetic beale dogs. Drug. Dev. Ind. Pharm. 27:837-845 (2001).
Hosny et al. Evaluation of efficiency of insulin suppository formulations containing sodium salicylate or sodium cholate in insulin dependent diabetic patients. Bollettino Chiico Farmceutico 142:361-366 (2003).
Hosny et al. Relative hypoglycemia of rectal insulin suppositories containing deoxycholic acid, sodium taurocholate, polycarbophil and their combinations in diabetic rabbits. Drug Dev. Ind. Pharm. 25:745-752 (1999).
Huang et al. Discovery of potent, nonsystemic apical sodium-codependent bile acid transporter inhibitors (Part 2). J Med Chem 48(18):5853-68 (2005).
Huang et al. Discovery of potent, nonsytemic apical sodium-codependent bile acid transporter inhibitors (Part 1). J Med Chem 48(18):5837-5852 (2005).
Katsuma et al. Bile acids promote glucagon-like peptide-1 secretion through TGR5 in a murine enteroendocrine cell line STC-1. Biochem Biophy Res Commun 329:386-390 (2005).
Kawamata et al A G protein-coupled receptor responsive to bile acids. J Biol Chem 278:9435-9440 (2003).
Khailova et al. Inhibition of the apical sodium-dependent bile acid transporter in experimental necrotizing enterocolitis. Database BIOSIS Apr. 2007 XP002715581, Database accession No. PREV200700602750 * abstract * & Gastroenterology 132(4 Suppl. 2):A57 (2007).
Khailova et al. Inhibition of the apical sodium-dependent bile acid transporter in experimental necrotizing enterocolits. Gastroenterology 132(4 Sup 2):A57. Digestive Disease Week Meeting/108th Annual Meeting of the American-Gastroenterological-Association. Washington, D.C. May 19-24, 2007. Database Accession No. PREV200700602750.
Kramer et al. Bile acid reabsorption inhibitors (BARI): novel hypolipidemic drugs. Curr Med Chem (9):997-1016 (2006).
Lee et al. Metforming Decreases Food Consumption and Induces Weight Loss in Subjects with Obesity with Type II Non-Insulin-Dependent Diabetes. Obesity Research 6(1):47-53 (1998).
Lim et al. Glucagon-like peptide 1 secretion by the L-cell. Diabetes 55(Supp 2):S70-77 (2006).
Macchiarulo et al. Molecular field analysis and 3D-quantitiative structure activity relationship study (MFA 3D-QSAR) unveil novel features of bile acid recognition at TGR5. J. Chem. Inf. Model. 48:1792-1801 (2008).
Morsy et al. Gastroprotective effects of the insulin sensitizers rosiglitazone and metformin against indomethacin-induced gastric ulcers in Type 2 diabetic rats. Clin Exp Pharmacol Physiol 37(2):173-177 (2010).
Namba et al. Incretin and Metabolic Syndrome—A new prevention and treatment of diabetes using GLP-1-related drugs. Magazine of Japanese Society of Gastroenterology 102(11):1398-1404 (2005) (w/English translation).
Onaga et al. Multiple regulation of peptide YY secretion in the digestive tract. Peptides 17:279-290 (2002).
PCT/US2009/065587 International Search Report dated Jul. 27, 2010.
PCT/US2011/038251 International Search Report dated Jan. 19, 2012.

Pellicciari et al. Nongenomic actions of bile acids. Synthesis and preliminary characterization of 23- and 6,23-alkyl-substituted bile acid derivatives as selective modulators for the G-protein coupled receptor TGR5. J Med Chem 50:4265-4268 (2007).
Raun et al. Liraglutide, a Long-Action Glucagon-Like Peptide-1 Analog, Reduces Body Weight and Food Intake in Obese Candy-Fed Rats, Whereas a Dipeptidyl Peptidase-IV Inhibitor, Vildagliptin, Does Not. Diabetes 56:8-15 (Jan. 2007).
Reimann et al. Signaling mechanism underlying the release of glucagon-like peptide 1. Diabetes 55(Suppl.2):S78-S85 (2006).
Root et al. Ileal bile acid transporter inhibition, CYP7A1 induction, and antilipemic action of 264W94. J Lipid Res 43(8):1320-1330 (2002).
Sato et al. Anti-hyperglycemic activity of a TGR5 agonist isolated form Olea europaea. Biochem Biophys ResCommun 362:793-798 (2007).
Sato et al. Novel potent and selective bile acid derivatives as TGR5 agonists: biological screening, structure-activity relationships, and molecular modeling studies. J Med Chem 51:1831-1841 (2008).
Spangeus et al. Large intestinal endocrine cells in non-obese diabetic mice. J. Diab. Comp. 12:321-327 (1998).
Tenjarla et al. Release of 5-Aminosalicylate from and MMX mesalamine tablet during transit through a simulated gastrointestinal tract system. Advances in Therapy 23:826-940 (2007).
The Merk Manual, 18th Ed., Japanese Version, the third impression of the first edition, p. 1371-1375 (Apr. 25, 2007).
Thomas et al. Decreased developmental of experimental necrotizing enterocolitis in apical sodium-dependent bile acid transporter knock-out mice. Gastroenterology 136(5 Suppl. 1):A41 (May 2009).
Tozaki et al. Chitosan capsules for colon-specific drug delivery: improvement of insulin absorption from the rat colon. J Pharm Sci 86:1016-1021 (1997).
Tucker et al. Metformin kinetics in healthy subjects and in patients with diabetes mellitus.Br J Clin Pharmacol. 12(2):235-246 (1981).
U.S. Appl. No. 12/623,977 Office Action dated Apr. 26, 2013.
U.S. Appl. No. 12/623,977 Office Action dated Jan. 31, 2012.
U.S. Appl. No. 12/623,977 Office Action dated Mar. 16, 2015.
U.S. Appl. No. 12/623,977 Office Action dated Oct. 24, 2014.
U.S. Appl. No. 12/623,977 Office Action dated Sep. 25, 2012.
U.S. Appl. No. 12/624,345 Notice of Allowance dated Sep. 21, 2012.
U.S. Appl. No. 12/624,345 Office Action dated Feb. 15, 2012.
U.S. Appl. No. 12/624,345 Office Action dated May 26, 2011.
U.S. Appl. No. 12/624,345 Office Action dated Nov. 16, 2011.
U.S. Appl. No. 13/116,988 Office Action dated Jul. 30, 2014.
U.S. Appl. No. 13/116,988 Office Action dated Nov. 15, 2013.
U.S. Appl. No. 13/402,763 Office Action dated May 29, 2014.
U.S. Appl. No. 13/402,763 Office Action dated Oct. 9, 2014.
U.S. Appl. No. 13/402,819 Office Action dated Aug. 1, 2014.
U.S. Appl. No. 13/402,819 Office Action dated Feb. 10, 2016.
U.S. Appl. No. 13/402,819 Office Action dated Jan. 14, 2014.
U.S. Appl. No. 13/402,819 Office Action dated Jul. 7, 2015.
Watanabe. Bile acid and diabetes. Functional Food. 2(1):57-63 (Apr. 2008) (w/English translation).
West et al. SC-435, an ileal apical sodium-codependent bile acid transporter inhibitor alters mRNA levels and enzyme activities of selected genes involved in hepatic cholesterol and lipoprotein metabolism in guinea pigs. Journal of Nutritional Biochemistry 16(12):722-728 (2005).
Wu et al.Expression of bitter taste receptors of the T2R family in the gastrointestinal tract and enteroendocrine STC-1 cells. PNAS USA 99:2392-2397 (2002).
Wynne et al. Appetite Control. J. Endocrinol. 184:291-318 (2005).
Yamamoto et al. Colon-specific delivery of peptide drugs and anti-inflammatory drugs using chitosan capsules. Sciences Techniqus et Pratiques 10:23-34 (2000).
Ziv et al. Bile Salts Promote the Absorption of Insulin from the Rat Colon. Life Sci. 29:803-809 (1981).
Journal of Pharmaceutical Sciences 125(6):379-384 (2005).
U.S. Appl. No. 13/402,819 Office Action dated Aug. 22, 2016.
U.S. Appl. No. 14/555,290 Office Action dated Nov. 16, 2016.
Abraham et al. Surgical and nonsurgical management of gallstones. Am Fam Physician 89(10):795-802 (2014).

(56) References Cited

OTHER PUBLICATIONS

EP0982974.1 Extended Search Report dated Nov. 22, 2012.
U.S. Appl. No. 13/402,819 Office Action dated Apr. 5, 2018.
U.S. Appl. No. 14/555,290 Office Action dated Apr. 19, 2018.
U.S. Appl. No. 13/402,819 Office Action dated May 26, 2017.
U.S. Appl. No. 14/555,290 Office Action dated Jun. 28, 2017.

* cited by examiner

A Compound 100B + DPP-IV inhibitor

B Compound 100B alone

BILE ACID RECYCLING INHIBITORS FOR TREATMENT OF OBESITY AND DIABETES

CROSS-REFERENCE

This application is a continuation of U.S. patent application Ser. No. 12/623,977 filed on Nov. 23, 2009, now U.S. Pat. No. 9,339,480, which claims the benefit of U.S. Provisional Application No. 61/118,356 filed Nov. 26, 2008; U.S. Provisional Application No. 61/239,657 filed Sep. 3, 2009; U.S. Provisional Application No. 61/239,636 filed Sep. 3, 2009; U.S. Provisional Application No. 61/239,663 filed Sep. 3, 2009; and U.S. Provisional Application No. 61/255,205 filed Oct. 27, 2009; each of which is incorporated herein by reference in its entirety.

BACKGROUND OF THE INVENTION

Obesity is a medical condition affecting numerous humans in a number of countries throughout the world, and is associated with or induces other diseases or conditions. In particular, obesity is a serious risk factor for diseases and conditions such as diabetes, hypertension, gallbladder disease, cancer, polycystic ovary disease and arteriosclerosis and can contribute to elevated levels of cholesterol in the blood. In addition, increased body weight due to obesity places a burden on joints causing arthritis, pain, and stiffness. Overeating and obesity have become a problem in the general population. Consequently there is interest in reducing food intake, losing weight, reducing weight, and/or maintaining a healthy body weight and lifestyle.

SUMMARY OF THE INVENTION

Provided herein, in certain embodiments, are therapeutic methods using compounds that inhibit the Apical Sodium-dependent Bile Transporter (ASBT) or any recuperative bile salt transporter. In certain instances, use of the compounds reduces or inhibits recycling of bile acid salts in the gastrointestinal tract. In some embodiments, the bile transport inhibitors are non-systemic compounds. In other embodiments, the bile acid transporter inhibitors are systemic compounds. In certain embodiments, the bile transport inhibitors described herein enhance L-cell secretion of enteroendocrine peptides. In certain instances, increased L-cell secretion of enteroendocrine peptides is associated with induction of satiety and/or reduction of food intake (caloric intake) and subsequent weight loss. In some embodiments, increased L-cell secretion of enteroendocrine peptides is associated with a reduction in blood and/or plasma glucose levels in a hyperglycemic individual. In some instances, increased L-cell secretion of enteroendocrine peptides is associated with increased insulin sensitivity.

In certain of any of the aforementioned embodiments, an ASBTI is any compound described herein that inhibits recycling of bile acids in the gastrointestinal tract of an individual. In certain of any of the aforementioned embodiments, an ASBTI is (−)-(3R,5R)-trans-3-butyl-3-ethyl-2,3,4,5-tetrahydro-7,8-dimethoxy-5-phenyl-1,4-benzothiazepine1,1-dioxide; ("Compound 100A") or any other salt or analog thereof. In certain of any of the aforementioned embodiments, an ASBTI is 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate salt ("Compound 100B") or any other salt or analog thereof. In certain of any of the aforementioned embodiments, an ASBTI is N, N-dimethyl-imido-dicarbonimidic diamide ("Compound 100C") or any salt or analog thereof.

Provided herein are methods for treating obesity or diabetes comprising contacting the distal ileum of an individual in need thereof with an Apical Sodium-dependent Bile Transporter Inhibitor (ASBTI).

In some embodiments of the methods, contacting the distal ileum of an individual in need thereof with an ASBTI
 a. reduces food intake in the individual;
 b. induces satiety in the individual;
 c. reduces blood and/or plasma glucose levels in the individual;
 d. treats a metabolic disorder in the individual;
 e. reduces the weight of the individual;
 f. stimulates L-cells in the distal gastrointestinal tract of the individual;
 g. increases the concentration of bile acids and salts thereof in the vicinity of L-cells in the distal gastrointestinal tract of the individual;
 h. enhances enteroendocrine peptide secretion in the individual; or
 i. any combination thereof.

In some embodiments, the ASBTI is not systemically absorbed. In some other embodiments, the ASBTI is systemically absorbed.

In some embodiments, the methods described above further comprise administration of a second agent selected from a DPP-IV inhibitor, a biguanide, an incretin mimetic, a thiazolidinedione, GLP-1 or an analog thereof, and a TGR5 agonist. In some embodiments, the second agent is a DPP-IV inhibitor.

In some embodiments of the methods, the individual is an obese or morbidly overweight individual. In some embodiments of the methods, the individual is a diabetic individual. In some embodiments of the methods, the individual is a non-diabetic individual.

In some embodiments, provided herein are methods for the treatment of obesity and/or diabetes comprising administration of a therapeutically effective amount of a combination of an ASBTI and a DPP-IV inhibitor to an individual in need thereof. In some embodiments, provided herein are methods for the treatment of obesity and/or diabetes comprising administration of a therapeutically effective amount of a combination of an ASBTI and a TGR5 agonist to an individual in need thereof. In some embodiments, provided herein are methods for the treatment of obesity and/or diabetes comprising administration of a therapeutically effective amount of a combination of an ASBTI and a thiazolidinedione to an individual in need thereof. In some embodiments, provided herein are methods for the treatment of obesity and/or diabetes comprising administration of a therapeutically effective amount of a combination of an ASBTI and an incretin mimic to an individual in need thereof. In some embodiments, provided herein are methods for the treatment of obesity and/or diabetes comprising administration of a therapeutically effective amount of a combination of an ASBTI and GLP-1 or an analog thereof to an individual in need thereof. In some embodiments, provided herein are methods for the treatment of obesity and/or diabetes comprising administration of a therapeutically effective amount of a combination of an ASBTI and a biguanide to an individual in need thereof.

In some embodiments, the methods described herein reduce food intake (caloric intake) in an individual in need thereof. In some embodiments, the methods described herein induce satiety in an individual in need thereof. In some embodiments, the methods described herein treat metabolic disorders in an individual in need thereof. In some embodiments, the methods described herein reduce the weight of an individual in need thereof. In some embodiments, the methods described herein stimulate L-cells in the distal gastrointestinal tract of an individual in need thereof. In some embodiments, the methods described herein increase the concentration of bile acid and salts thereof in the vicinity of L-cells in the distal gastrointestinal tract of an individual.

Provided herein are methods for reducing food intake in an individual in need thereof comprising administration of an Apical Sodium-dependent Bile Acid Transporter Inhibitor (ASBTI) to an individual in need thereof wherein the ASBTI is delivered or released non-systemically in the distal ileum of the individual.

Provided herein are methods for reducing circulating blood or plasma glucose levels in an individual in need thereof comprising administration of an Apical Sodium-dependent Bile Acid Transporter Inhibitor (ASBTI) to an individual in need thereof wherein the ASBTI is delivered or released non-systemically in the distal ileum of the individual.

Provided herein are methods for increasing insulin secretion in an individual in need thereof comprising administration of an Apical Sodium-dependent Bile Acid Transporter Inhibitor (ASBTI) to an individual in need thereof wherein the ASBTI is delivered or released non-systemically in the distal ileum of the individual.

In some embodiments, the methods described herein enhance enteroendocrine peptide secretion in an individual in need thereof. In some of such embodiments, the enteroendocrine peptide is GLP-1, GLP-2, PYY, oxyntomodulin, or a combination thereof.

In some embodiments, contacting the distal ileum of an individual in need thereof with an ASBTI increases the level of GLP-1 in the blood and/or plasma of the individual by from about 2 times to about 6 times the level of GLP-1 in the blood and/or plasma of the individual prior to contacting the distal ileum of the individual with the ASBTI.

In some embodiments, contacting the distal ileum of an individual in need thereof with an ASBTI reduces the level of glucose in the blood and/or plasma of the individual by at least 30% compared to the level of glucose in the blood and/or plasma of the individual prior to contacting the distal ileum of the individual with the ASBTI.

In some embodiments, contacting the distal ileum of an individual in need thereof with an ASBTI maintains reduced blood and/or plasma glucose levels in the individual for at least 24 hours compared to blood and/or plasma glucose levels in the individual prior to contacting the distal ileum of the individual with the ASBTI.

In some embodiments, the ASBTI is administered orally. In some embodiments, the ASBTI is administered as an ileal-pH sensitive release formulation that delivers the ASBTI to the distal ileum, colon and/or rectum of an individual. In some embodiments, the ASBTI is administered as an enterically coated formulation.

In some embodiments of the methods described above, the ASBTI is a compound of Formula I as described herein. In some embodiments of the methods described above, the ASBTI is a compound of Formula II as described herein. In some embodiments of the methods described above, the ASBTI is a compound of Formula III as described herein. In some embodiments of the methods described above, the ASBTI is a compound of Formula IV as described herein. In some embodiments of the methods described above, the ASBTI is a compound of Formula V as described herein. In some embodiments of the methods described above, the ASBTI is a compound of Formula VI or Formula VID as described herein.

In some embodiments of the methods described above, the ASBTI is administered before ingestion of food. In some embodiments of the methods described above, the ASBTI is administered less than about 60 minutes before ingestion of food. In some embodiments of the methods described above, the ASBTI is administered less than about 30 minutes before ingestion of food. In some embodiments of the methods described above, the ASBTI is administered after ingestion of food.

Provided herein are methods for prevention and/or treatment of congestive heart failure, ventricular dysfunction, toxic hypervolemia, polycystic ovary syndrome, inflammatory bowel disease, impaired bowel integrity, short bowel syndrome, gastritis, peptic ulcer, or irritable bowel disease comprising contacting the distal ileum of an individual in need thereof with an ASBTI. In some embodiments, the methods further comprise administration of a DPP-IV inhibitor, a TGR5 agonist, a biguanide, an incretin mimetic, or GLP-1 or an analog thereof. Provided herein are methods for prevention and/or treatment of radiation enteritis comprising contacting the distal ileum of an individual in need thereof with an ASBTI. In some embodiments, the methods further comprise administration of a DPP-IV inhibitor, a TGR5 agonist, a biguanide, an incretin mimetic, or GLP-1 or an analog thereof.

Provided herein are compositions for reducing caloric intake in an individual in need thereof comprising an Apical Sodium-dependent Bile Acid Transporter Inhibitor (ASBTI), and a pharmaceutically acceptable carrier, wherein the ASBTI is delivered or released non-systemically in the distal ileum of the individual. Provided herein are compositions for reducing circulating blood and/or plasma glucose levels in an individual in need thereof comprising an Apical Sodium-dependent Bile Acid Transporter Inhibitor (ASBTI), and a pharmaceutically acceptable carrier, wherein the ASBTI is delivered or released non-systemically in the distal ileum of the individual. Provided herein are compositions for increasing insulin secretion in an individual in need thereof comprising an Apical Sodium-dependent Bile Acid Transporter Inhibitor (ASBTI), and a pharmaceutically acceptable carrier, wherein the ASBTI is delivered or released non-systemically in the distal ileum of the individual. In any of the aforementioned embodiments, the compositions further comprise a DPP-IV inhibitor, a TGR5 agonist, a biguanide, an incretin mimetic, or GLP-1 or an analog thereof.

Provided herein, in some embodiments, are ASBTIs for reducing food intake (caloric intake) or for reducing circulating blood or plasma glucose levels wherein the ASBTI is not absorbed systemically following oral administration. In some of such embodiments, the ASBTI is a compound of Formula I, II, III, IV, V or VI as described herein. In some of such embodiments, the ASBTI is prevented from being absorbed in the stomach by its presence in a formulation that releases it in the ileum. In some of such embodiments, the ASBTI is administered in combination with a second therapeutic agent selected from a DPP-IV inhibitor, a biguanide, a thiazolidinedione, an increin mimetic, GLP-1 or an analog thereof, or a TGR5 agonist.

DETAILED DESCRIPTION OF THE INVENTION

Figure 1:
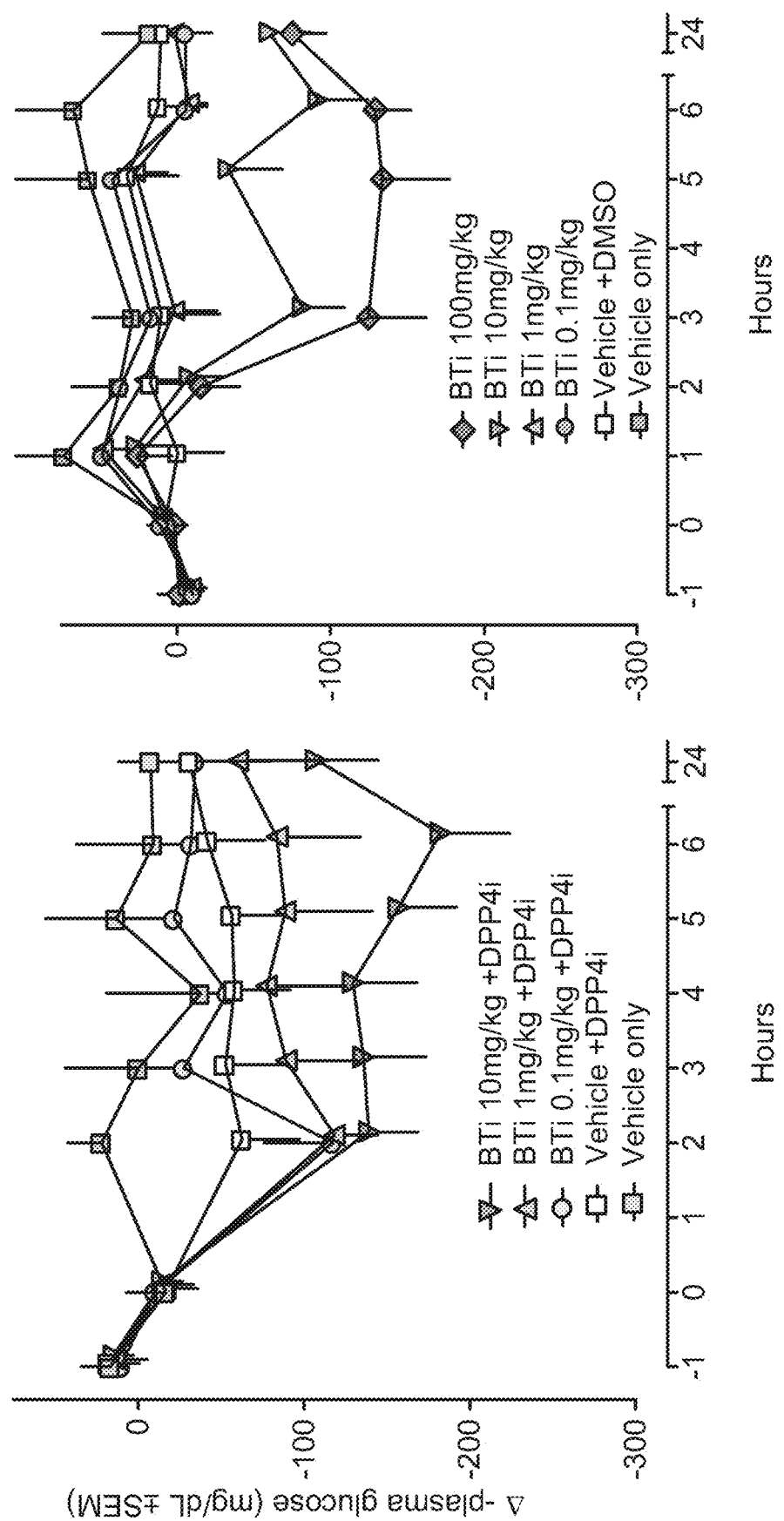
FIG. 1 illustrates the change in plasma glucose level in diabetic db/db mice after oral administration of a combination of the ASBTI (−)-(3R,5R)-trans-3-butyl-3-ethyl-2,3,4,5-tetrahydro-7,8-dimethoxy-5-phenyl-1,4-benzothiazepine1,1-dioxide at doses of 0, 0.1, 1, 10 mg/kg and 30 mg/kg sitagliptin (DPP-IV inhibitor) and the ASBTI alone.

Described herein is the use of inhibitors of the Apical Sodium-dependent Bile Transporter (ASBT) or any recuperative bile salt transporter that are active in the gastrointestinal (GI) tract for induction of weight loss in an individual in need thereof. In some embodiments, such ASBT inhibitiors are systemically absorbed. In some embodiments, such ASBT inhibitiors are not systemically absorbed. In some of such embodiments, such bile salt transport inhibitors include a moiety or group that prevents, reduces or inhibits the systemic absorption of the compound in vivo. In some embodiments, a charged moiety or group on the compounds prevents, reduces or inhibits the compounds from leaving the gastrointestinal tract and reduces the risk of side effects due to systemic absorption. In some embodiments, the ASBTIs are formulated for delivery to the distal ileum. In certain embodiments, ASBTIs described herein inhibit scavenging of bile salts by recuperative bile acid salt transporters in the distal gastrointestinal tract (e.g., the distal ileum, the colon and/or the rectum).

In some instances, the inhibition of bile salt recycling results in higher concentrations of bile salts in the lumen of the distal gastrointestinal tract or portions thereof (e.g., the distal small bowel and/or colon and/or rectum). As used herein, the distal gastrointestinal tract includes the region from the distal ileum to the anus. In certain embodiments, the higher concentration of bile salts in the distal small bowel and/or colon and/or rectum modulates (e.g., enhances) the secretion of enteroendocrine peptides in the distal gastrointestinal tract. In some embodiments, the compounds described herein enhance the secretion of enteroendocrine peptides (e.g., GLP-1, GLP-2, oxyntomodulin, PYY, or a combination thereof) from L-cells that are present in the distal ileum, colon and/or the rectum. In certain embodiments, the enhanced secretion of L-cell enteroendocrine peptides modulates (e.g., slows or inhibits) gastric emptying and gastric acid secretion. In certain instances the enhanced secretion of L-cell enteroendocrine peptides induces a feeling of satiety. In some embodiments, the enhanced secretion of L-cell enteroendocrine peptides reduces food intake thereby inducing weight loss.

Also described herein is the use of such compounds for reducing or maintaining weight in individuals (e.g., individuals interested in losing weight, reducing weight, and/or maintaining a healthy body weight and lifestyle). In certain instances, the compounds described herein are useful in the treatment of diseases or conditions that are modulated by enteroendocrine peptides secreted by L-cells of the distal gastrointestinal tract, including L-cells in the distal ileum, the colon and/or the rectum. In some instances, enhanced enteroendocrine peptide secretion (e.g., increase in GLP-1 secretion) reduces blood or plasma glucose levels. In some embodiments, the compounds described herein are also useful in the treatment of metabolic disorders (e.g., diabetes, metabolic syndrome or the like) because they do not cause side effects (e.g., weight gain) that are associated with conventional therapies for metabolic disorders.

Compounds

In some embodiments, provided herein are ASBT inhibitors that reduce or inhibit bile acid recycling in the distal gastrointestinal (GI) tract, including the distal ileum, the colon and/or the rectum. In certain embodiments, the ASB-TIs are systemically absorbed. In certain embodiments, the ASBTIs are not systemically absorbed. In some embodiments, ASBTIs described herein are modified or substituted (e.g., with a -L-K group) to be non-systemic. In certain embodiments, any ASBT inhibitor is modified or substituted with one or more charged groups (e.g., K) and optionally, one or more linker (e.g., L), wherein L and K are as defined herein.

In some embodiments, an ASBTI suitable for the methods described herein is a compound of Formula I:

Formula I

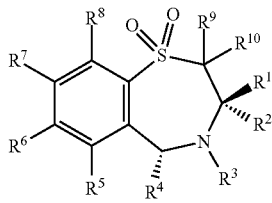

wherein:

$R^1$ is a straight chained $C_{1-6}$ alkyl group;

$R^2$ is a straight chained $C_{1-6}$ alkyl group;

$R^3$ is hydrogen or a group $OR^{11}$ in which $R^{11}$ is hydrogen, optionally substituted $C_{1-6}$ alkyl or a $C_{1-6}$ alkylcarbonyl group;

$R^4$ is pyridyl or optionally substituted phenyl or -$L_z$-$K_z$; wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;

$R^5$, $R^6$, $R^7$ and $R^8$ are the same or different and each is selected from hydrogen, halogen, cyano, $R^5$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, $OCF_3$, $OCN$, $SCN$, $NHCN$, $CH_2OR^{15}$, $CHO$, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH=CHR^{15}$, $O(CH_2CH_2O)_nR^{15}$, $O(CH_2)_pSO_3R^{15}$, $O(CH_2)_pNR^{12}R^{13}$, $O(CH_2)_pN^+R^{12}R^{13}R^{14}$ and —W—$R^{31}$, wherein W is O or NH and $R^{31}$ is selected from

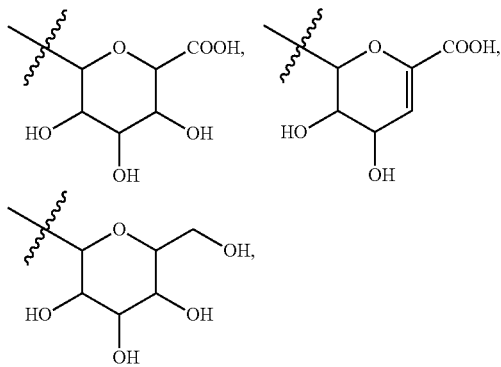

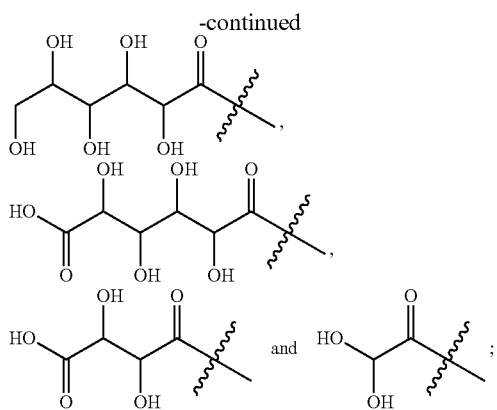

wherein p is an integer from 1-4, n is an integer from 0-3 and, $R^{12}$, $R^{13}$, $R^{14}$ and $R^{15}$ are independently selected from hydrogen and optionally substituted $C_{1-6}$ alkyl; or $R^6$ and $R^7$ are linked to form a group

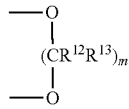

wherein $R^{12}$ and $R^{13}$ are as hereinbefore defined and m is 1 or 2; and $R^9$ and $R^{10}$ are the same or different and each is selected from hydrogen or $C_{1-6}$ alkyl; and salts, solvates and physiologically functional derivatives thereof.

In some embodiments of the methods, the compound of Formula I is a compound
wherein
$R^1$ is a straight chained $C_{1-6}$ alkyl group;
$R^2$ is a straight chained $C_{1-6}$ alkyl group;
$R^3$ is hydrogen or a group $OR^{11}$ in which $R^{11}$ is hydrogen, optionally substituted $C_{1-6}$ alkyl or a $C_{1-6}$ alkylcarbonyl group;
$R^4$ is optionally substituted phenyl;
$R^5$, $R^6$ and $R^8$ are independently selected from hydrogen, $C_{1-4}$ alkyl optionally substituted by fluorine, $C_{1-4}$ alkoxy, halogen, or hydroxy;
$R^7$ is selected from halogen, cyano, $R^{15}$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, $OCF_3$, $OCN$, $SCN$, $HNCN$, $CH_2OR^{15}$, $CHO$, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH=CHR^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$;
wherein n, p and $R^{12}$ to $R^{15}$ are as hereinbefore defined; with the proviso that at least two of $R^5$ to $R^8$ are not hydrogen; and
salts solvates and physiologically functional derivatives thereof.

In some embodiments of the methods described herein, the compound of Formula I is a compound
wherein
$R^1$ is a straight chained $C_{1-6}$ alkyl group;
$R^2$ is a straight chained $C_{1-6}$ alkyl group;
$R^3$ is hydrogen or a group $OR^{11}$ in which $R^{11}$ is hydrogen, optionally substituted $C_{1-6}$ alkyl or a $C_{1-6}$ alkylcarbonyl group;

$R^4$ is un-substituted phenyl;
$R^5$ is hydrogen or halogen;
$R^6$ and $R^8$ are independently selected from hydrogen, $C_{1-4}$ alkyl optionally substituted by fluorine, $C_{1-4}$ alkoxy, halogen, or hydroxy;
$R^7$ is selected from $OR^{15}$, $S(O)R^{15}$, $OCOR^{15}$, $OCF_3$, OCN, SCN, CHO, $OCH_2OR^{15}$, $OCH=CHR^{15}$, $O(CH_2CH_2O)_n R^{15}$, $O(CH_2)_p SO_3 R^{15}$, $O(CH_2)_p NR^{12}R^{13}$ and $O(CH_2)_p N^+ R^{12}R^{13}R^{14}$ wherein p is an integer from 1-4, n is an integer from 0-3, and $R^{12}$, $R^{13}$, $R^{14}$, and $R^{15}$ are independently selected from hydrogen and optionally substituted $C_{1-6}$ alkyl;
$R^9$ and $R^{10}$ are the same or different and each is selected from hydrogen or $C_{1-6}$ alkyl; and
salts, solvates and physiologically functional derivatives thereof.

In some embodiments of the methods, wherein the compound of Formula I is a compound wherein
$R^1$ is methyl, ethyl or n-propyl;
$R^2$ is methyl, ethyl, n-propyl, n-butyl or n-pentyl;
$R^3$ is hydrogen or a group $OR^{11}$ in which $R^{11}$ is hydrogen, optionally substituted $C_{1-6}$ alkyl or a $C_{1-6}$ alkylcarbonyl group;
$R^4$ is un-substituted phenyl;
$R^5$ is hydrogen;
$R^6$ and $R^8$ are independently selected from hydrogen, $C_{1-4}$ alkyl optionally substituted by fluorine, $C_{1-4}$ alkoxy, halogen, or hydroxy;
$R^7$ is selected from $OR^{15}$, $S(O)R^{15}$, $OCOR^{15}$, $OCF_3$, OCN, SCN, CHO, $OCH_2OR^{15}$, $OCH=CHR^{15}$, $O(CH_2CH_2O)_n R^{15}$, $O(CH_2)_p SO_3 R^{15}$, $O(CH_2)_p NR^{12}R^{13}$ and $O(CH_2)_p N^+ R^{12}R^{13}R^{14}$ wherein p is an integer from 1-4, n is an integer from 0-3, and $R^{12}$, $R^{13}$, $R^{14}$, and $R^{15}$ are independently selected from hydrogen and optionally substituted $C_{1-6}$ alkyl;
$R^9$ and $R^{10}$ are the same or different and each is selected from hydrogen or $C_{1-6}$ alkyl; and
salts, solvates and physiologically functional derivatives thereof.

In some embodiments of the methods, the compound of Formula I is a compound
wherein
$R^1$ is methyl, ethyl or n-propyl;
$R^2$ is methyl, ethyl, n-propyl, n-butyl or n-pentyl;
$R^3$ is hydrogen or a group $OR^{11}$ in which $R^{11}$ is hydrogen, optionally substituted $C_{1-6}$ alkyl or a $C_{1-6}$ alkylcarbonyl group;
$R^4$ is un-substituted phenyl;
$R^5$ is hydrogen;
$R^6$ is $C_{1-4}$ alkoxy, halogen, or hydroxy;
$R^7$ is $OR^{15}$, wherein $R^{15}$ is hydrogen or optionally substituted $C_{1-6}$ alkyl;
$R^8$ is hydrogen or halogen;
$R^9$ and $R^{10}$ are the same or different and each is selected from hydrogen or $C_{1-6}$ alkyl; and
salts, solvates and physiologically functional derivatives thereof.

In some embodiments of the methods, the compound of Formula I is
(3R,5R)-3-Butyl-3-ethyl-2,3,4,5-tetrahydro-7,8-dimethoxy-5-phenyl-1,4-benzothiazepine 1,1-dioxide;
(3R,5R)-3-Butyl-3-ethyl-2,3,4,5-tetrahydro-7,8-dimethoxy-5-phenyl-1,4-benzothiazepin-4-ol 1,1-dioxide;
(±)-Trans-3-butyl-3-ethyl-2,3,4,5-tetrahydro-7,8-dimethoxy-5-phenyl-1,4-benzothiazepine 1,1-dioxide;
(±)-Trans-3-butyl-3-ethyl-2,3,4,5-tetrahydro-7,8-dimethoxy-5-phenyl-1,4,-benzothiazepin-4-ol 1,1-dioxide;
(3R,5R)-7-Bromo-3-butyl-3-ethyl-2,3,4,5-tetrahydro-8-methoxy-5-phenyl-1,4-benzothiazepine 1,1-dioxide;
(3R,5R)-7-Bromo-3-butyl-3-ethyl-2,3,4,5-tetrahydro-8-methoxy-5-phenyl-1,4-benxothiaxepin-4-ol 1,1-dioxide;
(3R,5R)-3-Butyl-3-ethyl-2,3,4,5-tetrahydro-5-phenyl-1,4-benzothiazepine-7,8-diol 1,1-dioxide;
(3R,5R)-3-Butyl-3-ethyl-2,3,4,5-tetrahydro-8-methoxy-5-phenyl-1,4-benzothiazepin-7-ol 1,1-dioxide;
(3R,5R)-3-Butyl-3-ethyl-2,3,4,5-tetrahydro-7-methoxy-5-phenyl-1,4-benzothiazepin-8-ol 1,1-dioxide;
(±)-Trans-3-butyl-3-ethyl-2,3,4,5-tetrahydro-8-methoxy-5-phenyl-1,4-benzothiazepine 1,1-dioxide;
(±)-Trans-3-butyl-3-ethyl-2,3,4,5-tetrahydro-5-phenyl-1,4-benzothiazepin-8-ol 1,1-dioxide;
(±)-Trans-3-butyl-3-ethyl-2,3,4,5-tetrahydro-5-phenyl-1,4-benzothiazepine-4,8-diol;
(±)-Trans-3-butyl-3-ethyl-2,3,4,5-tetrahydro-5-phenyl-1,4-benzothiazepin-8-thiol 1,1-dioxide;
(±)-Trans-3-butyl-3-ethyl-2,3,4,5-tetrahydro-5-phenyl-1,4-benzothiazepin-8-sulfonic acid 1,1-dioxide;
(±)-Trans-3-butyl-3-ethyl-2,3,4,5-tetrahydro-8,9-dimethoxy-5-phenyl-1,4-benzothiazepine 1, 1-dioxide;
(3R,5R)-3-butyl-7,8-diethoxy-2,3,4,5-tetrahydro-5-phenyl-1,4-benzothiazepine 1,1-dioxide;
(±)-Trans-3-butyl-8-ethoxy-3-ethyl-2,3,4,5-tetrahydro-5-phenyl-1,4-benzothiazepine 1,1-dioxide;
(±)-Trans-3-butyl-3-ethyl-2,3,4,5-tetrahydro-8-isopropoxy-5-phenyl-1,4-benzothiazepine 1,1-dioxide hydrochloride;
(±)-Trans-3-butyl-3-ethyl-2,3,4,5-tetrahydro-5-phenyl-1,4-benzothiazepin-8-carbaldehyde-1,1-dioxide;
3,3-Diethyl-2,3,4,5-tetrahydro-7,8-dimethoxy-5-phenyl-1,4-benzothiazepine 1,1-dioxide;
3,3-Diethyl-2,3,4,5-tetrahydro-8-methoxy-5-phenyl-1,4-benzothiazepine 1,1-dioxide;
3,3-Diethyl-2,3,4,5-tetrahydro-5-phenyl-1,4-benzothiazpin-4,8-diol 1,1-dioxide;
(RS)-3,3-Diethyl-2,3,4,5-tetrahydro-4-hydroxy-7,8-dimethoxy-5-phenyl-1,4-benzothiazepine 1,1-dioxide;
(±)-Trans-3-butyl-8-ethoxy-3-ethyl-2,3,4,5-tetrahydro-5-phenyl-1,4-benzothiazepin-4-ol-1-dioxide;
(±)-Trans-3-butyl-3-ethyl-2,3,4,5-tetrahydro-8-isopropoxy-5-phenyl-1,4-benzothiazepin-4-ol 1,1-dioxide;
(±)-Trans-3-butyl-3-ethyl-2,3,4,5-tetrahydro-7,8,9-trimethoxy-5-phenyl-1,4-benzothiazepin-4-ol 1,1-dioxide;
(3R,5R)-3-butyl-3-ethyl-2,3,4,5-tetrahydro-5-phenyl-1,4-benzothiazepin-4,7,8-triol 1,1-dioxide;
(±)-Trans-3-butyl-3-ethyl-2,3,4,5-tetrahydro-4,7,8-trimethoxy-5-phenyl-1,4-benzothiazepine 1,1-dioxide;
3,3-Diethyl-2,3,4,5-tetrahydro-5-phenyl-1,4-benzothiazepin-8-ol 1,1-dioxide;
3,3-Diethyl-2,3,4,5-tetrahydro-7-methoxy-5-phenyl-1,4-benzothiazepin-8-ol 1,1-dioxide;
3,3Dibutyl-2,3,4,5-tetrahydro-5-phenyl-1,4-benzothiazepin-8-ol 1,1-dioxide;
(±)-Trans-3-Butyl-3-ethyl-2,3,4,5-tetrahydro-1,1-dioxo-5-phenyl-1,4-benzothiazepin-8-yl hydrogen sulfate; or
3,3-Diethyl-2,3,4,5-tetrahydro-1,1-dioxo-5-phenyl-1,4-benzothiazepin-8-yl hydrogen sulfate.

In some embodiments, the compound of Formula I is

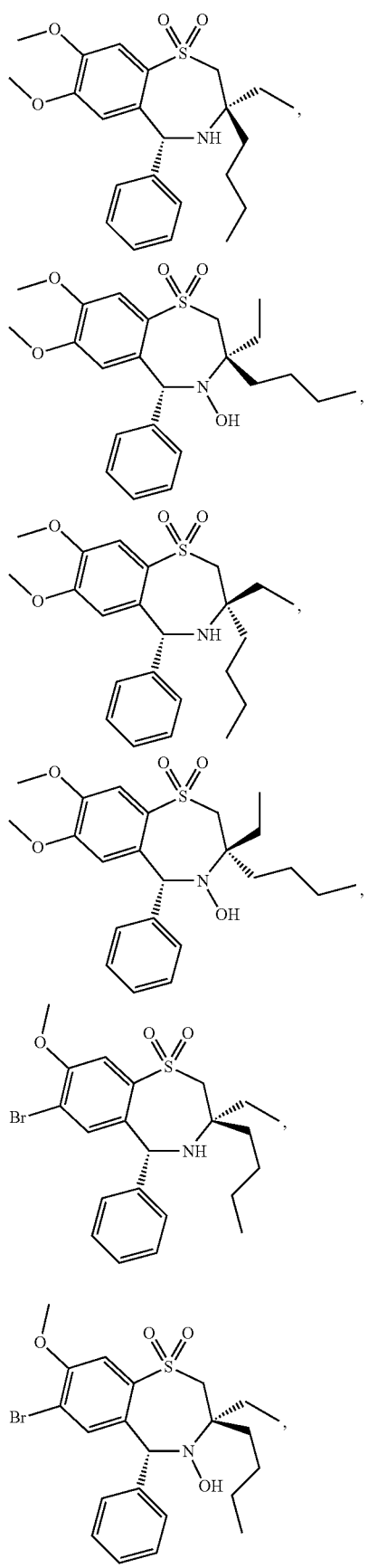
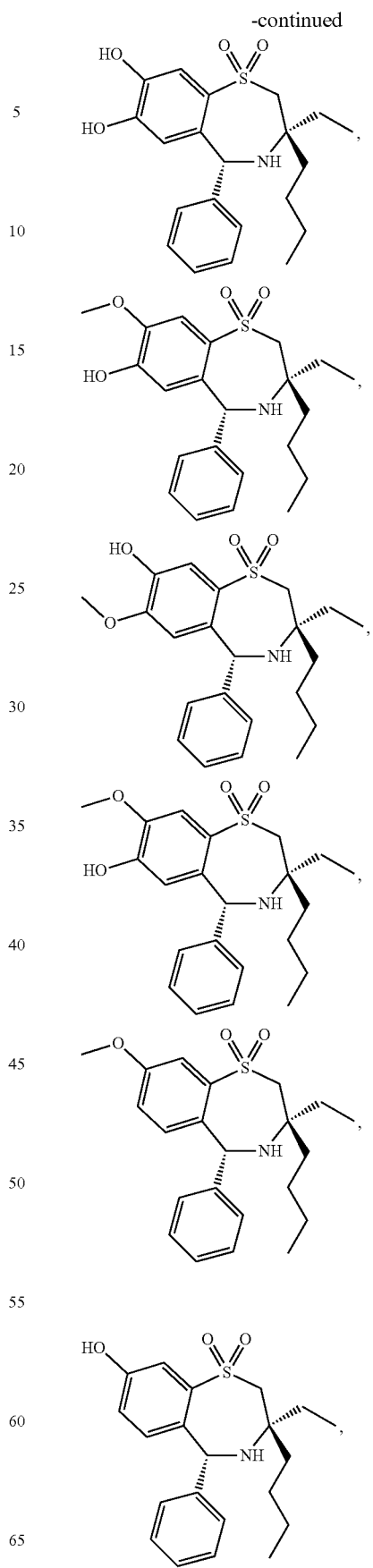

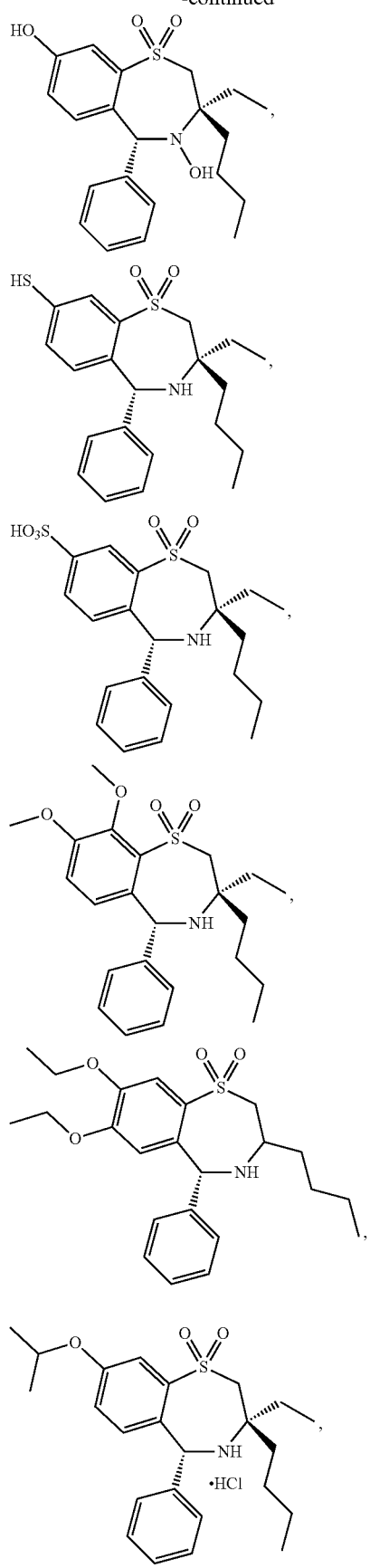
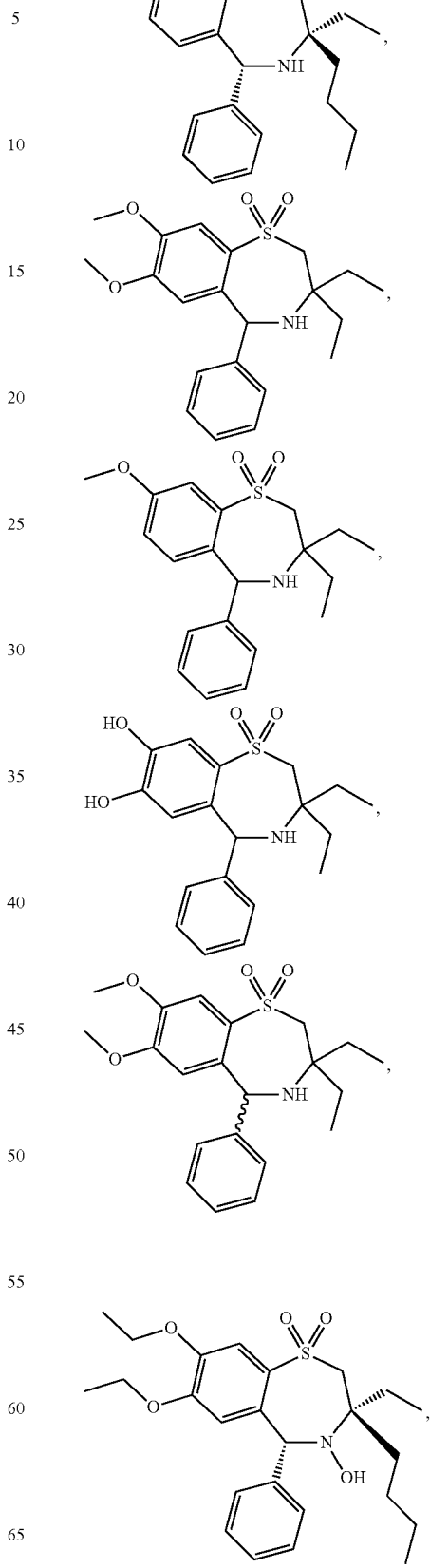

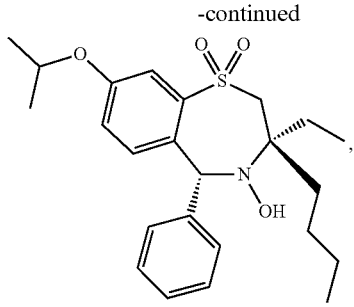
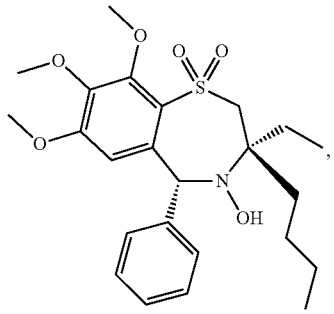
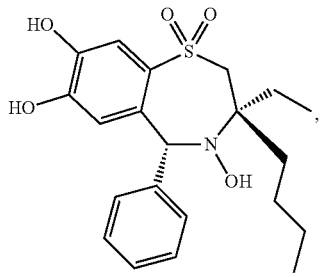
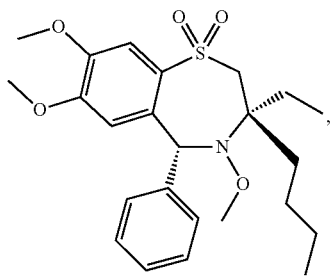
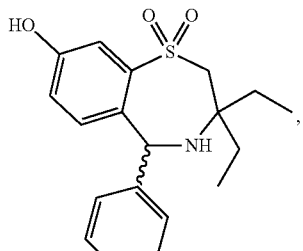
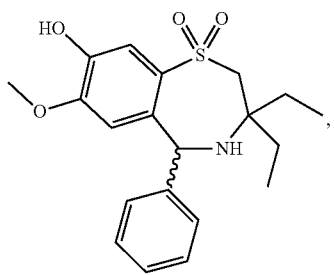
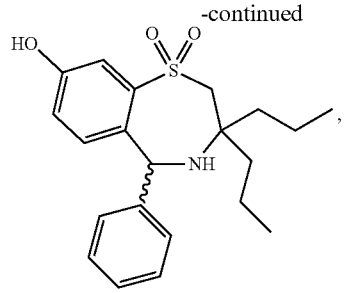
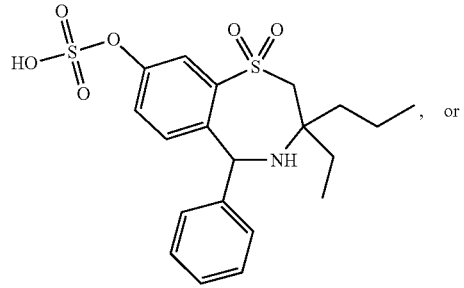
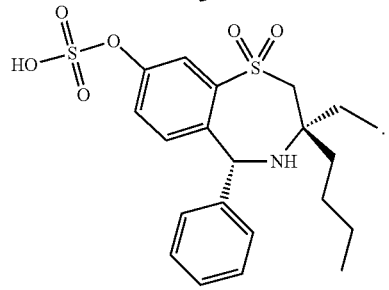
In some embodiments of the methods, the compound of Formula I is
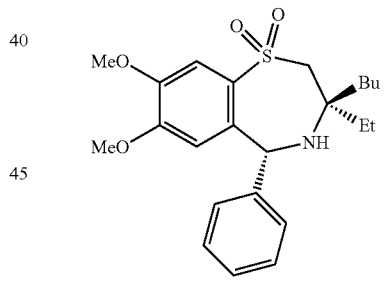
In some embodiments, an ASBTI suitable for the methods described herein is a compound of Formula II
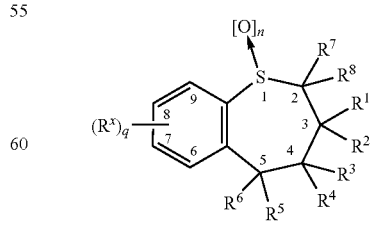
wherein:
q is an integer from 1 to 4;
n is an integer from 0 to 2;

$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, and alkylammoniumalkyl; or $R^1$ and $R^2$ taken together with the carbon to which they are attached form $C_3$-$C_{10}$ cycloalkyl;

$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together =O, =$NOR^{11}$, =S, =$NNR^{11}R^{12}$, =$NR^9$, or =$CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^5$ and $R^6$ are independently selected from the group consisting of H, alkyl, alkenyl, alkynyl, aryl, cycloalkyl, heterocycle, quaternary heterocycle, quaternary heteroaryl, $OR^{30}$, $SR^9$, $S(O)R^9$, $SO_2R^9$, $SO_3R^9$, and -$L_z$-$K_z$;

wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;

wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)N^+R^{13}R^{14}$, $C(O)OM$, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$ wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $N^+R^7R^8$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$ and wherein said alkyl, alkenyl, alkynyl, polyalkyl, polyether, aryl, haloalkyl, cycloalkyl, and heterocycle can optionally have one or more carbons replaced by O, $N^+R^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, PR, $P^+R^9R^{10}A^-$, $P(O)R^9$, phenylene, carbohydrate, amino acid, peptide, or polypeptide, and $R^{13}$, $R^{14}$ and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O) R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring; and is selected from the group consisting of alkyl, alkenyl, alkynyl, cycloalkyl, aryl, acyl, heterocycle, ammoniumalkyl, alkylammoniumalkyl, and arylalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, $C(O)OM$, $COR^{13}$, $OR^{18}$, $S(O)_n$, $NR^{18}$, $NR^{13}R^{18}$, $NR^{18}R^{14}$, $N^+12^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)M, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, SO$_3$R$^9$, oxo, CO$_3$R$^9$, CN, halogen, CONR$^9$R$^{10}$, SO$_3$R$^9$, SO$_2$OM, SO$_2$NR$^9$R$^{10}$, PO(OR$^{16}$)OR$^{17}$, and C(O)OM, wherein in R$^x$, one or more carbons are optionally replaced by O, NR$^{13}$, N$^+$R$^{13}$R$^{14}$A$^-$, S, SO, SO$_2$, SR$^{13}$A$^-$, PR$^{13}$, P(O)R$^{13}$, P$^+$R$^{13}$R$^{14}$A$^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, NR$^9$, R$^9$R$^{10}$A$^-$, S, SO, SO$_2$, S$^+$R$^9$A$^-$, PR$^9$, p+R$^9$R$^{10}$A$^-$, or P(O)R$^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, OR$^{13}$, NR$^{13}$R$^{14}$, SR$^{13}$, S(O)R$^3$, SO$_2$R$^{13}$, SO$_3$R$^{13}$, NR$^{13}$OR$^{14}$, NR$^{13}$NR$^{14}$R$^{15}$, NO$_2$, CO$_2$R$^{13}$, CN, OM, SO$_2$OM, SO$_2$NR$^{13}$R$^{14}$, C(O)NR$^{13}$R$^{14}$, C(O)OM, COR$^{13}$, P(O)R$^{13}$R$^{14}$, P$^+$R$^{13}$R$^{14}$R$^{15}$A$^-$, P(OR$^{13}$)OR$^{14}$, S$^+$R$^{13}$R$^{14}$A$^-$, and NR$^9$R$^{11}$R$^{12}$A$^-$, provided that both R$^5$ and R$^6$ cannot be hydrogen or SH;
provided that when R$^5$ or R$^6$ is phenyl, only one of R$^1$ or R$^2$ is H;
provided that when q=1 and R$^x$ is styryl, anilido, or anilinocarbonyl, only one of R$^5$ or R$^6$ is alkyl;

or a pharmaceutically acceptable salt, solvate, or prodrug thereof.

In some embodiments of the methods, the compound of Formula II is a compound
wherein
R$^5$ and R$^6$ are independently selected from the group consisting of H, aryl, heterocycle, quaternary heterocycle, and quarternary heteroaryl
wherein the aryl, heteroaryl, quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, OR$^{13}$, NR$^{13}$R$^{14}$, SR$^{13}$, S(O)R$^{13}$, SO$_2$R$^{13}$, SO$_3$R$^{13}$, NR$^{13}$OR$^{14}$, NR$^{13}$NR$^{14}$R$^{15}$, NO$_2$, CO$_2$R$^{13}$, CN, OM, SO$_2$OM, SO$_2$NR$^{13}$R$^{14}$, C(O)NR$^{13}$R$^{14}$, C(O)OM, COR$^{13}$, P(O)R$^{13}$R$^{14}$, P$^+$R$^{13}$R$^{14}$R$^{15}$A$^-$, P(OR$^{13}$)OR$^{14}$, S$^+$R$^{13}$R$^{14}$A$^-$, N$^+$R$^9$R$^{11}$R$^{12}$A$^-$ and -L$_z$-K$_z$.

In some embodiments of the methods, the compound of Formula II is a compound
wherein
R$^5$ or R$^6$ is —Ar—(R$^y$)$_t$
t is an integer from 0 to 5;
Ar is selected from the group consisting of phenyl, thiophenyl, pyridyl, piperazinyl, piperonyl, pyrrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl; and
one or more R$^y$ are independently selected from the group consisting of alkyl, alkenyl, alkynyl, polyalkyl, polyether, aryl, halo alkyl, cycloalkyl, heterocycle, arylalkyl, halogen, oxo, OR$^{13}$, NR$^{13}$R$^{14}$, SR$^{13}$, S(O)R$^{13}$, SO$_2$R$^{13}$, SO$_3$R$^{13}$, NR$^{13}$OR$^{14}$, NR$^{13}$NR$^{14}$R$^{15}$, NO$_2$, CO$_2$R$^{13}$, CN, OM, SO$_2$OM, SO$_2$NR$^{13}$R$^{14}$, C(O)NR$^{13}$R$^{14}$, C(O)OM, COR$^{13}$, P(O)R$^{13}$R$^{14}$, P$^+$R$^{13}$R$^{14}$R$^{15}$A$^-$, P(OR$^{13}$)OR$^{14}$, S$^+$R$^{13}$R$^{14}$A$^-$, N$^+$R$^9$R$^{11}$R$^{12}$A$^-$ and -L$_z$-K$_z$;

wherein said alkyl, alkenyl, alkynyl, polyalkyl, polyether, aryl, haloalkyl, cycloalkyl, and heterocycle can be further substituted with one or more substituent groups selected from the group consisting of OR$^{13}$, NR$^{13}$R$^{14}$, SR$^{13}$, S(O)R$^{13}$, SO$_2$R$^{13}$, SO$_3$R$^{13}$, NR$^{13}$OR$^{14}$, NR$^{13}$NR$^{14}$R$^{15}$, NO$_2$, CO$_2$R$^{13}$, CN, oxo, CONR$^7$R$^8$, N$^+$R$^7$R$^8$R$^9$A$^-$, alkyl, alkenyl, alkynyl, aryl, cycloalkyl, heterocycle, arylalkyl, quaternary heterocycle, quaternary heteroaryl, P(O)R$^7$R$^8$, P$^+$R$^7$R$^8$A$^-$, and P(O)(OR$^7$)OR$^8$, and or phenylene;

wherein said alkyl, alkenyl, alkynyl, polyalkyl, polyether, aryl, haloalkyl, cycloalkyl, and heterocycle can optionally have one or more carbons replaced by O, N$^+$R$^7$, N$^+$R$^7$R$^8$A$^-$, S, SO, SO$_2$, S$^+$R$^7$A$^-$, PR$^7$, P(O)R$^7$, P$^+$R$^7$R$^8$A$^-$, or phenylene.

In some embodiments of the methods, the compound of Formula II is a compound wherein R$^5$ or R$^6$ is

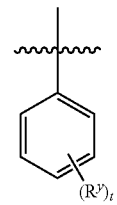

In some embodiments of the methods, the compound of Formula II is a compound wherein n is 1 or 2. In some embodiments of the methods, the compound of Formula II is a compound wherein R$^1$ and R$^2$ are independently H or C$_{1-7}$ alkyl. In some embodiments of the methods, the compound of Formula II is a compound wherein each C$_{1-7}$ alkyl is independently ethyl, n-propyl, n-butyl, or isobutyl. In some embodiments of the methods, the compound of Formula II is a compound wherein R$^3$ and R$^4$ are independently H or OR$^9$. In some embodiments of the methods, compound of Formula II is a compound wherein R$^9$ is H In some embodiments of the methods, the compound of Formula II is a compound wherein one or more R$^x$ are in the 7-, 8- or 9-position of the benzo ring of Formula II. In some embodiments of the methods, the compound of Formula II is a compound wherein R$^x$ is in the 7-position of the benzo ring of Formula II. In some embodiments of the methods, the compound of Formula II is a compound wherein one or more R$^x$ are independently selected from OR$^{13}$ and NR$^{13}$R$^{14}$ In some embodiments of the methods, the compound of Formula II is a compound
wherein:
q is 1 or 2;
n is 2;
R$^1$ and R$^2$ are each alkyl;
R$^3$ is hydroxy;
R$^4$ and R$^6$ are hydrogen;
R$^5$ has the formula

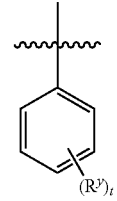

wherein
t is an integer from 0 to 5;
one or more R$^r$ are OR$^{13}$;

R¹³ is selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl;

said R¹³ alkyl, alkenyl, alkynyl, arylalkyl, heterocycle, and polyalkyl groups optionally have one or more carbons replaced by O, NR⁹, N⁺R⁹R¹⁰A⁻, S, SO, SO₂, S⁺R⁹A⁻, PR⁹, p+R⁹R¹⁰A⁻, P(O)R⁹, phenylene, carbohydrate, amino acid, peptide, or polypeptide;

R¹³ is optionally substituted with one or more groups selected from the group consisting of sulfoalkyl, quaternary heterocycle, quaternary heteroaryl, OR⁹, NR⁹R¹⁰, N⁺R⁹R¹¹R¹²A⁻, SR⁹, S(O)R⁹, SO₂R⁹, SO₃R⁹, oxo, CO₂R⁹, CN, halogen, CONR⁹R¹⁰, SO₂OM, SO₂NR⁹R¹⁰, PO(OR¹⁶)OR¹⁷, P⁺R⁹R¹⁰R¹¹A⁻, S⁺R⁹R¹⁰A⁻, and C(O)OM, wherein A is a pharmaceutically acceptable anion, and M is a pharmaceutically acceptable cation, R⁹ and R¹⁰ are independently selected from the group consisting of H, alkyl, alkenyl, alkynyl, cycloalkyl, aryl, acyl, heterocycle, ammoniumalkyl, arylalkyl, and alkylammoniumalkyl;

R¹¹ and R¹² are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, OR⁹, NR⁹R¹⁰, SR⁹, S(O)R⁹, SO₂R⁹, SO₃R⁹, CO₂R⁹, CN, halogen, oxo, and CONR⁹R¹⁰, wherein R⁹ and R¹⁰ are as defined above, provided that both R³ and R⁴ cannot be OH, NH₂, and SH; or R¹¹ and R¹² together with the nitrogen or carbon atom to which they are attached form a cyclic ring; and R¹⁶ and R¹⁷ are independently selected from the substituents constituting R⁹ and M;

R⁷ and R⁸ are hydrogen; and one or more Rˣ are independently selected from the group consisting of alkoxy, alkylamino and dialkylamino and —W—R³¹, wherein W is O or NH and R³¹ is selected from

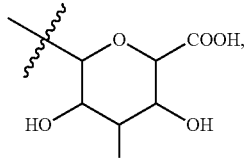
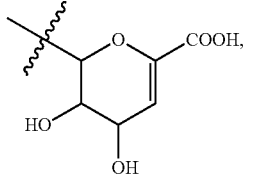
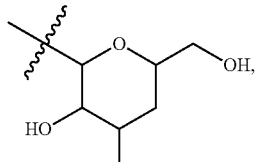
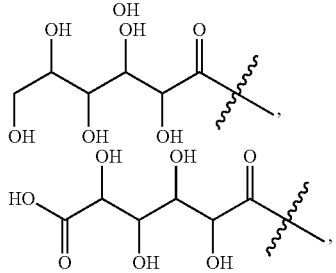
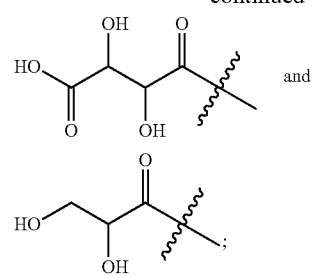

or a pharmaceutically acceptable salt, solvate, or prodrug thereof.

In some embodiments, a compound of Formula II is

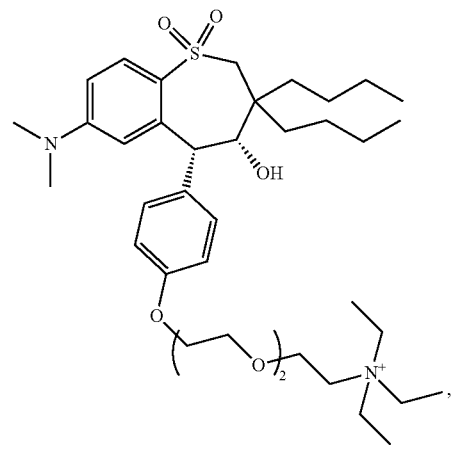

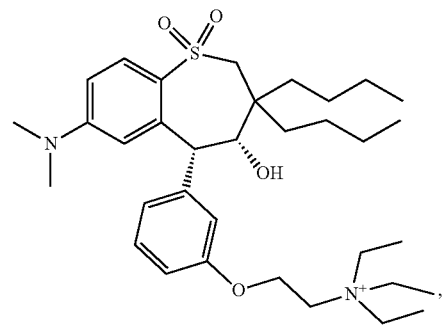

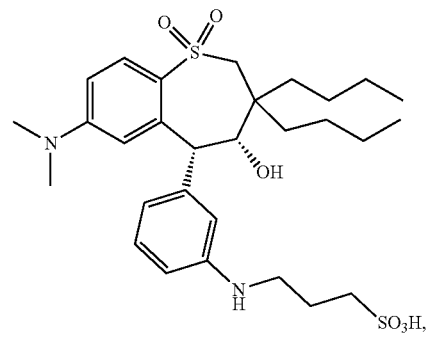

-continued

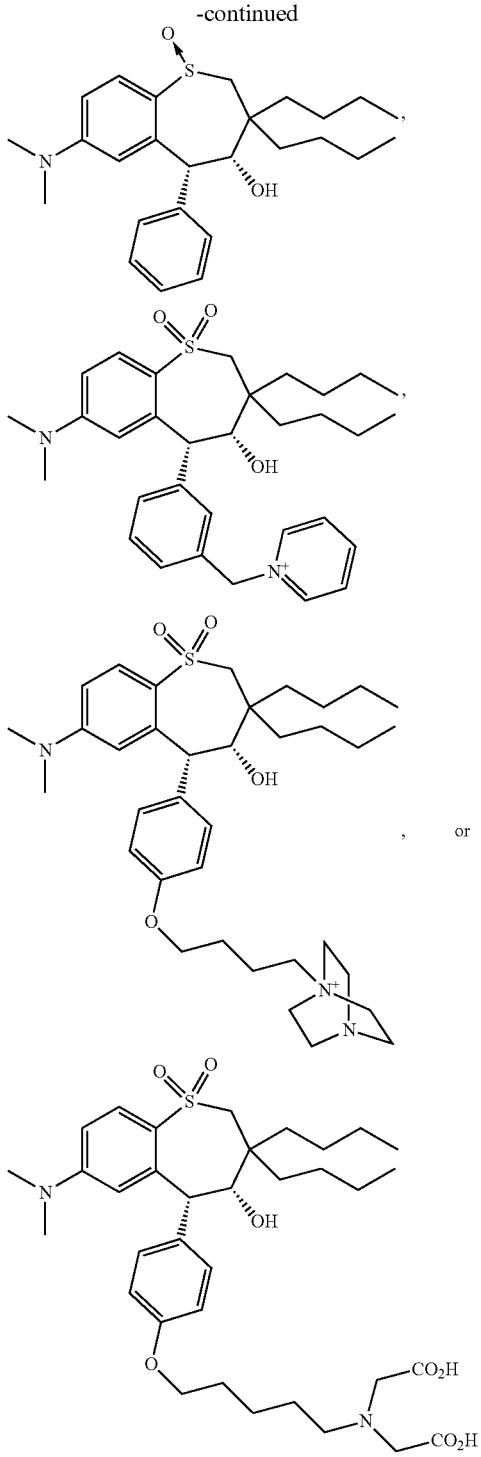

or the like.

In some embodiments of the methods, the compound of Formula II is

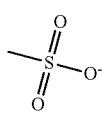

-continued

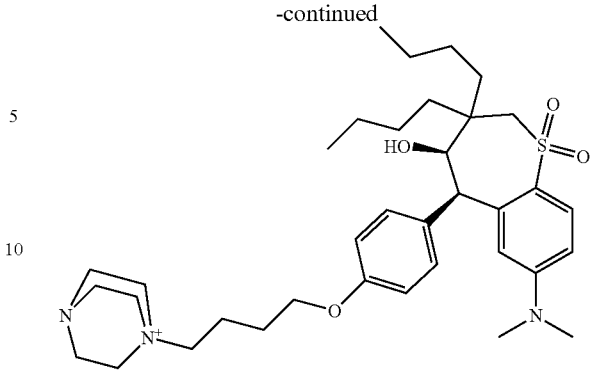

In certain embodiments, ASBTIs suitable for the methods described herein are non-systemic analogs of Compound 100C. Certain compounds provided herein are Compound 100C analogues modified or substituted to comprise a charged group. In specific embodiments, the Compound 100C analogues are modified or substituted with a charged group that is an ammonium group (e.g., a cyclic ar acyclic ammonium group). In certain embodiments, the ammonium group is a non-protic ammonium group that contains a quarternary nitrogen.

In some embodiments, an ASBTI suitable for the methods described herein is a compound of Formula III:

Formula III $$R^7\text{-N}\diagdown\diagup\text{N-}R^6$$

wherein:
each $R^1$, $R^2$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^1$ and $R^2$ together with the nitrogen to which they are attached form a 3-8-membered ring that is optionally substituted with $R^8$;

each $R^3$, $R^4$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

$R^5$ is H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, each $R^6$, $R^7$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^6$ and $R^7$ taken together form a bond;

each X is independently NH, S, or O;

each Y is independently NH, S, or O;

$R^8$ is substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

L is $A_n$, wherein
each A is independently NR$^1$, S(O)$_m$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each m is independently 0-2;
n is 0-7;

K is a moiety that prevents systemic absorption;

provided that at least one of $R^1$, $R^2$, $R^3$ or $R^4$ is -L-K;

or a pharmaceutically acceptable prodrug thereof.

In some embodiments of a compound of Formula III, $R^1$ and $R^3$ are -L-K. In some embodiments, $R^1$, $R^2$ and $R^3$ are -L-K.

In some embodiments, at least one of $R^1$, $R^2$, $R^3$, $R^4$, $R^5$, $R^6$ and $R^7$ is H. In certain embodiments, $R^5$, $R^6$, $R^7$ are H and $R^1$, $R^2$, $R^3$ and $R^4$ are alkyl, aryl, alkyl-aryl, or heteroalkyl. In some embodiments, $R^1$ and $R^2$ are H. In some embodiments, R, $R^2$, $R^5$, $R^6$ and $R^7$ are H. In some embodiments, $R^6$ and $R^7$ together form a bond. In certain embodiments, $R^5$, $R^6$ and $R^7$ are H, alkyl or O-alkyl.

In some embodiments, $R^1$ and $R^3$ are -L-K. In some embodiments, $R^1$, $R^2$ and $R^3$ are -L-K. In some embodiments, $R^3$ and $R^4$ are -L-K. In some embodiments, $R^1$ and $R^2$ together with the nitrogen to which they are attached form a 3-8 membered ring and the ring is substituted with -L-K. In some embodiments, $R^1$ or $R^2$ or $R^3$ or $R^4$ are aryl optionally substituted with -L-K. In some embodiments, $R^1$ or $R^2$ or $R^3$ or $R^4$ are alkyl optionally substituted with -L-K. In some embodiments, $R^1$ or $R^2$ or $R^3$ or $R^4$ are alky-aryl optionally substituted with -L-K. In some embodiments, $R^1$ or $R^2$ or $R^3$ or $R^4$ are heteroalkyl optionally substituted with -L-K.

In some embodiments, L is a $C_1$-$C_7$alkyl. In some embodiments, L is heteroalkyl. In certain embodiments, L is $C_1$-$C_7$alkyl-aryl. In some embodiments, L is $C_1$-$C_7$alkyl-aryl-$C_1$-$C_7$alkyl.

In certain embodiments, K is a non-protic charged group. In some specific embodiments, each K is a ammonium group. In some embodiments, each K is a cyclic non-protic ammonium group. In some embodiments, each K is an acyclic non-protic ammonium group.

In certain embodiments, each K is a cyclic non-protic ammonium group of structure:

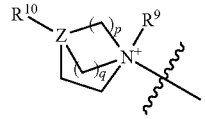

In certain embodiments, K is an acyclic non-protic ammonium group of structure:

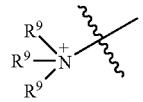

wherein p, q, $R^9$, $R^{10}$ and Z are as defined above. In certain embodiments, p is 1. In other embodiments, p is 2. In further embodiments, p is 3. In some embodiments, q is 0. In other embodiments, q is 1. In some other embodiments, q is 2.

The compounds further comprise 1, 2, 3 or 4 anionic counterions selected from Cl$^-$, Br$^-$, I$^-$, $R^{11}SO_3^-$, ($SO_3^-$—$R^{11}$—$SO_3^-$), $R^{11}CO_2^-$, ($CO_2^-$—$R^{11}$—$CO_2^-$), $(R^{11})_2(P=O)O^-$ and $(R^1)(P=O)O_2^{2-}$ wherein $R^{11}$ is as defined above. In some embodiments, the counterion is Cl$^-$, Br$^-$, I$^-$, $CH_2CO_2^-$, $CH_3SO_3^-$, or $C_6H_5SO_3^-$ or $CO_2^-$—$(CH_2)_2$—$CO_2^-$. In some embodiments, the compound of Formula III has one K group and one counterion. In other embodiments, the compound of Formula III has one K group, and two molecules of the compound of Formula III have one counterion. In yet other embodiments, the compound of Formula III has two K groups and two counterions. In some other embodiments, the compound of Formula III has one K group comprising two ammonium groups and two counterions.

Also described herein are compounds having the Formula IIIA:

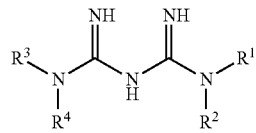

Formula IIIA wherein:
each $R^1$, $R^2$ is independently H, substituted or unsubstituted alkyl, or -L-K; or $R^1$ and $R^2$ together with the nitrogen to which they are attached form a 3-8-membered ring that is optionally substituted with $R^8$;
and $R^3$, $R^4$, $R^8$, L and K are as defined above.

In some embodiments of compounds of Formula IIIA, L is $A_n$, wherein each A is substituted or unsubstituted alkyl, or substituted or unsubstituted heteroalkyl, and n is 0-7. In certain specific embodiments of the compound of Formula IIIA, $R^1$ is H. In some embodiments of Formula IIIA, $R^1$ and $R^2$ together with the nitrogen to which they are attached form a 3-8-membered ring that is optionally substituted with -L-K.

Also described herein are compounds having the Formula IIIB:

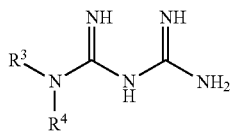

Formula IIIB wherein:
each $R^3$, $R^4$ is independently H, substituted or unsubstituted alkyl, substituted or unsubstituted heteroalkyl, substituted or unsubstituted aryl, substituted or unsubstituted alkyl-aryl, or -L-K;
and $R^1$, $R^2$, L and K are as defined above.

In certain embodiments of Formula IIIB, $R^3$ is H. In certain embodiments, $R^3$ and $R^4$ are each -L-K. In some embodiments, $R^3$ is H and $R^4$ is substituted or unsubstituted alkyl, substituted or unsubstituted heteroalkyl, substituted or unsubstituted aryl, substituted or unsubstituted alkyl-aryl containing one or two -L-K groups.

In some embodiments, an ASBTI suitable for the methods described herein is a compound of Formula IIIC

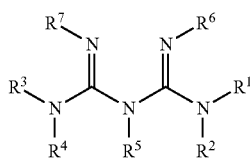

Formula IIIC wherein:
each $R^1$, $R^2$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^1$ and $R^2$ together with the nitrogen to which they are attached form a 3-8-membered ring that is optionally substituted with $R^8$;
each $R^3$, $R^4$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;
$R^5$ is H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, each $R^6$, $R^7$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^6$ and $R^7$ taken together form a bond;

each X is independently NH, S, or O;

each Y is independently NH, S, or O;

$R^8$ is substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

L is $A_n$, wherein
each A is independently $NR^1$, $S(O)_m$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each m is independently 0-2;

n is 0-7;

K is a moiety that prevents systemic absorption;
or a pharmaceutically acceptable salt thereof.

In some specific embodiments of Formula I, II or III, K is selected from

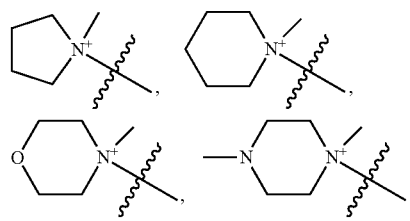

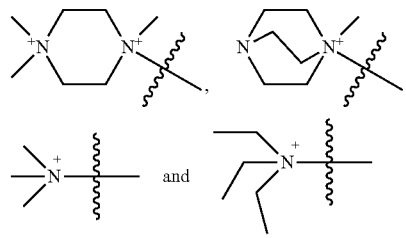

In some embodiments, an ASBTI suitable for the methods described herein is a compound of Formula IV:

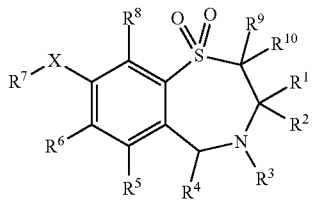

IV wherein
- $R^1$ is a straight chain $C_{1-6}$ alkyl group;
- $R^2$ is a straight chain $C_{1-6}$ alkyl group;
- $R^3$ is hydrogen or a group $OR^{11}$ in which $R^{11}$ is hydrogen, optionally substituted $C_{1-6}$ alkyl or a $C_{1-6}$ alkylcarbonyl group;
- $R^4$ is pyridyl or an optionally substituted phenyl;
- $R^5$, $R^6$ and $R^8$ are the same or different and each is selected from:
  hydrogen, halogen, cyano, $R^{15}$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, $OCF_3$, $OCN$, $SCN$, $NHCN$, $CH_2OR^{15}$, $CHO$, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH=CHR^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$ wherein
- p is an integer from 1-4,
- n is an integer from 0-3 and
- $R^{12}$, $R^{13}$, $R^{14}$ and $R^{15}$ are independently selected from hydrogen and optionally substituted $C^{1-6}$ alkyl;
- $R^7$ is a group of the formula

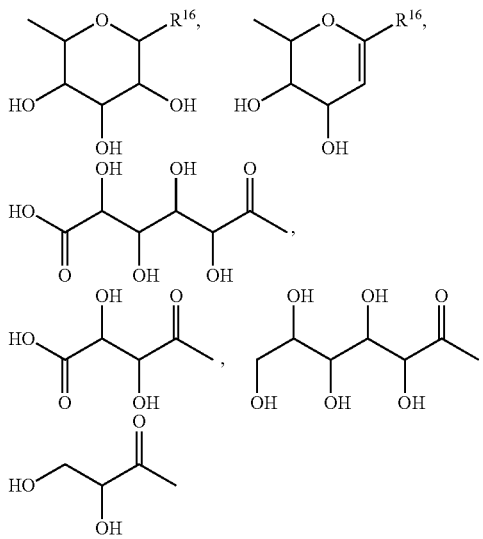

wherein the hydroxyl groups may be substituted by acetyl, benzyl,
or —$(C_1$-$C_6)$-alkyl-$R^{17}$,
wherein the alkyl group may be substituted with one or more hydroxyl groups;
- $R^{16}$ is —COOH, —$CH_2$—OH, —$CH_2$—O-Acetyl, —COOMe or —COOEt;
- $R^{17}$ is H, —OH, —$NH_2$, —COOH or $COOR^{18}$;
- $R^{18}$ is $(C_1$-$C_4)$-alkyl or —NH—$(C_1$-$C_4)$-alkyl;
- X is —NH— or —O—; and $R^9$ and $R^{10}$ are the same or different and each is hydrogen or $C_1$-$C_6$ alkyl; and salts thereof.

In some embodiments, a compound of Formula IV has the structure of Formula IVA or Formula IVB:

Formula IVA

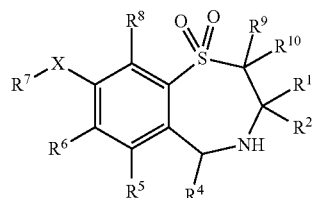

Formula IVB

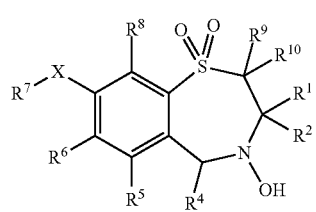

In some embodiments, a compound of Formula IV has the structure of Formula IVC:

IVC

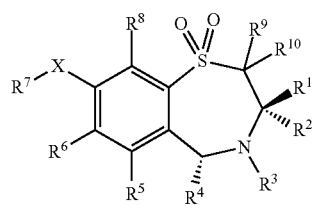

In some embodiments of Formula IV, X is O and $R^7$ is selected from

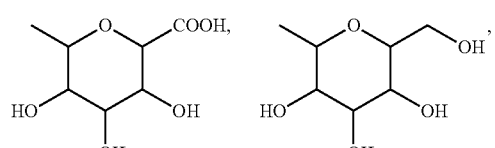

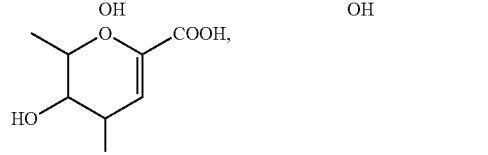

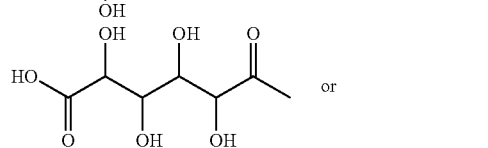

or

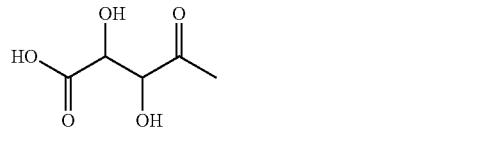

In some embodiments, a compound of Formula IV is:

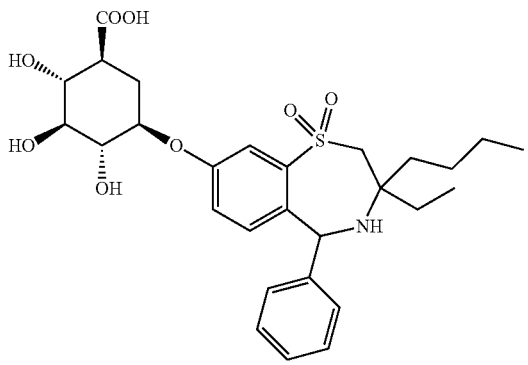 [SMILES: CCCCC1(CC)CS(=O)(=O)c2cc(O[C@@H]3C[C@H](C(=O)O)[C@@H](O)[C@H](O)[C@H]3O)ccc2C(c2ccccc2)N1]

In some embodiments, an ASBTI suitable for the methods described herein is a compound of Formula V:

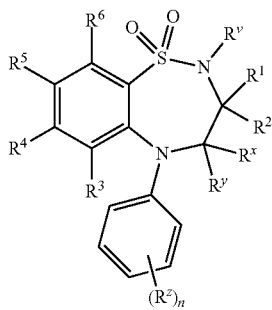

V wherein:
$R^v$ is selected from hydrogen or $C_{1-6}$alkyl;
One of $R^1$ and $R^2$ are selected from hydrogen or $C_{1-6}$alkyl and the other is selected from $C_{1-6}$alkyl;
$R^x$ and $R^y$ are independently selected from hydrogen, hydroxy, amino, mercapto, $C_{1-6}$alkyl, $C_{1-6}$alkoxy, N—($C_{1-6}$alkyl)amino, N,N—($C_{1-6}$alkyl)$_2$amino, $C_{1-6}$alkylS(O)$_a$ wherein a is 0 to 2;
$R^z$ is selected from halo, nitr, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
n is 0-5;
one of $R^4$ and $R^5$ is a group of formula (VA):

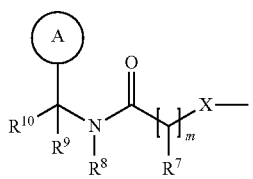

VA $R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
wherein $R^3$ and $R^6$ and the other of $R^4$ and $R^5$ may be optionally substituted on carbon by one or more $R^{17}$;
X is —O—, —N($R^a$)—, —S(O)$_b$— or —CH($R^a$)—;
wherein $R^a$ is hydrogen or $C_{1-6}$alkyl and b is 0-2;
Ring A is aryl or heteroaryl;
wherein Ring A is optionally substituted on carbon by one or more substituents selected from $R^{18}$;
$R^7$ is hydrogen, $C_{1-6}$alkyl, carbocyclyl or heterocyclyl;
wherein $R^7$ is optionally substituted on carbon by one or more substituents selected from $R^{19}$; and wherein if said heterocyclyl contains an —NH— group, that nitrogen may be optionally substituted by a group selected from $R^{20}$;
$R^8$ is hydrogen or $C_{1-6}$-alkyl;
$R^9$ is hydrogen or $C_{1-6}$alkyl;
$R^{10}$ is hydrogen, halo, nitro, cyano, hydroxy, amino, carbamoyl, mercapto, sulphamoyl, hydroxyaminocarbonyl, $C_{1-10}$alkyl, $C_{2-10}$alkynyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)-$R^{21}$—($C_{1-10}$alkylene)$_q$- or heterocyclyl-($C_{1-10}$alkylene)$_r$-$R^{22}$—($C_{1-10}$alkylene)$_s$-; wherein $R^{10}$ is optionally substituted on carbon by one or more substituents selected from $R^{23}$; and wherein if said heterocyclyl contains an —NH— group, that nitrogen may be optionally substituted by a group selected from $R^{24}$; or $R^{10}$ is a group of formula (VB):

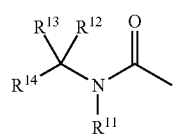

VB wherein:
$R^{11}$ is hydrogen or $C_{1-6}$-alkyl;
$R^{12}$ and $R^{13}$ are independently selected from hydrogen, halo, carbamoyl, sulphamoyl, $C_{1-10}$alkyl, $C_{2-10}$alkynyl, $C_{2-10}$alkynyl, $C_{1-10}$alkanoyl, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl or heterocyclyl; wherein $R^{12}$ and $R^{13}$ may be independently optionally substituted on carbon by one or more substituents selected from $R^{25}$; and wherein if said heterocyclyl contains an —NH— group, that nitrogen may be optionally substituted by a group selected from $R^{26}$;

R¹⁴ is selected from hydrogen, halo, carbamoyl, sulphamoyl, hydroxyaminocarbonyl, $C_{1-10}$alkyl, $C_{2-10}$alkenyl, $C_{2-10}$alkynyl, $C_{1-10}$alkanoyl, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl, carbocyclyl$C_{1-10}$alkyl, heterocyclyl, heterocyclyl$C_{1-10}$alkyl, carbocyclyl-($C_{1-10}$alkylene)-$R^{27}$—($C_{1-10}$alkylene)$_q$- or heterocyclyl-($C_{1-10}$alkylene)$_r$-$R^{28}$—($C_{1-10}$alkylene)$_s$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (VC):

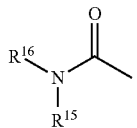

VC $R^{15}$ is hydrogen or $C_{1-6}$alkyl; and $R^{16}$ is hydrogen or $C_{1-6}$alkyl; wherein $R^{16}$ may be optionally substituted on carbon by one or more groups selected from $R^{31}$;

or $R^{15}$ and $R^{16}$ together with the nitrogen to which they are attached form a heterocyclyl; wherein said heterocyclyl may be optionally substituted on carbon by one or more $R^{37}$; and wherein if said heterocyclyl contains an —NH— group, that nitrogen may be optionally substituted by a group selected from $R^{38}$;

m is 1-3; wherein the values of $R^7$ may be the same or different;

$R^{17}$, $R^{18}$, $R^{19}$, $R^{23}$, $R^{25}$, $R^{29}$, $R^{31}$ and $R^{37}$ are independently selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{32}$—($C_{1-10}$alkylene)$_q$- or heterocyclyl-($C_{1-10}$alkylene)$_r$-$R^{33}$—($C_{1-10}$alkylene)$_s$-; wherein $R^{17}$, $R^{18}$, $R^{19}$, $R^{23}$, $R^{25}$, $R^{29}$, $R^{31}$ and $R^{37}$ may be independently optionally substituted on carbon by one or more $R^{34}$; and wherein if said heterocyclyl contains an —NH— group, that nitrogen may be optionally substituted by a group selected from $R^{35}$;

$R^{21}$, $R^{22}$, $R^{27}$, $R^{28}$, $R^{32}$ or $R^{33}$ are independently selected from —O—, —NR$^{36}$—, —S(O)$_x$—, —NR$^{36}$C(O)NR$^{36}$—, —NR$^{36}$C(S)NR$^{36}$—, —OC(O)N=C—, —NR$^{36}$C(O)— or —C(O)NR$^{36}$—; wherein $R^{36}$ is selected from hydrogen or $C_{1-6}$alkyl, and x is 0-2;

p, q, r and s are independently selected from 0-2;

$R^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;

$R^{20}$, $R^{24}$, $R^{26}$, $R^{30}$, $R^{35}$ and $R^{38}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; and wherein a "heteroaryl" is a totally unsaturated, mono or bicyclic ring containing 3-12 atoms of which at least one atom is chosen from nitrogen, sulphur and oxygen, which heteroaryl may, unless otherwise specified, be carbon or nitrogen linked;

wherein a "heterocyclyl" is a saturated, partially saturated or unsaturated, mono or bicyclic ring containing 3-12 atoms of which at least one atom is chosen from nitrogen, sulphur and oxygen, which heterocyclyl may, unless otherwise specified, be carbon or nitrogen linked, wherein a —CH$_2$— group can optionally be replaced by a —C(O)— group, and a ring sulphur atom may be optionally oxidised to form an S-oxide; and wherein a "carbocyclyl" is a saturated, partially saturated or unsaturated, mono or bicyclic carbon ring that contains 3-12 atoms; wherein a —CH$_2$— group can optionally be replaced by a —C(O) group;

or a pharmaceutically acceptable salt or in vivo hydrolysable ester or amide formed on an available carboxy or hydroxy group thereof.

In some embodiments, an ASBTI suitable for the methods described herein is a compound of Formula VI:

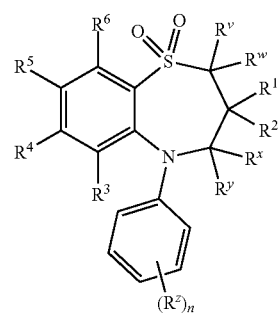

VI wherein:

$R^v$ and $R^w$ are independently selected from hydrogen or $C_{1-6}$alkyl;

one of $R^1$ and $R^2$ is selected from hydrogen or $C_{1-6}$alkyl and the other is selected from $C_{1-6}$alkyl;

$R^x$ and $R^y$ are independently selected from hydrogen or $C_{1-6}$alkyl, or one of $R^x$ and $R^y$ is hydrogen or $C_{1-6}$alkyl and the other is hydroxy or $C_{1-6}$alkoxy;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;

n is 0-5;

one of $R^4$ and $R^5$ is a group of formula (VIA):

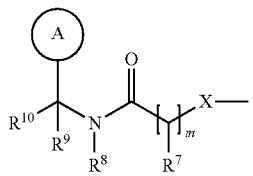

VIA $R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
wherein $R^3$ and $R^6$ and the other of $R^4$ and $R^5$ may be optionally substituted on carbon by one or more $R^{17}$;
X is —O—, —N($R^a$)—, —S(O)$_b$— or —CH($R^a$)—; wherein $R^a$ is hydrogen or $C_{1-6}$alkyl and b is 0-2;
Ring A is aryl or heteroaryl; wherein Ring A is optionally substituted on carbon by one or more substituents selected from $R^{18}$;
$R^7$ is hydrogen, $C_{1-6}$alkyl, carbocyclyl or heterocyclyl; wherein $R^7$ is optionally substituted on carbon by one or more substituents selected from $R^{19}$; and wherein if said heterocyclyl contains an —NH— group, that nitrogen may be optionally substituted by a group selected from $R^{20}$;
$R^8$ is hydrogen or $C_{1-6}$alkyl;
$R^9$ is hydrogen or $C_{1-6}$alkyl;
$R^{10}$ is hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)-$R^{21}$—($C_{1-10}$alkylene)$_q$- or heterocyclyl-($C_{1-10}$alkylene)$_r$-$R^{22}$—($C_{1-10}$alkylene)$_s$-; wherein $R^{10}$ is optionally substituted on carbon by one or more substituents selected from $R^{23}$; and wherein if said heterocyclyl contains an —NH— group, that nitrogen may be optionally substituted by a group selected from $R^{24}$;
or $R^{10}$ is a group of formula (VIB):

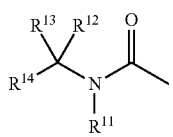

VIB wherein:
$R^{11}$ is hydrogen or $C_{1-6}$alkyl;
$R^{12}$ and $R^{13}$ are independently selected from hydrogen, halo, nitro, cyano, hydroxy, amino, carbamoyl, mercapto, sulphamoyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl or heterocyclyl; wherein $R^{12}$ and $R^{13}$ may be independently optionally substituted on carbon by one or more substituents selected from $R^{25}$; and wherein if said heterocyclyl contains an —NH— group, that nitrogen may be optionally substituted by a group selected from $R^{26}$;
$R^{14}$ is selected from hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{27}$—($C_{1-10}$alkylene)$_q$- or heterocyclyl-($C_{1-10}$alkylene)$_r$-$R^{28}$—($C_{1-10}$alkylene)$_s$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (VIC):

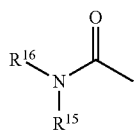

VIC $R^{15}$ is hydrogen or $C_{1-6}$alkyl;
$R^{16}$ is hydrogen or $C_{1-6}$alkyl; wherein $R^{16}$ may be optionally substituted on carbon by one or more groups selected from $R^{31}$;
n is 1-3; wherein the values of $R^7$ may be the same or different;
$R^{17}$, $R^{18}$, $R^{19}$, $R^{23}$, $R^{25}$, $R^{29}$ or $R^{31}$ are independently selected from halo, nitro, cyano, hydroxy, amino, carbamoyl, mercapto, sulphamoyl, hydroxyaminocarbonyl, amidino, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, ($C_{1-10}$alkyl)$_3$silyl, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{32}$—($C_{1-10}$alkylene)$_q$- or heterocyclyl-($C_{1-10}$alkylene)$_r$-$R^{33}$—($C_{1-10}$alkylene)$_s$-; wherein $R^{17}$, $R^{18}$, $R^{19}$, $R^{23}$, $R^{25}$, $R^{29}$ or $R^{31}$ may be independently optionally substituted on carbon by one or more $R^{34}$; and wherein if said heterocyclyl contains an —NH— group, that nitrogen may be optionally substituted by a group selected from $R^{35}$;
$R^{21}$, $R^{22}$, $R^{27}$, $R^{28}$, $R^{32}$ or $R^{33}$ are independently selected from —O—, —NR$^{36}$—, S(O)$_x$—, —NR$^{36}$C(O)NR$^{36}$—, —NR³⁶C(S)NR³⁶—, —OC(O)N=C—, —NR³⁶C(O)— or —C(O)NR³⁶—; wherein R³⁶ is selected from hydrogen or C$_{1-6}$alkyl, and x is 0-2;

p, q, r and s are independently selected from 0-2;

R³⁴ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;

R²⁰, R²⁴, R²⁶, R³⁰ or R³⁵ are independently selected from C$_{1-6}$alkyl, C$_{1-6}$alkanoyl, C$_{1-6}$alkylsulphonyl, C$_{1-6}$alkoxycarbonyl, carbamoyl, N—(C$_{1-6}$alkyl)carbamoyl, N,N—(C$_{1-6}$alkyl)carbamoyl, benzyl, benzyloxycarbonyl, benzoyl and phenylsulphonyl; or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

In some embodiments, a compound of Formula VI has the structure of Formula VID:

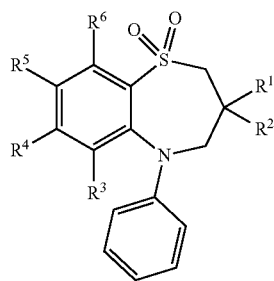

VID wherein:

R¹ and R² are independently selected from C$_{1-6}$alkyl; one of R⁴ and R⁵ is a group of formula (VIE):

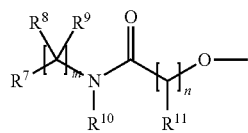

VIE

R³ and R⁶ and the other of R⁴ and R⁵ are independently selected from hydrogen, halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulphamoyl and N,N—(C$_{1-4}$alkyl)$_2$sulphamoyl; wherein R³ and R⁶ and the other of R⁴ and R⁵ may be optionally substituted on carbon by one or more R¹⁴;

R⁷ is carboxy, sulpho, sulphino, phosphono, —P(O)(OR$^a$)(OR$^b$), P(O)(OH)(OR$_a$), —P(O)(OH)(R$^a$) or P(O)(OR$^a$)(R$^b$), wherein R$^a$ and R$^b$ are independently selected from C$_{1-6}$alkyl; or R⁷ is a group of formula (VIF):

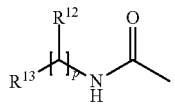

VIF

R⁸ and R⁹ are independently hydrogen, C$_{1-4}$alkyl or a saturated cyclic group, or R⁸ and R⁹ together form C$_{2-6}$alkylene; wherein R⁸ and R⁹ or R⁸ and R⁹ together may be independently optionally substituted on carbon by one or more substituents selected from R¹⁵; and wherein if said saturated cyclic group contains an —NH— moiety, that nitrogen may be optionally substituted by one or more R²⁰;

R¹⁰ is hydrogen or C$_{1-4}$alkyl; wherein R¹⁰ is optionally substituted on carbon by one or more substituents selected from R²⁴;

R¹¹ is hydrogen, C$^{1-4}$alkyl, carbocyclyl or heterocyclyl; wherein R¹¹ is optionally substituted on carbon by one or more substituents selected from R¹⁶; and wherein if said heterocyclyl contains an —NH— moiety, that nitrogen may be optionally substituted by one or more R²¹;

R¹² is hydrogen or C$_{1-4}$alkyl, carbocyclyl or heterocyclyl; wherein R¹² optionally substituted on carbon by one or more substituents selected from R¹⁷; and wherein if said heterocyclyl contains an —NH— moiety, that nitrogen may be optionally substituted by one or more R²²;

R¹³ is carboxy, sulpho, sulphino, phosphono, —P(O)(OR$^c$)(OR$^d$), —P(O)(OH)(OR$^c$), —P(O)(OH)(R$^c$) or —P(O)(OR$^c$)(R$^d$) wherein R$^c$ and R$^d$ are independently selected from C$_{1-6}$alkyl;

m is 1-3; wherein the values of R⁸ and R⁹ may be the same or different;

n is 1-3; wherein the values of R¹¹ may be the same or different;

p is 1-3; wherein the values of R¹² may be the same or different;

R¹⁴ and R¹⁶ are independently selected from halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulphamoyl and N,N—(C$_{1-4}$alkyl)$_2$sulphamoyl; wherein R¹⁴ and R¹⁶ may be independently optionally substituted on carbon by one or more R¹⁸;

R¹⁵ and R¹⁷ are independently selected from halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulphamoyl and N,N—(C$_{1-4}$alkyl)$_2$sulphamoyl, carbocyclyl, heterocyclyl, sulpho, sulphino, amidino, phosphono, —P(O)(OR$^e$)(OR$^f$), —P(O)(OH)(OR$^e$), —P(O)(OH)(R$^e$) or —P(O)(OR$^e$)(R$^f$), wherein R$^e$ and R$^f$ are independently selected from C$_{1-6}$alkyl; wherein R¹⁵ and R¹⁷ may be independently optionally substituted on carbon by one or more R¹⁹; and wherein if said heterocyclyl contains an —NH— moiety, that nitrogen may be optionally substituted by one or more R²³

R¹⁸, R¹⁹ and R²⁵ are independently selected from halo, hydroxy, cyano, carbamoyl, ureido amino nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{20}$, $R^{21}$, $R^{22}$, $R^{23}$ and $R^{26}$ are independently $C_{1-4}$alkyl, $C_{1-4}$alkanoyl, $C_{1-4}$alkylsulphonyl, sulphamoyl, N—($C_{1-4}$alkyl)sulphamoyl, N,N—($C_{1-4}$alkyl)$_2$sulphamoyl, $C_{1-4}$alkoxycarbonyl, carbamoyl, N—($C_{1-4}$alkyl)carbamoyl, N,N—($C_{1-4}$alkyl)$_2$carbamoyl, benzyl, phenethyl, benzoyl, phenylsulphonyl and phenyl;

$R^{24}$ is selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl, carbocyclyl, heterocyclyl; wherein $R^{24}$ may be independently optionally substituted on carbon by one or more $R^{25}$; and wherein if said heterocyclyl contains an —NH— moiety, that nitrogen may be optionally substituted by one or more $R^{26}$;

wherein any saturated cyclic group is a totally or partially saturated, mono or bicyclic ring containing 3-12 atoms of which 0-4 atoms are chosen from nitrogen, sulphur or oxygen, which may be carbon or nitrogen linked;

wherein any heterocyclyl is a saturated, partially saturated or unsaturated, mono or bicyclic ring containing 3-12 atoms of which at least one atom is chosen from nitrogen, sulphur or oxygen, which may be carbon or nitrogen linked, wherein a —CH$_2$— group can optionally be replaced by a —C(O)— or a ring sulphur atom may be optionally oxidised to form the S-oxides; and wherein any carbocyclyl is a saturated, partially saturated or unsaturated, mono or bicyclic carbon ring that contains 3-12 atoms, wherein a —CH$_2$— group can optionally be replaced by a —C(O)—;

or a pharmaceutically acceptable salt thereof.

In some embodiments, any compound described herein is covalently conjugated to a bile acid using any suitable method. In some embodiments, compounds described herein are covalently bonded to a cyclodextrin or a biodegradable polymer (e.g., a polysaccharide).

In certain embodiments compounds described herein are not systemically absorbed. Moreover, provided herein are compounds that inhibit bile salt recycling in the gastrointestinal tract of an individual. In certain embodiments, the administration of a therapeutically effective amount of any compound described herein does not result in gastrointestinal disturbance or lactic acidosis in an individual. In certain embodiments, compounds described herein are administered orally. In some embodiments, an ASBTI is released in the distal ileum. An ASBTI compatible with the methods described herein may be a direct inhibitor, an allosteric inhibitor, or a partial inhibitor of the Apical Sodium-dependent Bile acid Transporter.

In certain embodiments, compounds that inhibit ASBT or any recuperative bile acid transporters are compounds that are described in EP1810689, U.S. Pat. Nos. 6,458,851, 7,413,536, US Appl. Publication Nos. 2002/0147184, 2003/0119809, 2003/0149010, 2004/0014806, 2004/0092500, 2004/0180861, 2004/0180860, 2005/0031651, 2006/0069080, 2006/0199797, 2006/0241121, 2007/0065428, 2007/0066644, 2007/0161578, 2007/0197628, 2007/0203183, 2007/0254952, 2008/0070888, 2008/0070892, 2008/0070889, 2008/0070984, 2008/0089858, 2008/0096921, 2008/0161400, 2008/0167356, 2008/0194598, 2008/0255202, 2008/0261990, WO 2002/50027, WO2005/046797, WO2006/017257, WO2006/105913, WO2006/105912, WO2006/116499, WO2006/117076, WO2006/121861, WO2006/122186, WO2006/124713, WO2007/050628, WO2007/101531, WO2007/134862, WO2007/140934, WO2007/140894, WO2008/028590, WO2008/033431, WO2008/033464, WO2008/031501, WO2008/031500, WO2008/033465, WO2008/034534, WO2008/039829, WO2008/064788, WO2008/064789, WO2008/088836, WO2008/104306, WO2008/124505, and WO2008/130616; the compounds described therein that inhibit recuperative bile acid transport are hereby incorporated herein by reference.

In certain embodiments, compounds that inhibit ASBT or any recuperative bile acid transporters are compounds described in WO93/16055, WO94/18183, WO94/18184, WO96/05188, WO96/08484, WO96/16051, WO97/33882, WO98/38182, WO99/35135, WO98/40375, WO99/64409, WO99/64410, WO00/01687, WO00/47568, WO00/61568, DE 19825804, WO00/38725, WO00/38726, WO00/38727 (including those compounds with a 2,3,4,5-tetrahydro-1-benzothiepine 1,1-dioxide structure), WO00/38728, WO01/66533, WO02/50051, EP0864582 (e.g. (3R,5R)-3-butyl-3-ethyl-1,1-dioxido-5-Phenyl-2,3,4,5-tetrahydro-1,4-benzothiazepin-8-yl (β-D-glucopyranosiduronic acid, WO94/24087, WO98/07749, WO98/56757, WO99/32478, WO99/35135, WO00/20392, WO00/20393, WO00/20410, WO00/20437, WO01/34570, WO00/35889, WO01/68637, WO01/68096, WO02/08211, WO03/020710, WO003/022825, WO03/022830, WO03/022286, JP10072371, U.S. Pat. Nos. 5,910,494; 5,723,458; 5,817,652; 5,663,165; 5,998,400; 6,465,451, 5,994,391; 6,107,494; 6,387,924; 6,784,201; 6,875,877; 6,740,663; 6,852,753; 5,070,103, 6,114,322, 6,020,330, 7,179,792, EP251315, EP417725, EP489-423, EP549967, EP573848, EP624593, EP624594, EP624595, EP869121, EP1070703, WO04/005247, compounds disclosed as having IBAT activity in Drugs of the Future, 24, 425-430 (1999), Journal of Medicinal Chemistry, 48, 5837-5852, (2005) and Current Medicinal Chemistry, 13, 997-1016, (2006); the compounds described therein that inhibit recuperative bile acid transport are hereby incorporated herein by reference.

In some embodiments, compounds that inhibit ASBT or any recuperative bile acid transporter are benzothiepines, benzothiazepines (including 1,2-benzothiazepines; 1,4-benzothiazepines; 1,5-benzothiazepines; and/or 1,2,5-benzothiadiazepines). In some embodiments, compounds that inhibit ASBT or any recuperative bile acid transporter include and are not limited to 1,1-Dioxo-3,3-dibutyl-5-phenyl-7-methylthio-8-(N-{(R)-α-[N-(carboxymethyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7- methylthio-8-(N-{(R)-α-[N-((S)-1-carboxypropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-[N-{(R)-α-carboxy4-hydroxybenzyl}carbamoylmethoxy]-2,3,4,5-tetrahydro-1,2,5-benzothiadiazepine; 1,1-dioxo-3,3-dibutyl-5-phenyl-7-methylthio-8-(N-{(R)-α-[N-(carboxymethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N-{(R)-1'-phenyl-1'-[N'-(carboxymethyl) carbamoyl]methyl}carbamoylmethoxy)-2,3,4,5-tetrahydro-1,5-benzothiazepine; 1,1-dioxo-3,3-dibutyl-5-phenyl-7-methylthio-8-(N-{(R)-α-[N'-((S)-1-carboxypropyl)carbamoyl]-4-hydroxybenzyl}carbamoylmethoxy)-2,3,4,5-tetrahydro-1,5-benzothiazepine; 1,1-dioxo-3,3-dibutyl-5-phenyl-7-methylthio-8-(N-{(R)-α-[N'-((S)-1-carboxyethyl)carbamoyl]benzyl}carbamoylmethoxy)-2,3,4,5-tetrahydro-1,5-benzothiazepine; 1,1-dioxo-3,3-dibutyl-5-phenyl-7-methylthio-8-(N-{(R)-α-[N'-(carboxymethyl)carbamoyl]-4-hydroxybenzyl} carbamoylmethoxy)-2,3,4,5-tetrahydro-1,5-benzothiazepine disclosed in WO 03/022286; S-8921 (disclosed in EP597107, WO 93/08155), 264W94 (GSK) disclosed in WO 96/05188; SC-435 (1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methanesulfonate salt), SC-635 (Searle); 2164U90 (3-butyl-3-ethyl-2,3,4,5-tetrahydro-5-phenyl-1,4-benzothiazepine 1,1-dioxide); BARI-1741 (Aventis SA), AZD 7508 (Astra Zeneca); barixibat (11-(D-gluconamido)-N-{2-[(1S,2R,3S)-3-hydroxy-3-phenyl-2-(2-pyridyl)-1-(2-pyridylamino)propyl]phenyl}undecanamide) or the like, or combinations thereof. In some embodiments, an ASBTI is:

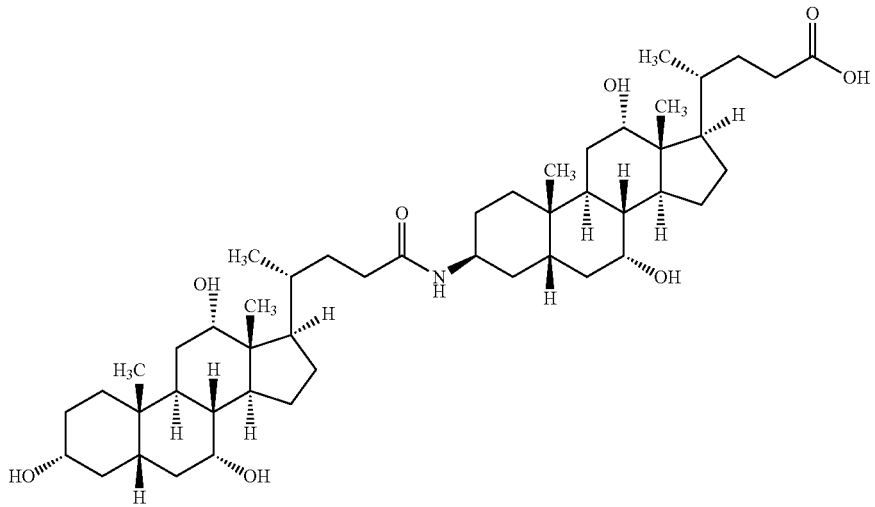

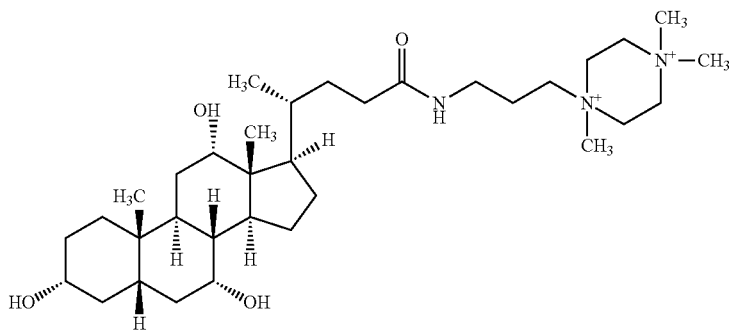

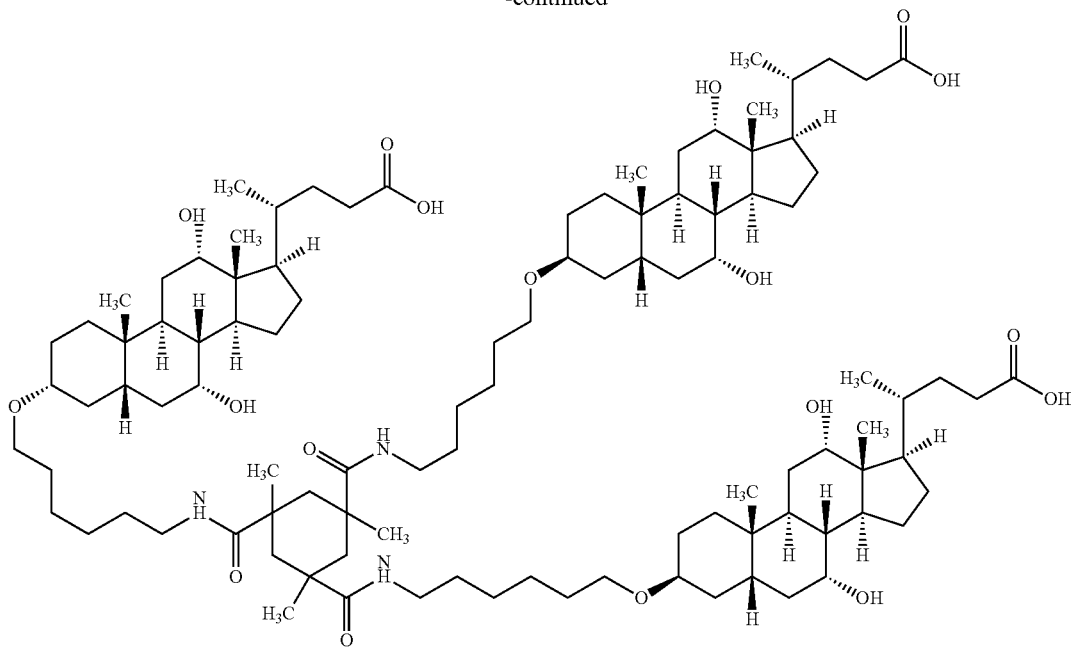
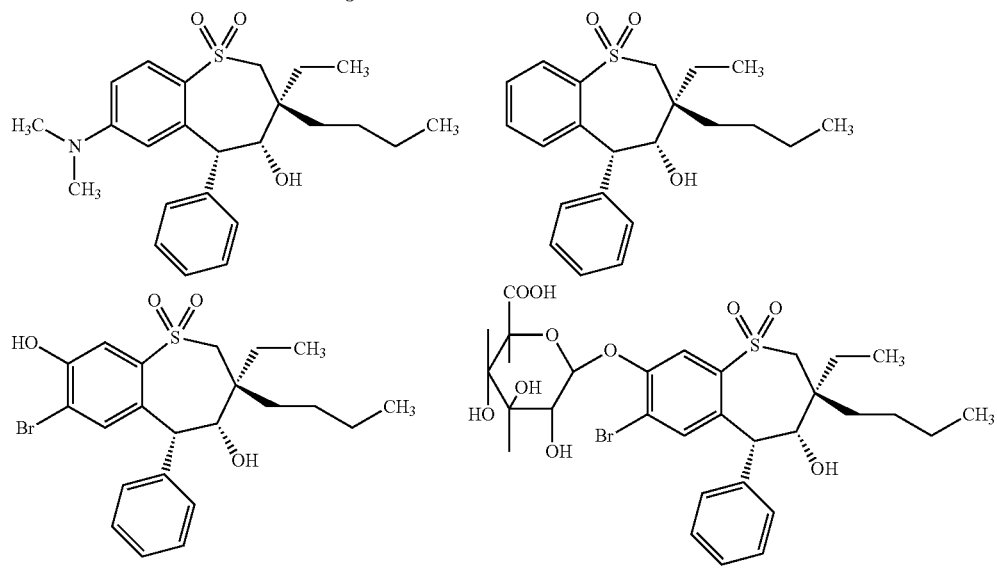
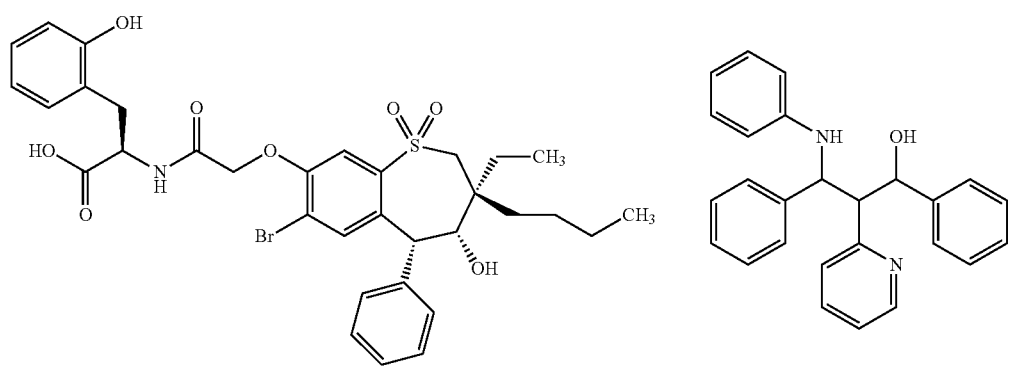

-continued

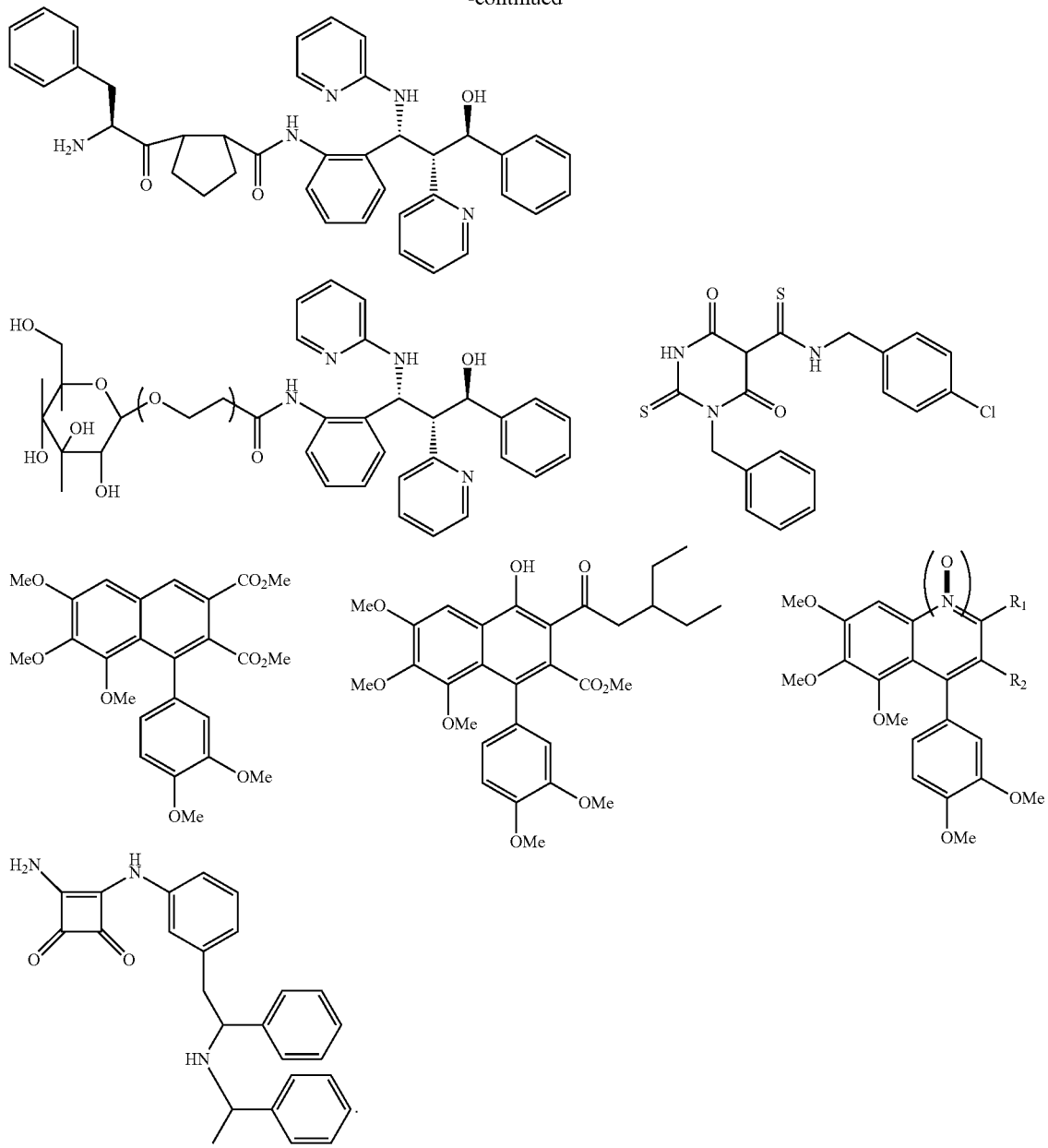

In certain embodiments, compounds described herein have one or more chiral centers. As such, all stereoisomers are envisioned herein. In various embodiments, compounds described herein are present in optically active or racemic forms. It is to be understood that the compounds of the present invention encompasses racemic, optically-active, regioisomeric and stereoisomeric forms, or combinations thereof that possess the therapeutically useful properties described herein. Preparation of optically active forms is achieve in any suitable manner, including by way of non-limiting example, by resolution of the racemic form by recrystallization techniques, by synthesis from optically-active starting materials, by chiral synthesis, or by chromatographic separation using a chiral stationary phase. In some embodiments, mixtures of one or more isomer is utilized as the therapeutic compound described herein. In certain embodiments, compounds described herein contains one or more chiral centers. These compounds are prepared by any means, including enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, chromatography, and the like.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), Mar., ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999) (all of which are incorporated by reference for such disclosure). General methods for the preparation of compound as described herein are modified by the use of appropriate reagents and conditions, for the introduction of the various moieties found in the formulae as provided herein. As a guide the following synthetic methods are utilized.

Formation of Covalent Linkages by Reaction of an Electrophile with a Nucleophile The compounds described herein are modified using various electrophiles and/or nucleophiles to form new functional groups or substituents. Table A entitled "Examples of Covalent Linkages and Precursors Thereof" lists selected non-limiting examples of covalent linkages and precursor functional groups which yield the covalent linkages. Table A is used as guidance toward the variety of electrophiles and nucleophiles combinations available that provide covalent linkages. Precursor functional groups are shown as electrophilic groups and nucleophilic groups.

TABLE A

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it is necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. In some embodiments it is contemplated that each protective group be removable by a different means. Protective groups that are cleaved under totally disparate reaction conditions fulfill the requirement of differential removal.

In some embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In some embodiments carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in then presence of acid- and base-protecting groups since the former are stable and are subsequently removed by metal or pi-acid catalysts. For example, an allyl-blocked carboxylic acid is deprotected with a Pd⁰-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups are selected from:

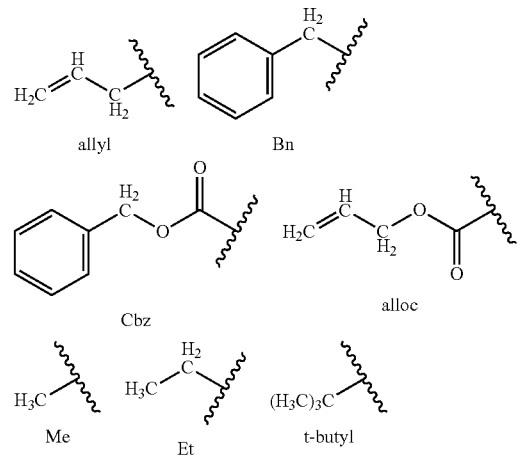

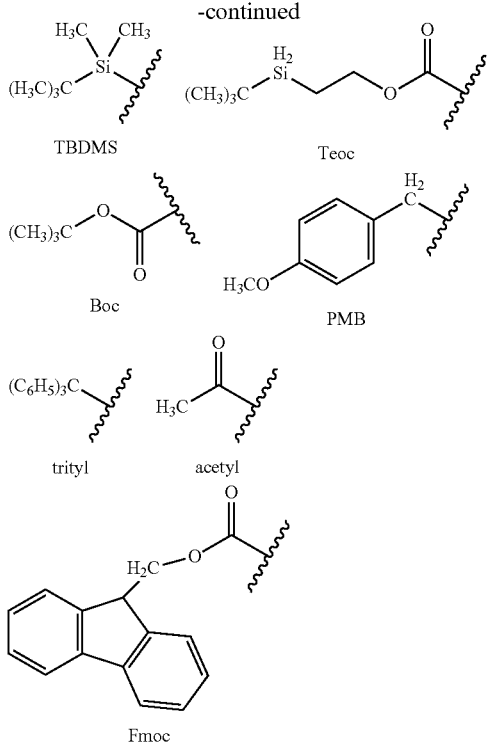

TBDMS

Teoc

Boc

PMB trityl acetyl

Fmoc

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In some embodiments, ASBTIs described herein are synthesized as described in, for example, WO 96/05188, U.S. Pat. Nos. 5,994,391; 7,238,684; 6,906,058; 6,020,330; and 6,114,322. In some embodiments, ASBTIs described herein are synthesized starting from compounds that are available from commercial sources or that are prepared using procedures outlined herein. In some embodiments, compounds described herein are prepared according to the process set forth in Scheme 1:

Scheme 1:

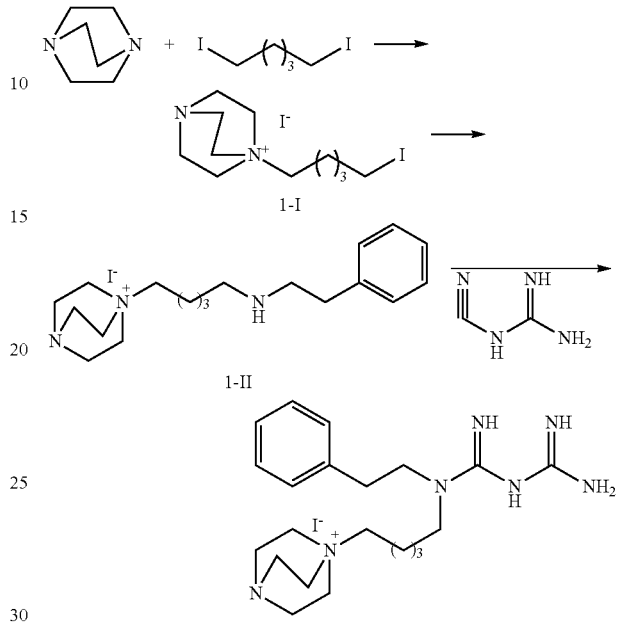

In certain embodiments, the synthesis begins with a reaction of 1,4-diazabicyclo[2.2.2]octane with 4-iodo-1-chloro butane to provide a compound of structure 1-I. Such compounds are prepared in any suitable manner, e.g., as set forth in Tremont, S. J. et. al., *J. Med. Chem.* 2005, 48, 5837-5852. The compound of structure 1-I is then subjected to a reaction with phenethylamine to provide a compound of structure 1-II. The compound of structure 1-II is then allowed to react with dicyanodiamide to provide a compound of Formula I.

In some embodiments, a first compound of Formula III is subjected to a further reaction to provide a second compound of Formula III as shown in Scheme 2 below.

Scheme 2:

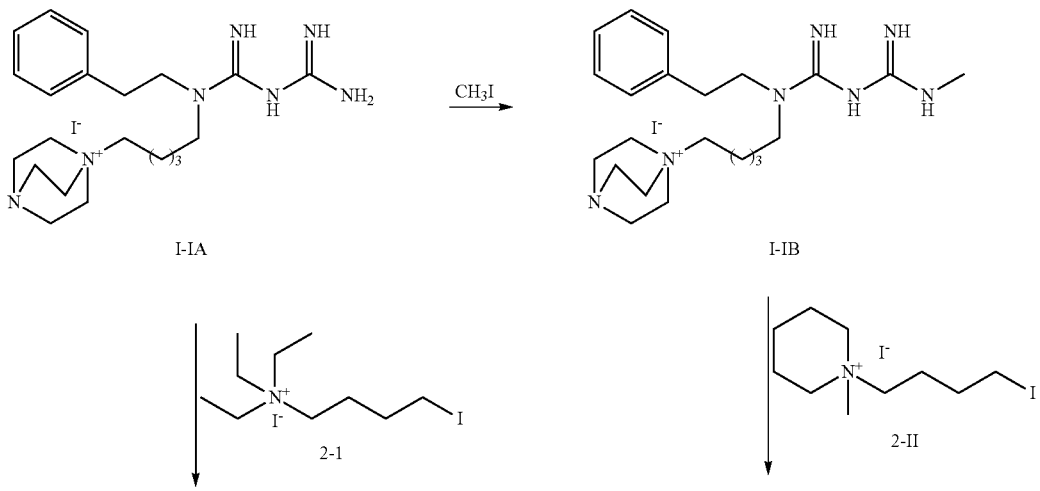

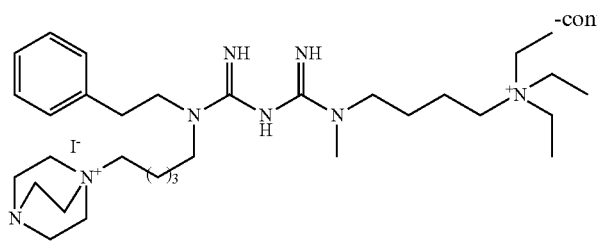

1-IC

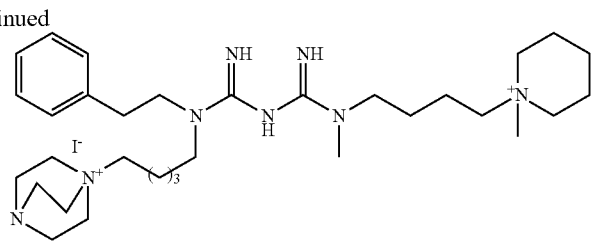

1-ID

A first compound of Formula III, 1-IA, is alkylated with iodomethane to provide a second compound of Formula III, 1-IB. Alkylation of 1-IB with a compound of structure 2-II provides a further compound of Formula III, IC. In an alternative embodiment, a first compound of Formula III, 1-IA, is alkylated with a compound of structure 2-I to provide a second compound of Formula III, 1-IC.

General Definitions

The term "subject", "patient" or "individual" are used interchangeably herein and refer to mammals and non-mammals, e.g., suffering from a disorder described herein. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the patient.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to a patient at risk of developing a particular disease, to a patient reporting one or more of the physiological symptoms of a disease, or to a patient at risk of reoccurrence of the disease.

Where combination treatments or prevention methods are contemplated, it is not intended that the agents described herein be limited by the particular nature of the combination. For example, the agents described herein are optionally administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent. Furthermore, combination treatments are optionally administered separately or concomitantly.

As used herein, the terms "pharmaceutical combination", "administering an additional therapy", "administering an additional therapeutic agent" and the like refer to a pharmaceutical therapy resulting from the mixing or combining of more than one active ingredient and includes both fixed and non-fixed combinations of the active ingredients. The term "fixed combination" means that at least one of the agents described herein, and at least one co-agent, are both administered to a patient simultaneously in the form of a single entity or dosage. The term "non-fixed combination" means that at least one of the agents described herein, and at least one co-agent, are administered to a patient as separate entities either simultaneously, concurrently or sequentially with variable intervening time limits, wherein such administration provides effective levels of the two or more agents in the body of the patient. In some instances, the co-agent is administered once or for a period of time, after which the agent is administered once or over a period of time. In other instances, the co-agent is administered for a period of time, after which, a therapy involving the administration of both the co-agent and the agent are administered. In still other embodiments, the agent is administered once or over a period of time, after which, the co-agent is administered once or over a period of time. These also apply to cocktail therapies, e.g. the administration of three or more active ingredients.

As used herein, the terms "co-administration", "administered in combination with" and their grammatical equivalents are meant to encompass administration of the selected therapeutic agents to a single patient, and are intended to include treatment regimens in which the agents are administered by the same or different route of administration or at the same or different times. In some embodiments the agents described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the agents described herein and the other agent(s) are administered in a single composition. In some embodiments, the agents described herein and the other agent(s) are admixed in the composition.

The terms "effective amount" or "therapeutically effective amount" as used herein, refer to a sufficient amount of at least one agent being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The terms "administer," "administering", "administration," and the like, as used herein, refer to the methods that may be used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Administration techniques that are optionally employed with the agents and methods described herein are found in sources e.g., Goodman and Gilman, The Pharmacological Basis of Therapeutics, current ed.; Pergamon; and Remington's, Pharmaceutical *Sciences* (current edition), Mack Publishing Co., Easton, Pa. In certain embodiments, the agents and compositions described herein are administered orally.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "carrier" as used herein, refers to relatively nontoxic chemical agents that, in certain instances, facilitate the incorporation of an agent into cells or tissues.

The term "non-systemic" as used herein refers to low systemic bioavailability of an administered compound. In some instances a non-systemic compound is a compound that is substantially not absorbed systemically. In some embodiments, ASBTI compositions described herein deliver the ASBTI to the distal ileum, colon, and/or rectum and not systemically (e.g., a substantial portion of the ASBTI is not systemically absorbed. In some embodiments, the systemic absorption of a non-systemic compound is <5% of the administered dose. In some embodiments, the systemic absorption of a non-systemic compound is <15% of the administered dose. In some embodiments, the systemic absorption of a non-systemic compound is <25% of the administered dose. In an alternative approach, a non-systemic ASBTI is a compound that has lower systemic bioavailability relative to the systemic bioavailability of a systemic ASBTI (e.g., compound 100A, 100C). In some embodiments, the bioavailability of a non-systemic ASBTI described herein is <30%, <40%, <50%, <60%, or <70% of the bioavailability of a systemic ASBTI (e.g., compound 100A, 100C).

In another alternative approach, the compositions described herein are formulated to deliver <10% of the administered dose of the ASBTI systemically. In some embodiments, the compositions described herein are formulated to deliver <20% of the administered dose of the ASBTI systemically. In some embodiments, the compositions described herein are formulated to deliver <30% of the administered dose of the ASBTI systemically. In some embodiments, the compositions described herein are formulated to deliver <40% of the administered dose of the ASBTI systemically. In some embodiments, the compositions described herein are formulated to deliver <50% of the administered dose of the ASBTI systemically. In some embodiments, the compositions described herein are formulated to deliver <60% of the administered dose of the ASBTI systemically. In some embodiments, the compositions described herein are formulated to deliver <70% of the administered dose of the ASBTI systemically. In some embodiments, systemic absorption is determined in any suitable manner, including the total circulating amount, the amount cleared after administration, or the like.

The term "ASBT inhibitor" refers to a compound that inhibits apical sodium-dependent bile transport or any recuperative bile salt transport. The term Apical Sodium-dependent Bile Transporter (ASBT) is used interchangeably with the term Ileal Bile Acid Transporter (IBAT).

The term "reducing food intake" refers to consumption of a lower amount of food by an individual undergoing therapy with any ASBTI described herein compared to the amount of food consumed in the absence of ASBTI therapy.

The term "induction of satiety" or "inducing satiety" or "satiety" refers to a feeling of fullness and/or a reduction of the sensation of hunger.

The term "metabolic disorder" refers to any disorder that involves an alteration in the normal metabolism of carbohydrates, lipids, proteins, nucleic acids or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, GLP-2, oxyntomodulin, PYY or the like), the neural control system (e.g., GLP-1 in the brain) or the like. Examples of metabolic disorders include and are not limited to diabetes, insulin resistance, dyslipidemia, metabolic syndrome, or the like.

The term "enhancing enteroendocrine peptide secretion" refers to a sufficient increase in the level of the enteroendocrine peptide agent to, for example, decrease hunger in a subject, to curb appetite in a subject and/or decrease the food intake of a subject or individual and/or treat any disease or disorder described herein. In some embodiments, enhanced enteroendocrine peptide secretion reverses or alleviates symptoms of congestive heart failure, ventricular dysfunction, toxic hypervolemia, polycystic ovary syndrome, inflammatory bowel disease, impaired bowel integrity, short bowel syndrome, gastritis, peptic ulcer, or irritable bowel syndrome.

In various embodiments, pharmaceutically acceptable salts described herein include, by way of non-limiting example, a nitrate, chloride, bromide, phosphate, sulfate, acetate, hexafluorophosphate, citrate, gluconate, benzoate, propionate, butyrate, sulfosalicylate, maleate, laurate, malate, fumarate, succinate, tartrate, amsonate, pamoate, p-tolunenesulfonate, mesylate and the like. Furthermore, pharmaceutically acceptable salts include, by way of non-limiting example, alkaline earth metal salts (e.g., calcium or magnesium), alkali metal salts (e.g., sodium-dependent or potassium), ammonium salts and the like.

The term "optionally substituted" or "substituted" means that the referenced group substituted with one or more additional group(s). In certain embodiments, the one or more additional group(s) are individually and independently selected from amide, ester, alkyl, cycloalkyl, heteroalkyl, aryl, heteroaryl, heteroalicyclic, hydroxy, alkoxy, aryloxy, alkylthio, arylthio, alkylsulfoxide, arylsulfoxide, ester, alkylsulfone, arylsulfone, cyano, halo, alkoyl, alkoyloxo, isocyanato, thiocyanato, isothiocyanato, nitro, haloalkyl, haloalkoxy, fluoroalkyl, amino, alkyl-amino, dialkyl-amino, amido.

An "alkyl" group refers to an aliphatic hydrocarbon group. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, iso-propyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. A "lower alkyl" is a $C_1$-$C_6$alkyl. A "heteroalkyl" group substitutes any one of the carbons of the alkyl group with a heteroatom having the appropriate number of hydrogen atoms attached (e.g., a $CH_2$ group to an NH group or an O group).

An "alkoxy" group refers to a (alkyl)O— group, where alkyl is as defined herein.

The term "alkylamine" refers to the —N(alkyl)$_x$H$_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

An "amide" is a chemical moiety with formula —C(O)NHR or —NHC(O)R, where R is selected from alkyl, cycloalkyl, aryl, heteroaryl (bonded through a ring carbon) and heteroalicyclic (bonded through a ring carbon).

The term "ester" refers to a chemical moiety with formula —C(=O)OR, where R is selected from the group consisting of alkyl, cycloalkyl, aryl, heteroaryl and heteroalicyclic.

As used herein, the term "aryl" refers to an aromatic ring wherein each of the atoms forming the ring is a carbon atom. Aryl rings described herein include rings having five, six, seven, eight, nine, or more than nine carbon atoms. Aryl groups are optionally substituted. Examples of aryl groups include, but are not limited to phenyl, and naphthalenyl.

The term "cycloalkyl" refers to a monocyclic or polycyclic non-aromatic radical, wherein each of the atoms forming the ring (i.e. skeletal atoms) is a carbon atom. In various embodiments, cycloalkyls are saturated, or partially unsaturated. In some embodiments, cycloalkyls are fused with an aromatic ring. Cycloalkyl groups include groups having from 3 to 10 ring atoms. Illustrative examples of cycloalkyl groups include, but are not limited to, the following moieties:

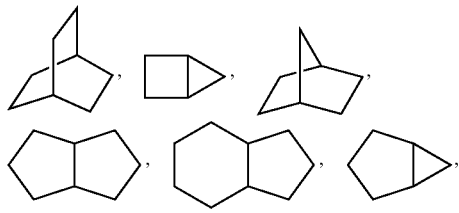

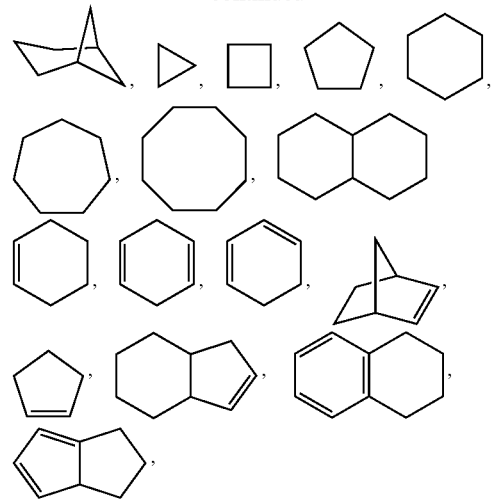

and the like. Monocyclic cycloalkyls include, but are not limited to, cyclopropyl, cyclobutyl, cyclopentyl, cyclohexyl, cycloheptyl, and cyclooctyl.

The term "heterocyclo" refers to heteroaromatic and heteroalicyclic groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In certain embodiments, heteroaryl groups are monocyclic or polycyclic. Illustrative examples of heteroaryl groups include the following moieties:

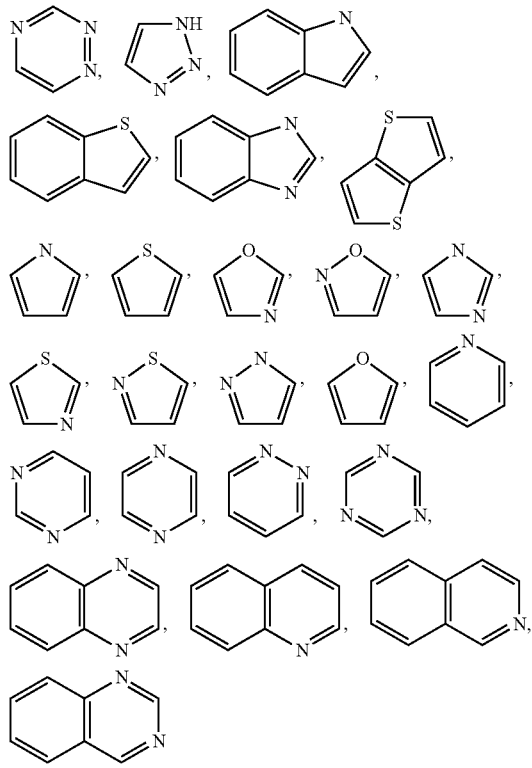

and the like.

A "heteroalicyclic" group or "heterocyclo" group refers to a cycloalkyl group, wherein at least one skeletal ring atom is a heteroatom selected from nitrogen, oxygen and sulfur. In various embodiments, the radicals are with an aryl or heteroaryl. Illustrative examples of heterocyclo groups, also referred to as non-aromatic heterocycles, include:

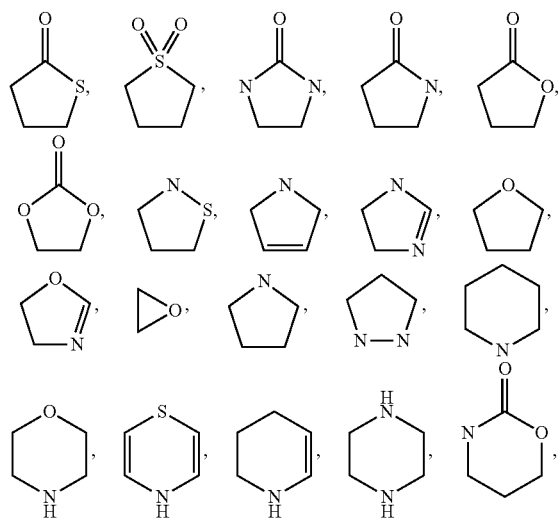

-continued

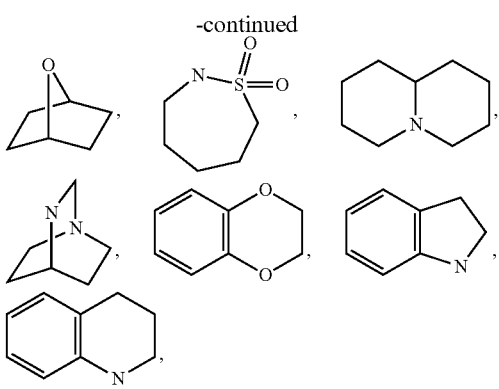

and the like. The term heteroalicyclic also includes all ring forms of the carbohydrates, including but not limited to the monosaccharides, the disaccharides and the oligosaccharides.

The term "halo" or, alternatively, "halogen" means fluoro, chloro, bromo and iodo.

The terms "haloalkyl," and "haloalkoxy" include alkyl and alkoxy structures that are substituted with one or more halogens. In embodiments, where more than one halogen is included in the group, the halogens are the same or they are different. The terms "fluoroalkyl" and "fluoroalkoxy" include haloalkyl and haloalkoxy groups, respectively, in which the halo is fluorine.

The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. In some embodiments, up to two heteroatoms are consecutive, such as, by way of example, —CH$_2$—NH—OCH$_3$ and —CH$_2$—O—Si(CH$_3$)$_3$.

A "cyano" group refers to a —CN group.
An "isocyanato" group refers to a —NCO group.
A "thiocyanato" group refers to a —CNS group.
An "isothiocyanato" group refers to a —NCS group.
"Alkoyloxy" refers to a RC(=O)O— group.
"Alkoyl" refers to a RC(=O)— group.

Methods

Provided herein, in certain embodiments, are methods for treating obesity and/or diabetes comprising administration of a therapeutically effective amount of an ASBTI to an individual in need thereof. Provided herein, in certain embodiments, are methods for treating obesity and/or diabetes comprising contacting the distal gastrointestinal tract, including the distal ileum and/or the colon and/or the rectum, of an individual in need thereof with an ASBTI. Also provided herein are methods for reducing blood or plasma glucose levels of an individual comprising administration of a therapeutically effective amount of an ASBTI to an individual in need thereof. Provided herein are methods for stimulating L-cells in the distal gastrointestinal tract, including L-cells in the distal ileum and/or colon and/or rectum, of an individual comprising administration of a therapeutically effective amount of an ASBTI to an individual in need thereof. Provided herein are methods for enhancing enteroendocrine peptide secretion from L-cells in the distal gastrointestinal tract, including L-cells in the distal ileum and/or colon and/or rectum, of an individual comprising administration of a therapeutically effective amount of an ASBTI to an individual in need thereof. Provided herein are methods for increasing the concentration of bile acids and salts thereof in the vicinity of L-cells lining the distal gastrointestinal tract, including L-cells in the distal ileum, and/or the colon and/or the rectum of an individual, comprising administration of a therapeutically effective amount of an ASBTI to an individual in need thereof. In some of the aforementioned embodiments, the ASBTI is contacted with the distal ileum of the individual in need thereof. In some of the aforementioned embodiments, the ASBTI is not absorbed systemically. In some other embodiments, the ASBTI is absorbed systemically.

In some embodiments of the methods provided herein, inhibition of bile acid transporters and/or bile acid recycling increases the concentration of bile acids in the vicinity of L-cells to concentrations that are higher than physiological levels of bile acids in individuals that have not been treated with an ASBTI. In some embodiments of the methods described herein, an increase in concentration of bile acids in the vicinity of L-cell increases the secretion of enteroendocrine peptides, including GLP-1, GLP-2, PYY and/or oxyntomodulin from L-cells. In some instances a higher concentration of GLP-1 and/or GLP-2 and/or PYY and/or oxynotmodulin in the blood and/or plasma of an individual increases insulin sensitivity of the individual and/or slows down gastric emptying and/or induces a feeling of satiety thereby reducing food intake and/or inducing weight loss.

Provided herein are methods for reducing food intake in an individual comprising administration of a therapeutically effective amount of an ASBTI to an individual in need thereof. In certain embodiments, provided herein is a method for reducing food intake in an individual in need thereof comprising contacting the distal gastrointestinal tract, including the distal ileum and/or colon and/or rectum, of the individual with a therapeutically effective amount of an ASBTI. Provided herein are methods for reducing weight of an individual comprising administration of a therapeutially effective amount of an ASBTI to an individual in need thereof. In certain embodiments, provided herein is a method of reducing weight of an individual in need thereof comprising contacting the distal gastrointestinal tract, including the distal ileum and/or colon and/or rectum, of the individual with a therapeutically effective amount of an ASBT inhibitor. In some embodiments, the method provides for inhibition of bile salt recycling upon administration of any of the compounds described herein to an individual. In some embodiments, an ASBTI described herein is systemically absorbed upon administration. In some embodiments, an ASBTI described herein is not absorbed systemically. In some embodiments, an ASBTI described herein is administered to the individual orally, enterically or rectally. In some embodiments, an ASBTI described herein is delivered and/or released in the distal ileum of an individual. In some embodiments, an ASBTI described herein increases the concentration of bile acids in the distal ileum, the colon and/or the rectum thereby increasing secretion of enteroendocrine peptide products from L-cells in the gastrointestinal tract. In certain instances administration of a therapeutically effective amount of an ASBTI described herein to an individual in need thereof increases the secretion of enteroendocrine peptide products (e.g., GLP-1, GLP-2, PYY, oxytonmodulin or the like) from L-cells that line the gastrointestinal tract. In some embodiments, elevated levels of GLP-1 slow down gastric emptying, and/or inhibit or reduce meal-stimulated gastric secretion, thereby reducing food intake in the individual. In some embodiments, an ASBTI described herein is administered in combination with a DPP-IV inhibitor. In some instances, inhibition of DPP-IV reduces the degradation of enteroendocrine peptide products (e.g. GLP-1) thereby prolonging the delay in gastric emptying and thereby reducing food intake. In some of such embodiments, an ASBTI described herein is administered to a non-diabetic individual for reducing food intake in the non-diabetic individual. In some of such embodiments, an ASBTI described herein is administered to a diabetic individual for reducing food intake in the diabetic individual. In some embodiments, the methods described herein are methods for reducing food intake in obese or morbidly overweight individuals. In some embodiments, a reduction in food intake reduces the weight of an individual (e.g., an obese or morbidly overweight individual)

Provided herein are methods for inducing satiety in an individual comprising administration of a therapeutially effective amount of an ASBTI to an individual in need thereof. In certain embodiments, provided herein is a method for inducing satiety in an individual in need thereof comprising contacting the distal gastrointestinal tract, including distal ileum and/or the colon and/or the rectum, of the individual with a therapeutically effective amount of an ASBT inhibitor. In some embodiments, the method provides for inhibition of bile salt recycling upon administration of any of the compounds described herein to an individual. In some embodiments, an ASBTI described herein is systemically absorbed upon administration. In some embodiments, an ASBTI described herein (e.g., a compound of Formula I) is not absorbed systemically. In some embodiments, an ASBTI described herein is administered to the individual orally, enterically or rectally. In some embodiments, an ASBTI described herein is delivered and/or released in the distal ileum of an individual. In some embodiments, an ASBTI described herein increases the concentration of bile acids in the distal ileum, the colon and/or the rectum and induces secretion of enteroendocrine peptide products from L-cells of the distal gastrointestinal tract. In certain instances administration of a therapeutically effective amount of an ASBTI described herein to an individual in need thereof increases the secretion of enteroendocrine peptide products (e.g., GLP-1, GLP-2, PYY, oxytonmodulin or the like) from L-cells that line the gastrointestinal tract. In some embodiments, elevated levels of GLP-1 slow down gastric emptying, and induce a feeling of fullness in an individual. In some embodiments, an ASBTI described herein is administered in combination with a DPP-IV inhibitor. In some instances, inhibition of DPP-IV reduces the degradation of enteroendocrine peptide products (e.g. GLP-1) thereby prolonging the delay in gastric emptying and sustaining the feeling of satiety and/or fullness. In some of such embodiments, an ASBTI described herein is administered to a non-diabetic individual. In some of such embodiments, an ASBTI described herein is administered to a diabetic individual. In some of such embodiments, an ASBTI described herein is administered to an obese or morbidly overweight individual.

Provided herein are methods for preventing or treating metabolic disorders in an individual comprising administration of a therapeutically effective amount of an ASBTI to an individual in need thereof. In certain embodiments, provided herein is a method for treating metabolic disorders in an individual in need thereof comprising contacting the distal gastrointestinal tract, including distal ileum and/or the colon and/or the rectum, of the individual with a therapeutically effective amount of an ASBTI. In some embodiments, the method provides for inhibition of bile salt recycling upon administration of any of the compounds described herein to an individual. In some embodiments, an ASBTI described herein is systemically absorbed upon administration. In some embodiments, an ASBTI described herein (e.g., a compound of Formula I) is not absorbed systemically. In some embodiments, an ASBTI described herein is administered to the individual orally, enterically or rectally. In some embodiments, an ASBTI described herein is delivered and/or released in the distal ileum of an individual. In some embodiments, an ASBTI described herein increases the concentration of bile acids in the distal ileum, the colon and/or the rectum and induces secretion of enteroendocrine peptide products from the L-cells of the gastrointestinal tract. In certain instances administration of a therapeutically effective amount of an ASBTI described herein to an individual in need thereof increases the secretion of enteroendocrine peptide products (e.g., GLP-1, GLP-2, PYY, oxytonmodulin or the like) from L-cells that line the distal gastrointestinal tract. In some embodiments, elevated levels of GLP-1 reduce glucose levels in blood. In some instances, elevated levels of GLP-1 increase insulin sensitivity in a hyperglycemic individual. In some embodiments, an ASBTI described herein is administered in combination with a DPP-IV inhibitor. In some instances, inhibition of DPP-IV reduces the degradation of enteroendocrine peptide products (e.g. GLP-1) thereby prolonging the effect of GLP-1 in reducing blood glucose levels. In some of such embodiments, an ASBTI described herein is administered to a non-diabetic individual. In some of such embodiments, an ASBTI described herein is administered to a diabetic individual. In some of such embodiments, an ASBTI described herein is administered to an obese or morbidly overweight individual.

Provided herein are methods for preventing or treating radiation induced enteritis in an individual comprising administration of a therapeutially effective amount of an ASBTI to an individual in need thereof. In certain embodiments, provided herein is a method for treating radiation enteritis in an individual in need thereof comprising contacting the distal gastrointestinal tract, including distal ileum and/or the colon and/or the rectum, of the individual with a therapeutically effective amount of an ASBTI. In some embodiments, the method provides for inhibition of bile salt recycling upon administration of any of the compounds described herein to an individual. In some embodiments, an ASBTI described herein is systemically absorbed upon administration. In some embodiments, an ASBTI described herein (e.g., a compound of Formula I) is not absorbed systemically. In some embodiments, an ASBTI described herein is administered to the individual orally, enterically or rectally. In some embodiments, an ASBTI described herein is delivered and/or released in the distal ileum of an individual. In some embodiments, an ASBTI described herein increases the concentration of bile acids in the distal ileum, the colon and/or the rectum and induces secretion of enteroendocrine peptide products from the L-cells of the gastrointestinal tract. In certain instances administration of a therapeutically effective amount of an ASBTI described herein to an individual in need thereof increases the secretion of enteroendocrine peptide products (e.g., GLP-1, GLP-2, PYY, oxytonmodulin or the like) from L-cells that line the distal gastrointestinal tract. In some embodiments, elevated levels of GLP-2 has a regenerative effect on radiation-induced injuries of the gastrointestinal tract (e.g., after radiation therapy for treatment of cancer, or accidental exposure to radiation). In some embodiments, prophylactic administration of an ASBTI reduces or prevents intestinal inflammation (gastrointestinal enteritis), for example in a cancer patient undergoing radiation therapy. In some embodiments, an ASBTI described herein is administered in combination with a DPP-IV inhibitor. In some instances, inhibition of DPP-IV reduces the degradation of enteroendocrine peptide products (e.g. GLP-2) thereby prolonging the effect of GLP-2 in regeneration and/or healing of gastrointestinal tissue.

In some embodiments, administration of an ASBT inhibitor described herein allows for treatment of a metabolic disorder without the side effects associated with conventional therapies (e.g., biguanides such as metformin, DDPIV inhibitors or the like) for metabolic disorders. In some embodiments, the administration of an ASBT inhibitor described herein reduces the incidence of gastrointestinal distress and/or lactic acidosis that is associated with biguanide therapy and/or treatment with a DPP-IV inhibitor. In some embodiments, the administration of an ASBT inhibitor described herein avoids weight gain that is associated with biguanide therapy and/or treatment with a DPP-IV inhibitor and/or a TGR5 agonist. Metabolic disorders that are amenable to treatment with compounds described herein include diabetes, insulin resistance, and metabolic syndrome.

In some embodiments, provided herein is a method of decreasing the dose of a biguanide or a DPP-IV inhibitor to treat a metabolic disorder in an individual in need thereof by replacing treatment with a biguanide (e.g., metformin) or a DPP-IV inhibitor with a treatment comprising administering a therapeutically effective amount of an ASBT inhibitor described herein to the individual. In some embodiments, provided herein is a method for treating a metabolic disease or disorder comprising administering to an individual in need thereof a therapeutically effective amount of an ASBT inhibitor described herein in combination with a reduced dose of a biguanide (e.g., metformin) or a DPP-IV inhibitor (e.g., sitagliptin) or a TGR5 agonist.

In some embodiments of any of the methods described herein, administration of an ASBT inhibitor described herein increases the level of GLP-1 in the blood and/or plasma of an individual by from about 1.1 times to about 30 times compared to the level of GLP-1 in the blood and/or plasma of the individual prior to administration of the ASBTI. In some embodiments of any of the methods described herein, administration of an ASBT inhibitor described herein increases the level of GLP-1 in the blood and/or plasma of an individual by from about 1.1 times to about 20 times compared to the level of GLP-1 in the blood and/or plasma of the individual prior to administration of the ASBTI. In some embodiments of any of the methods described herein, administration of an ASBT inhibitor described herein increases the level of GLP-1 in the blood and/or plasma of an individual by from about 1.5 times to about 10 times compared to the level of GLP-1 in the blood and/or plasma of the individual prior to administration of the ASBTI. In some embodiments of any of the methods described herein, administration of an ASBT inhibitor described herein increases the level of GLP-1 in the blood and/or plasma of an individual by from about 2 times to about 8 times compared to the level of GLP-1 in the blood and/or plasma of the individual prior to administration of the ASBTI. In some embodiments of any of the methods described herein, administration of an ASBT inhibitor described herein increases the level of GLP-1 in the blood and/or plasma of an individual by from about 2 times to about 6 times compared to the level of GLP-1 in the blood and/or plasma of the individual prior to administration of the ASBTI. In some instances, an increase in GLP-1 level of from about 2 times to about 3 times following the administration of an ASBT inhibitor described herein compared to the level of GLP-1 in the blood and/or plasma of the individual prior to administration of the ASBTI is associated with an antidiabetic effect. In some instances, an increase in GLP-1 level of from about 3 times to about 8 times following the administration of an ASBT inhibitor described herein compared to the level of GLP-1 in the blood and/or plasma of the individual prior to administration of the ASBTI is associated with reduction in food intake and/or induction of satiety and/or weight loss.

In certain embodiments of any of the methods described herein, administration of an ASBTI reduces blood and/or plasma sugar levels by at least 20%, at least 30%, at least 40%, at least 50% at least 60%, at least 70% or at least 80% compared to blood and/or plasma sugar levels prior to administration of the ASBTI. In some embodiments of any of the methods described herein, administration of an ASBTI reduces blood and/or plasma sugar levels by at least 20% compared to blood and/or plasma sugar levels prior to administration of the ASBTI. In some embodiments of any of the methods described herein, administration of an ASBTI reduces blood and/or plasma sugar levels by at least 30% compared to blood and/or plasma sugar levels prior to administration of the ASBTI. In some embodiments of any of the methods described herein, administration of an ASBTI reduces blood and/or plasma sugar levels by at least 40% compared to blood and/or plasma sugar levels prior to administration of the ASBTI.

In some embodiments of any of the methods described herein, administration of an ASBTI reduces blood and/or plasma sugar levels for a longer period of time (e.g., at least 24 hours) compared to reduction in blood and/or plasma sugar levels upon administration of metformin or a DPP-IV inhibitor. In some embodiments of any of the methods described herein, administration of a single dose of an ASBTI sustains reduced blood and/or plasma sugar levels for at least 6 hours, at least 12 hours, at least 14 hours, at least 16 hours, at least 18 hours, at least 20 hours, at least 24 hours, at least 30 hours, at least 36 hours or at least 48 hours compared to reduction in blood and/or plasma sugar levels upon administration of a single dose of metformin or a DPP-IV inhibitor.

In some embodiments of any of the methods described herein, administration of an ASBTI results in higher levels of GLP-1 in blood and/or plasma of an individual compared to levels of GLP-1 in blood and/or plasma of a normal individual. In some embodiments of any of the methods described herein, administration of an ASBTI results in higher levels of GLP-1 in blood and/or plasma of an individual compared to levels of GLP-1 in blood and/or plasma of an individual that has been administered a DPP-IV inhibitor.

Also provided herein is a method for treating conditions that are ameliorated by increased secretion of L-cell enteroendocrine peptides comprising contacting the distal gastrointestinal tract, including distal ileum and/or the colon and/or the rectum, of an individual in need thereof with a therapeutically effective amount of any ASBTI compound described herein. L-cells are highly specialized gut enteroendocrine cells expressed along the gastrointestinal tract. The majority of L cells are located in the distal gastrointestinal tract, predominantly in the ileum and colon. The L-cells in the enteric endocrine system do not secrete their hormone continuously.

Instead, they respond to changes in the environment within the lumen of the digestive tube, including changes in bile acid concentrations in the lumen of the digestive tube. The apical border of L-cells is in contact with the contents of the gastrointestinal lumen. Enteroendocrine peptides secreted by L-cells include GLP-1, GLP-2, PYY and oxyntomodulin. In certain instances, the methods described herein enhance L-cell secretion of one or more metabolic and/or enteroendocrine hormones. In some embodiments, the methods described herein enhance L-cell secretion of GLP-1, GLP-2, PYY or oxyntomodulin or combinations thereof. In certain embodiments, enhanced secretion of multiple enteroendocrine hormones (e.g., enhanced secretion of PYY and/or GLP-1 and/or GLP-2 and/or oxyntomodulin) is more effective for long term weight reduction compared to enhanced secretion of any single enteroendocrine hormone. In certain embodiments, enhanced secretion of multiple enteroendocrine hormones (e.g., enhanced secretion of PYY and/or GLP-1 and/or GLP-2 and/or oxyntomodulin) is more effective for long term improvement of peripheral insulin sensitivity compared to enhanced secretion of any single enteroendocrine hormone. Thus, advantageously, administration of a single therapeutic agent (e.g., any ASBTI described herein) has the potential to simultaneously impact multiple metabolic pathways (as opposed to administration of multiple therapeutic agents each of which impacts a different metabolic pathway).

In certain instances, contacting the distal ileum of an individual with an ASBTI (e.g., any ASBTI described herein) inhibits bile acid reuptake and increases the concentration of bile acids in the vicinity of L-cells in the distal ileum and/or colon and/or rectum, thereby enhancing the release of enteroendocrine peptides. Bile acids and/or bile salts interact with TGR5 receptors on the apical surface of L-cells to trigger the release of one or more enteroendocrine hormones into systemic circulation and/or the gastrointestinal lumen. Under physiological conditions, the concentration of enteroendocrine hormones varies in the gastrointestinal tract. By way of example, in the absence of an ASBTI, PYY concentrations in the upper small intestine are about ~5 pmol/g tissue, about ~80 pmol/g tissue in the distal ileum and ascending colon, ~200 pmol/g tissue in the sigmoid colon, and ~500 pmol/g tissue in the rectum. In some embodiments, the administration of one or more ASBTIs, according to methods described herein, increases concentrations of one or more enteroendocrine peptides in the gastrointestinal lumen and/or systemic circulation compared to physiological concentrations of the enteroendocrine peptides in the absence of an ASBTI.

Conditions that are mediated by L-cell enteroendocrine peptides include obesity, diabetes, congestive heart failure, ventricular dysfunction, toxic hypervolemia, polycystic ovary syndrome, inflamatory bowel disease, impaired bowel integrity, short bowel syndrome, gastritis, peptic ulcer, irritable bowel disease, gastroesophageal reflux disease (GERD), Barrett's esophagus or the like.

Administration of a compound described herein is achieved in any suitable manner including, by way of non-limiting example, by oral, enteric, parenteral (e.g., intravenous, subcutaneous, intramuscular), intranasal, buccal, topical, rectal, or transdermal administration routes. Any compound or composition described herein is administered prior to ingestion of food, with food or after ingestion of food.

In certain embodiments, a compound or a composition comprising a compound described herein is administered for prophylactic and/or therapeutic treatments. In therapeutic applications, the compositions are administered to an individual already suffering from a disease or condition, in an amount sufficient to cure or at least partially arrest the symptoms of the disease or condition. In various instances, amounts effective for this use depend on the severity and course of the disease or condition, previous therapy, the individual's health status, weight, and response to the drugs, and the judgment of the treating physician.

In prophylactic applications, compounds or compositions containing compounds described herein are administered to an individual susceptible to or otherwise at risk of a particular disease, disorder or condition. In certain embodiments of this use, the precise amounts of compound administered depend on the individual's state of health, weight, and the like. Furthermore, in some instances, when a compound or composition described herein is administered to an individual, effective amounts for this use depend on the severity and course of the disease, disorder or condition, previous therapy, the individual's health status and response to the drugs, and the judgment of the treating physician.

In certain instances, wherein following administration of a selected dose of a compound or composition described herein, an individual's condition does not improve, upon the doctor's discretion the administration of a compound or composition described herein is optionally administered chronically, that is, for an extended period of time, including throughout the duration of the individual's life in order to ameliorate or otherwise control or limit the symptoms of the individual's disorder, disease or condition.

In certain embodiments, an effective amount of a given agent varies depending upon one or more of a number of factors such as the particular compound, disease or condition and its severity, the identity (e.g., weight) of the subject or host in need of treatment, and is determined according to the particular circumstances surrounding the case, including, e.g., the specific agent being administered, the route of administration, the condition being treated, and the subject or host being treated. In some embodiments, doses administered include those up to the maximum tolerable dose. In certain embodiments, about 0.001-5000 mg per day, from about 0.001-1500 mg per day, about 0.001 to about 100 mg/day, about 0.001 to about 50 mg/day, or about 0.001 to about 30 mg/day, or about 0.001 to about 10 mg/day of a compound described herein is administered. In various embodiments, the desired dose is conveniently presented in a single dose or in divided doses administered simultaneously (or over a short period of time) or at appropriate intervals, for example as two, three, four or more sub-doses per day. In various embodiments, a single dose is from about 0.001 mg/kg to about 500 mg/kg. In various embodiments, a single dose is from about 0.001, 0.01, 0.1, 1, or 10 mg/kg to about 10, 50, 100, or 250 mg/kg. In various embodiments, a single dose of an ASBTI is from about 0.001 mg/kg to about 100 mg/kg. In various embodiments, a single dose of an ASBTI is from about 0.001 mg/kg to about 50 mg/kg. In various embodiments, a single dose of an ASBTI is from about 0.001 mg/kg to about 10 mg/kg. In various embodiments, a single dose of an ASBTI is administered every 6 hours, every 12 hours, every 24 hours, every 48 hours, every 72 hours, every 96 hours, every 5 days, every 6 days, or once a week.

In the case wherein the patient's status does improve, upon the doctor's discretion an ASBTI is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred (e.g., weight loss), a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms (e.g., weight gain).

In certain instances, there are a large number of variables in regard to an individual treatment regime, and considerable excursions from these recommended values are considered within the scope described herein. Dosages described herein are optionally altered depending on a number of variables such as, by way of non-limiting example, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are optionally determined by pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. In certain embodiments, data obtained from cell culture assays and animal studies are used in formulating a range of dosage for use in human. In specific embodiments, the dosage of compounds described herein lies within a range of circulating concentrations that include the $ED_{50}$ with minimal toxicity. The dosage optionally varies within this range depending upon the dosage form employed and the route of administration utilized.

In some embodiments, the systemic exposure of a therapeutically effective amount of any non-systemic ASBTI described herein (e.g., an ASBTI that comprises a group L-K) is reduced when compared to the systemic exposure of a therapeutically effective amount of any systemically absorbed ASBTI (e.g. Compounds 100A, 100C). In some embodiments, the AUC of a therapeutically effective amount of any non-systemic ASBTI described herein (e.g., an ASBTI that comprises a group L-K) is at least 10%, at least 20%, at least 30%, at least 40%, at least 50%, at least 60%, at least 70%, at least 80% or at least 90% reduced when compared to the AUC of any systemically absorbed ASBTI (e.g. Compounds 100A, 100C).

In some embodiments, the systemic exposure of a therapeutically effective amount of a compound of Formula I that is not systemically absorbed (e.g., a compound of Formula I that comprises a group L-K) is reduced when compared to the systemic exposure of a therapeutically effective amount of Compound 100A. In some embodiments, the AUC of a therapeutically effective amount of a compound of Formula I that is not systemically absorbed (e.g., a compound of Formula I that comprises a group L-K) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula I that is not systemically absorbed (e.g., a compound of Formula I that comprises a group L-K) is about 50% reduced when compared to the AUC of a therapeutically effective amount of Compound 100A. In other embodiments, the AUC of a therapeutically effective amount of a compound of Formula I that is not systemically absorbed (e.g., a compound of Formula I that comprises a group L-K) is about 75% reduced when compared to the AUC of a therapeutically effective amount of Compound 100A.

In some embodiments, the systemic exposure of a therapeutically effective amount of a compound of Formula II that is not systemically absorbed (e.g., a compound of Formula II that comprises a group L-K) is reduced when compared to the systemic exposure of a therapeutically effective amount of Compound 100A. In some embodiments, the AUC of a therapeutically effective amount of a compound of Formula II that is not systemically absorbed (e.g., a compound of Formula II that comprises a group L-K) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula II that is not systemically absorbed (e.g., a compound of Formula II that comprises a group L-K) is about 50% reduced when compared to the AUC of a therapeutically effective amount of Compound 100A. In other embodiments, the AUC of a therapeutically effective amount of a compound of Formula II that is not systemically absorbed (e.g., a compound of Formula II that comprises a group L-K) is about 75% reduced when compared to the AUC of a therapeutically effective amount of Compound 100A.

In some embodiments, the systemic exposure of a therapeutically effective amount of a compound of Formula III, IIIA, IIIB or IIIC is reduced when compared to the systemic exposure of a therapeutically effective amount of Compound 100C. In some embodiments, the AUC of a therapeutically effective amount of a compound of Formula III, IIIA, IIIB or IIIC is about 10%, about 20%, about 30%, about 40%, about 50%, about 60%, about 70%, about 80% or about 90% reduced when compared to the AUC of a therapeutically effective amount of Compound 100C. In some embodiments, the AUC of a therapeutically effective amount of a compound of Formula III, IIIA, IIIB or IIIC is about 50% reduced when compared to the AUC of a therapeutically effective amount of Compound 100C. In other embodiments, the AUC of a therapeutically effective amount of a compound of Formula III, IIIA, IIIB or IIIC is about 75% reduced when compared to the AUC of a therapeutically effective amount of Compound 100C.

In some embodiments, the systemic exposure of a therapeutically effective amount of a compound of Formula IV that is not systemically absorbed (e.g., a compound of Formula IV that comprises a group L-K) is reduced when compared to the systemic exposure of a therapeutically effective amount of Compound 100A. In some embodiments, the AUC of a therapeutically effective amount of a compound of Formula IV that is not systemically absorbed (e.g., a compound of Formula I that comprises a group L-K) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula IV that is not systemically absorbed (e.g., a compound of Formula IV that comprises a group L-K) is about 50% reduced when compared to the AUC of a therapeutically effective amount of Compound 100A. In other embodiments, the AUC of a therapeutically effective amount of a compound of Formula IV that is not systemically absorbed (e.g., a compound of Formula IV that comprises a group L-K) is about 75% reduced when compared to the AUC of a therapeutically effective amount of Compound 100A.

In some embodiments, the systemic exposure of a therapeutically effective amount of a compound of Formula V that is not systemically absorbed (e.g., a compound of Formula V that comprises a group L-K) is reduced when compared to the systemic exposure of a therapeutically effective amount of Compound 100A. In some embodiments, the AUC of a therapeutically effective amount of a compound of Formula V that is not systemically absorbed (e.g., a compound of Formula V that comprises a group L-K) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula I that is not systemically absorbed (e.g., a compound of Formula V that comprises a group L-K) is about 50% reduced when compared to the AUC of a therapeutically effective amount of Compound 100A. In other embodiments, the AUC of a therapeutically effective amount of a compound of Formula I that is not systemically absorbed (e.g., a compound of Formula V that comprises a group L-K) is about 75% reduced when compared to the AUC of a therapeutically effective amount of Compound 100A.

In some embodiments, the systemic exposure of a therapeutically effective amount of a compound of Formula VI or VID that is not systemically absorbed (e.g., a compound of Formula VI or VID that comprises a group L-K) is reduced when compared to the systemic exposure of a therapeutically effective amount of Compound 100A. In some embodiments, the AUC of a therapeutically effective amount of a compound of Formula VI or VID that is not systemically absorbed (e.g., a compound of Formula VI or VID that comprises a group L-K) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula VI or VID that is not systemically absorbed (e.g., a compound of Formula VI or VID that comprises a group L-K) is about 50% reduced when compared to the AUC of a therapeutically effective amount of Compound 100A. In other embodiments, the AUC of a therapeutically effective amount of a compound of Formula I that is not systemically absorbed (e.g., a compound of Formula VI or VID that comprises a group L-K) is about 75% reduced when compared to the AUC of a therapeutically effective amount of Compound 100A.

In certain embodiments, the Cmax of a therapeutically effective amount of any non-systemic ASBTI described herein (e.g., an ASBTI that comprises a group L-K) is at least 10%, at least 20%, at least 30%, at least 40%, at least 50%, at least 60%, at least 70%, at least 80% or at least 90% reduced when compared to the Cmax of any systemically absorbed ASBTI (e.g. Compound 100A).

By way of example, the Cmax of a therapeutically effective amount of a compound of Formula III, IIIA, IIIB or IIIC is about 10%, about 20%, about 30%, about 40%, about 50%, about 60%, about 70%, about 80% or about 90% reduced when compared to the Cmax of a therapeutically effective amount of Compound 100C. In some embodiments, the Cmax of a therapeutically effective amount of a compound of Formula III, IIIA, IIIB or IIIC is about 25% reduced when compared to the Cmax of a therapeutically effective amount of Compound 100C. In certain embodiments, the Cmax of a therapeutically effective amount of a compound of III, IIIA or IIIB is about 50% reduced when compared to the Cmax of a therapeutically effective amount of Compound 100C. In other embodiments, the Cmax of a therapeutically effective amount of a compound of Formula III, IIIA, IIIB or IIIC is about 75% reduced when compared to the Cmax of a therapeutically effective amount of Compound 100C.

Combination Therapy

In certain instances, provided herein are combination compositions and/or therapies comprising any compound described herein and an additional therapeutic agent. In some embodiments, the additional therapeutic agent is a L-cell endocrine peptide enhancer. In some instances, the L-cell endocrine peptide enhancer is a GLP-1 enhancer. In some embodiments, the GLP-1 enhancer is GLP-1, a GLP-1 secretion enhancer, a GLP-1 degradation inhibitor, the like, or a combination thereof. In certain instances, enhanced GLP-1 concentration provides a reduction in food intake and/or a reduction in gastric emptying in human subjects.

In some embodiments, the L-cell endocrine peptide enhancer is a GLP-2 enhancer. In certain instances, the GLP-2 enhancer is GLP-2, a GLP-2 secretion enhancer, a GLP-2 degradation inhibitor, the like, or a combination thereof. In certain instances, enhanced GLP-2 secretion inhibits gastric emptying and reduces intestinal permeability. In some instances, enhanced GLP-2 secretion inhibits gastric acid secretion. In some instances, enhanced GLP-2 secretion reduces or prevents inflammation in the gastrointestinal tract (gastrointestinal enteritis). In some instances, enhanced GLP-2 secretion regenerates and/or heals injury to gastrointestinal tissues (e.g., radiation enteritis).

In some instances, the L-cell endocrine peptide enhancer is a PYY enhancer. In some instances, enhanced secretion of PYY provides a reduction in sensation of hunger. In some instances, the L-cell endocrine peptide enhancer is an oxyntomodulin enhancer. In some instances, the enhanced secretion of oxyntomodulin inhibits meal-stimulated gastric secretion.

TGR5 Receptor Modulators

In some instances, the additional therapeutic agent modulates bile acid receptors in the gastrointestinal lumen. In some embodiments, the additional therapeutic agent agonizes or partially agonizes bile acid receptors (e.g., TGR5 receptors or Farnesoid-X receptors) in the gastrointestinal tract. In some embodiments, the additional therapeutic agent is a bile acid analog. In certain instances the additional therapeutic agent is a TGR5 agonist. In certain instances, administration of a TGR5 agonist in combination with any of the compounds described herein enhances the secretion of enteroendocrine peptides from L-cells. TGR5 modulators (e.g., agonists) include, and are not limited to, the compounds described in, WO 2008/091540, WO 2008/067219 and U.S. Appl. No. 2008/0221161.

Biguanides

In some embodiments, the additional therapeutic agent is a biguanide. In some instances, biguanides reduce blood and/or plasma glucose levels. Examples of biguanides include and are not limited to metformin, buformin, phenformin, proguanil or the like.

Incretin Mimetics

In some embodiments, the additional therapeutic agent is an incretin mimetic. In some embodiments, an incretic mimic augments pancreas response to ingestion of food, In some instances, administration of an incretin mimetic in combination with any of the compounds described herein lowers blood and/or plasma glucose levels. Examples of incretin mimetics include and are not limited to exenatide (Byetta®).

One currently used therapy for the treatment of diabetes is a subcutaneous injection of exenatide (Byetta®). In some embodiments, an oral combination of an ASBTI and a DPP-IV inhibitor is equally or more effective than an injection of exenatide in reducing plasma glucose levels. In some embodiments, an oral combination of an ASBTI and a DPP-IV inhibitor reduces or eliminates discomfort associated with injections of glucose-lowering medications.

Thiazolidinediones

In some embodiments, the additional therapeutic agent is a thiazolidinedione. In some instances thiazolidinediones reverse insulin resistance and lower blood and/or plasma glucose levels. Examples of thiazolidinediones include and are not limited to Rosiglitazone (Avandia), Pioglitazone (Actos), Troglitazone (Rezulin), MCC-555, rivoglitazone, ciglitazone or the like.

Enteroendocrine Peptides

In some embodiments, the additional therapeutic agent is an enteroendocrine peptide.

In some embodiments, enteroendocrine peptides reverse insulin resistance and lower blood and/or plasma glucose levels. Examples of enteroendocrine peptides that are administered as additional therapeutic agents include and are not limited to GLP-1 or GLP-1 analogs such as Taspoglutide® (Ipsen), or the like.

Combination Therapy with ASBTI and DPP-IV Inhibitor

In specific embodiments, the additional therapeutic agent inhibits degradation of L-cell enteroendocrine peptides. In certain embodiments, the additional therapeutic agent is a DPP-IV inhibitor. In certain instances, administration of an ASBTI to an individual in need thereof enhances the secretion of GLP-1; administration of a DPP-IV inhibitor in combination with the ASBTI reduces or inhibits degradation of GLP-1 thereby prolonging the therapeutic benefit of enhanced levels of GLP-1. In some embodiments, administration of an ASBTI reduces weight of an individual. In some embodiments, administration of an ASBTI in combination with a DPP-IV inhibitor reduces weight of an individual.

Figure 2:
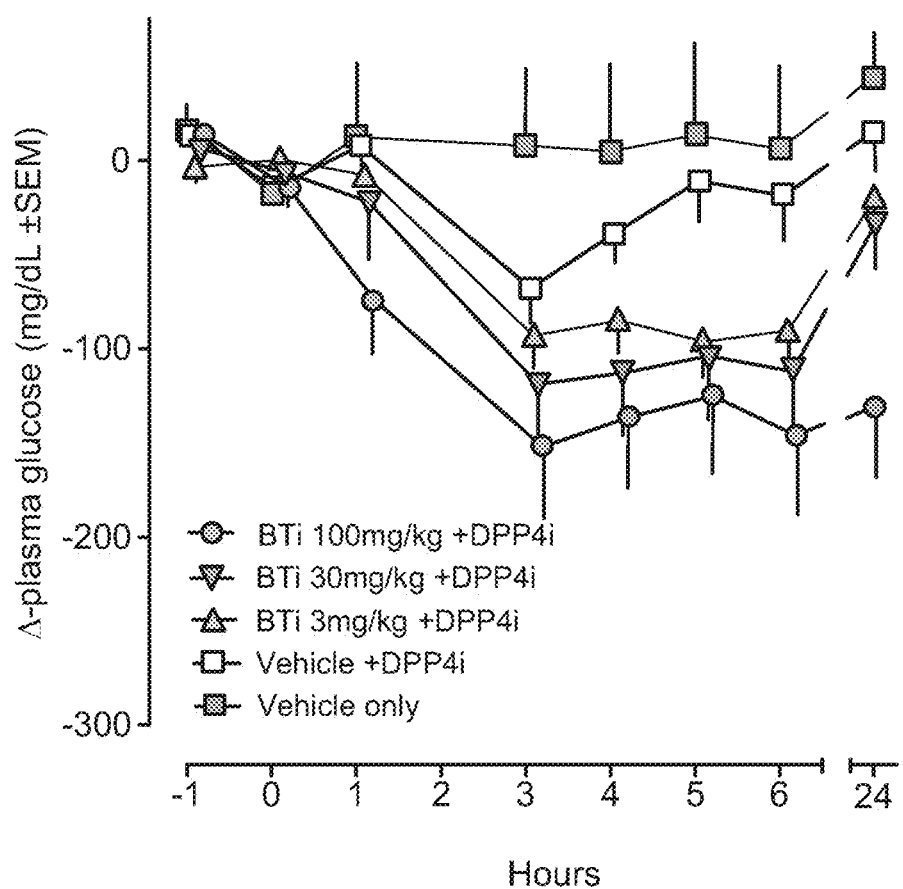
FIG. 2 illustrates the change in plasma glucose level in diabetic db/db mice after oral administration of a combination of the ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate at doses of 0, 3, 30, 100 mg/kg and 30 mg/kg sitagliptin (DPP-IV inhibitor).
Figure 3:
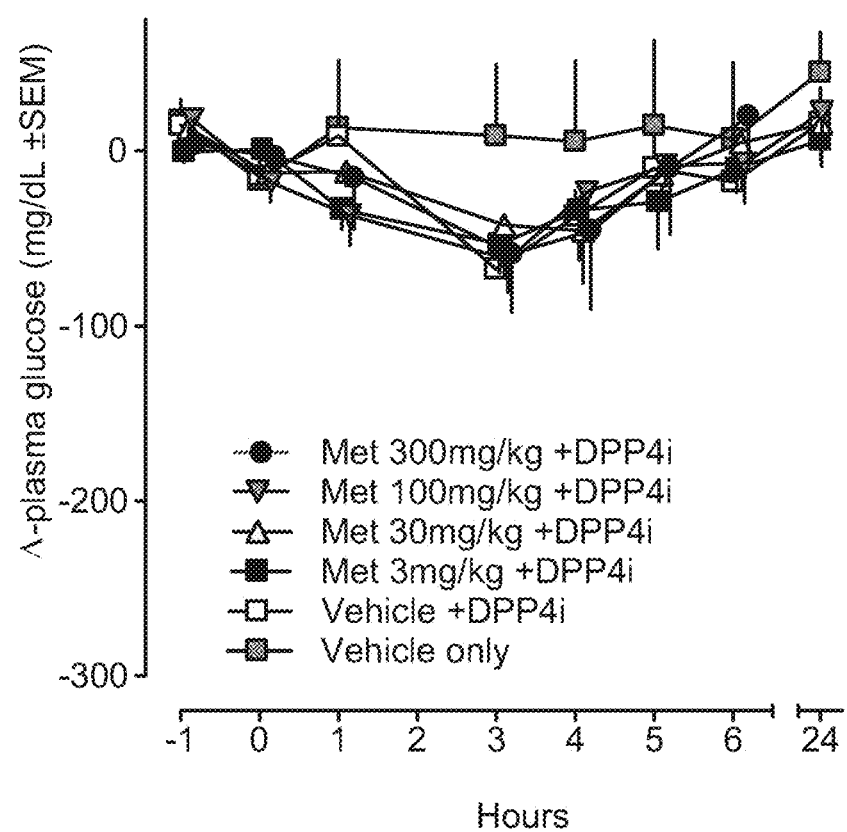
FIG. 3 illustrates the change in plasma glucose level in diabetic db/db mice after oral administration of a combination of metformin at doses of 0, 3, 30, 100, 300 mg/kg and 30 mg/kg sitagliptin (DPP-IV inhibitor).

Another therapy that is current standard of care for the treatment of diabetes is a combination of metformin and sitagliptin (Janumet®). At doses of 0, 3, 30, 100, 300 mg/kg doses of metformin in combination with 30 mg/kg of sitagliption, reductions in plasma glucose concentrations are observed from 3 hours till about 6 hours post-dose (FIG. 3). In some embodiments, a combination of an ASBTI and sitagliptin maintains reduced plasma glucose concentrations for a longer duration of time (e.g., at least 24 hours) compared to a combination of metformin and sitagliptin (about 6 hours) (FIGS. 1 and 2). In some instances ASBTI therapy eliminates side effects associated with metformin therapy and/or DPP-IV inhibitor therapy.

DPP-IV inhibitors suitable for use with the methods described herein include and are not limited to (2S)-1-{2-[(3-hydroxy-1-adamantyl)amino]acetyl}pyrrolidine-2-carbonitrile (vildagliptin), (3R)-3-amino-1-[9-(trifluoromethyl)-1,4,7,8-tetrazabicyclo[4.3.0]nona-6,8-dien-4-yl]-4-(2,4,5-trifluorophenyl)butan-1-one (sitagliptin), (1S,3S,5S)-2-[(2S)-2-amino-2-(3-hydroxy-1-adamantyl)acetyl]-2-azabicyclo[3.1.0]hexane-3-carbonitrile (saxagliptin), and 2-({6-[(3R)-3-aminopiperidin-1-yl]-3-methyl-2,4-dioxo-3,4-dihydropyrimidin-1(2H)-yl}methyl)benzonitrile (alogliptin).

In some embodiments of any of the methods described herein, administration of an ASBT inhibitor described herein in combination with a DPP-IV inhibitor increases the level of GLP-1 in the blood and/or plasma of an individual by from about 1.1 times to about 30 times compared to the level of GLP-1 in the blood and/or plasma of the individual prior to administration of the ASBTI in combination with the DPP-IV inhibitor. In some embodiments of any of the methods described herein, administration of an ASBT inhibitor described herein in combination with a DPP-IV inhibitor increases the level of GLP-1 in the blood and/or plasma of an individual by from about 1.1 times to about 20 times compared to the level of GLP-1 in the blood and/or plasma of the individual prior to administration of the ASBTI in combination with the DPP-IV inhibitor. In some embodiments of any of the methods described herein, administration of an ASBT inhibitor described herein in combination with a DPP-IV inhibitor increases the level of GLP-1 in the blood and/or plasma of an individual by from about 1.5 times to about 10 times compared to the level of GLP-1 in the blood and/or plasma of the individual prior to administration of the ASBTI in combination with the DPP-IV inhibitor. In some embodiments of any of the methods described herein, administration of an ASBT inhibitor described herein in combination with a DPP-IV inhibitor increases the level of GLP-1 in the blood and/or plasma of an individual by from about 2 times to about 8 times compared to the level of GLP-1 in the blood and/or plasma of the individual prior to administration of the ASBTI in combination with the DPP-IV inhibitor. In some embodiments of any of the methods described herein, administration of an ASBT inhibitor described herein in combination with a DPP-IV inhibitor increases the level of GLP-1 in the blood and/or plasma of an individual by from about 2 times to about 6 times compared to the level of GLP-1 in the blood and/or plasma of the individual prior to administration of the ASBTI in combination with the DPP-IV inhibitor. In some instances, an increase in GLP-1 level of from about 2 times to about 3 times following the administration of an ASBT inhibitor described herein in combination with a DPP-IV inhibitor compared to the level of GLP-1 in the blood and/or plasma of the individual prior to administration of the ASBTI in combination with the DPP-IV inhibitor is associated with an anti-diabetic effect. In some instances, an increase in GLP-1 level of from about 3 times to about 8 times following the administration of an ASBT inhibitor described herein in combination with a DPP-IV inhibitor compared to the level of GLP-1 in the blood and/or plasma of the individual prior to administration of the ASBTI in combination with a DPP-IV inhibitor is associated with reduction in food intake and/or induction of satiety and/or weight loss.

In certain embodiments of any of the methods described herein, administration of an ASBTI in combination with a DPP-IV inhibitor reduces blood and/or plasma sugar levels by at least 20%, at least 30%, at least 40%, at least 50% at least 60%, at least 70% or at least 80% compared to blood and/or plasma sugar levels prior to administration of the ASBTI in combination with a DPP-IV inhibitor. In some embodiments of any of the methods described herein, administration of an ASBTI in combination with a DPP-IV inhibitor reduces blood and/or plasma sugar levels by at least 20% compared to blood and/or plasma sugar levels prior to administration of the ASBTI in combination with a DPP-IV inhibitor. In some embodiments of any of the methods described herein, administration of an ASBTI in combination with a DPP-IV inhibitor reduces blood and/or plasma sugar levels by at least 30% compared to blood and/or plasma sugar levels prior to administration of the ASBTI in combination with a DPP-IV inhibitor. In some embodiments of any of the methods described herein, administration of an ASBTI in combination with a DPP-IV inhibitor reduces blood and/or plasma sugar levels by at least 40% compared to blood and/or plasma sugar levels prior to administration of the ASBTI in combination with a DPP-IV inhibitor.

In some embodiments of any of the methods described herein, administration of an ASBTI in combination with a DPP-IV inhibitor reduces blood and/or plasma sugar levels for a longer period of time (e.g., at least 24 hours) compared to reduction in blood and/or plasma sugar levels upon administration of metformin in combination with a DPP-IV inhibitor. In some embodiments of any of the methods described herein, administration of a single dose of an ASBTI in combination with a DPP-IV inhibitor sustains reduced blood and/or plasma sugar levels for at least 6 hours, at least 12 hours, at least 14 hours, at least 16 hours, at least 18 hours, at least 20 hours, at least 24 hours, at least 30 hours, at least 36 hours or at least 48 hours compared to reduction in blood and/or plasma sugar levels upon administration of a single dose of metformin in combination with a DPP-IV inhibitor.

In some embodiments of any of the methods described herein, administration of an ASBTI in combination with a DPP-IV inhibitor results in higher levels of GLP-1 in blood and/or plasma of an individual compared to levels of GLP-1 in blood and/or plasma of a normal individual. In some embodiments of any of the methods described herein, administration of an ASBTI in combination with a DPP-IV inhibitor results in higher levels of GLP-1 in blood and/or plasma of an individual compared to levels of GLP-1 in blood and/or plasma of an individual undergoing therapy with metformin and/or a DPP-IV inhibitor.

Combination therapy with ASBTI, biliary shunt and DPP-IV inhibitor

In some embodiments, an ASBTI is administered in combination with a DPP-IV inhibitor and/or a biliary shunt. Examples of biliary shunts include and are not limited to the shunts described in WO 2007/0050628, the disclosure of biliary shunts described therein is incorporated herein by reference. In some of such embodiments, a biliary shunt moves bile acid to the distal ileum and/or the rectum and/or the colon thereby increasing the concentration of bile acids in the vicinity of L-cells present in the distal portion of the gastrointestinal tract. In some instances such an increase in the concentration of bile acids in the vicinity of L-cells increases the secretion of GLP-1 from L-cells thereby inducing satiety and/or reduction in hunger and/or weight loss and/or reduction in plasma glucose levels or any combination thereof.

An ASBTI and a second active ingredient are used such that the combination is present in a therapeutically effective amount. That therapeutically effective amount arises from the use of a combination of an ASBTI and the other active ingredient (e.g., a DPP-IV inhibitor) wherein each is used in a therapeutically effective amount, or by virtue of additive or synergistic effects arising from the combined use, each can also be used in a subclinical therapeutically effective amount, i.e., an amount that, if used alone, provides for reduced effectiveness for the therapeutic purposes noted herein, provided that the combined use is therapeutically effective. In some embodiments, the use of a combination of an ASBTI and any other active ingredient as described herein encompasses combinations where the ASBTI or the other active ingredient is present in a therapeutically effective amount, and the other is present in a subclinical therapeutically effective amount, provided that the combined use is therapeutically effective owing to their additive or synergistic effects. As used herein, the term "additive effect" describes the combined effect of two (or more) pharmaceutically active agents that is equal to the sum of the effect of each agent given alone. A syngergistic effect is one in which the combined effect of two (or more) pharmaceutically active agents is greater than the sum of the effect of each agent given alone. Any suitable combination of an ASBIT with one or more of the aforementioned other active ingredients and optionally with one or more other pharmacologically active substances is contemplated as being within the scope of the methods described herein.

In some embodiments, the particular choice of compounds depends upon the diagnosis of the attending physicians and their judgment of the condition of the individual and the appropriate treatment protocol. The compounds are optionally administered concurrently (e.g., simultaneously, essentially simultaneously or within the same treatment protocol) or sequentially, depending upon the nature of the disease, disorder, or condition, the condition of the individual, and the actual choice of compounds used. In certain instances, the determination of the order of administration, and the number of repetitions of administration of each therapeutic agent during a treatment protocol, is based on an evaluation of the disease being treated and the condition of the individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents (at least one of which is a therapeutic compound described herein) are optionally administered in any order or even simultaneously. If simultaneously, the multiple therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g, from more than zero weeks to less than four weeks. In addition, the combination methods, compositions and formulations are not to be limited to the use of only two agents; the use of multiple therapeutic combinations are also envisioned (including two or more compounds described herein).

In certain embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents which make up the combination therapy described herein are provided in a combined dosage form or in separate dosage forms intended for substantially simultaneous administration. In certain embodiments, the pharmaceutical agents that make up the combination therapy are administered sequentially, with either therapeutic compound being administered by a regimen calling for two-step administration. In some embodiments, two-step administration regimen calls for sequential administration of the active agents or spaced-apart administration of the separate active agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

In certain embodiments, ASBTI compounds described herein are combined with or utilized in combination with one or more of the following therapeutic agents in any combination: insulin, insulin-mimetics, incretin mimetics, GLP-1 or analogs thereof, GLP-2 or analogs thereof, oxyntomodulin, PYY, DPP-IV inhibitors, or TGR5 modulators.

Pharmaceutical Compositions

Provided herein, in certain embodiments, is a pharmaceutical composition comprising a therapeutically effective amount of any compound described herein. In certain instances, the pharmaceutical composition comprises an ASBT inhibitor (e.g., any ASBTI described herein).

In certain embodiments, pharmaceutical compositions are formulated in a conventional manner using one or more physiologically acceptable carriers including, e.g., excipients and auxiliaries which facilitate processing of the active compounds into preparations which are suitable for pharmaceutical use. In certain embodiments, proper formulation is dependent upon the route of administration chosen. A summary of pharmaceutical compositions described herein is found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

A pharmaceutical composition, as used herein, refers to a mixture of a compound described herein, such as, for example, a compound of Formula I-VI, with other chemical components, such as carriers, stabilizers, diluents, dispersing agents, suspending agents, thickening agents, and/or excipients. In certain instances, the pharmaceutical composition facilitates administration of the compound to an individual or cell. In certain embodiments of practicing the methods of treatment or use provided herein, therapeutically effective amounts of compounds described herein are administered in a pharmaceutical composition to an individual having a disease, disorder, or condition to be treated. In specific embodiments, the individual is a human. As discussed herein, the compounds described herein are either utilized singly or in combination with one or more additional therapeutic agents.

In certain embodiments, the pharmaceutical formulations described herein are administered to an individual in any manner, including one or more of multiple administration routes, such as, by way of non-limiting example, oral, parenteral (e.g., intravenous, subcutaneous, intramuscular), intranasal, buccal, topical, rectal, or transdermal administration routes.

In certain embodiments, a pharmaceutical compositions described herein includes one or more compound described herein as an active ingredient in free-acid or free-base form, or in a pharmaceutically acceptable salt form. In some embodiments, the compounds described herein are utilized as an N-oxide or in a crystalline or amorphous form (i.e., a polymorph). In some situations, a compound described herein exists as tautomers. All tautomers are included within the scope of the compounds presented herein. In certain embodiments, a compound described herein exists in an unsolvated or solvated form, wherein solvated forms comprise any pharmaceutically acceptable solvent, e.g., water, ethanol, and the like. The solvated forms of the compounds presented herein are also considered to be described herein.

A "carrier" includes, in some embodiments, a pharmaceutically acceptable excipient and is selected on the basis of compatibility with compounds described herein, such as, compounds of any of Formula I-VI, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., Remington: *The Science and Practice of Pharmacy*, Nineteenth Ed (Easton, Pa.: Mack Publishing Company, 1995);

Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999).

Moreover, in certain embodiments, the pharmaceutical compositions described herein are formulated as a dosage form. As such, in some embodiments, provided herein is a dosage form comprising a compound described herein, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Release in Distal Ileum and/or Colon

In certain embodiments, a dosage form comprises a matrix (e.g., a matrix comprising hypermellose) that allows for controlled release of an active agent in the distal jejunum, proximal ileum, distal ileum and/or the colon. In some embodiments, a dosage form comprises a polymer that is pH sensitive (e.g., a MMX™ matrix from Cosmo Pharmaceuticals) and allows for controlled release of an active agent in the ileum and/or the colon. Examples of such pH sensitive polymers suitable for controlled release include and are not limited to polyacrylic polymers (e.g., anionic polymers of methacrylic acid and/or methacrylic acid esters, e.g., Carbopol® polymers) that comprise acidic groups (e.g., —COOH, —SO$_3$H) and swell in basic pH of the intestine (e.g., pH of about 7 to about 8). In some embodiments, a dosage form suitable for controlled release in the distal ileum comprises microparticulate active agent (e.g., micronized active agent). In some embodiments, a non-enzymatically degrading poly(dl-lactide-co-glycolide) (PLGA) core is suitable for delivery of an ASBTI to the distal ileum. In some embodiments, a dosage form comprising an ASBTI is coated with an enteric polymer (e.g., Eudragit® S-100, cellulose acetate phthalate, polyvinylacetate phthalate, hydroxypropylmethylcellulose phthalate, anionic polymers of methacrylic acid, methacrylic acid esters or the like) for site specific delivery to the ileum and/or the colon. In some embodiments, bacterially activated systems are suitable for targeted delivery to the ileum. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like.

The pharmaceutical solid dosage forms described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in *Remington's Pharmaceutical Sciences*, 20th Edition (2000), a film coating is provided around the formulation of the compound of Formula I-VI. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

An ASBT inhibitor (e.g., a compound of Formula I-VI) is used in the preparation of medicaments for the prophylactic and/or therapeutic treatment of obesity and/or diabetes. A method for treating any of the diseases or conditions described herein in an individual in need of such treatment, involves administration of pharmaceutical compositions containing at least one ASBT inhibitor described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

Screening Process

Provided in certain embodiments herein are processes and kits for identifying compounds suitable for treating obesity, metabolic disorders or disorders mediated by L-cell enteroendocrine peptides. In certain embodiments, provided herein are assays for identifying compounds that selectively inhibit the ASBT, or enhance the secretion of L-cell enteroendocrine peptides, or a combination thereof by:

a. providing cells that are a model of intestinal L-cells (e.g., SLC-1 cells, GLUTag cells, NCI-H719 cells);

b. contacting the cells with a compound (e.g., a compound as described herein);

c. detecting or measuring the effect of the compound on the secretion of enteroendocrine peptides (e.g., GLP-1, GLP-2) from the cells.

In certain embodiments, provided herein are assays for identifying compounds that are non-systemic compounds by a. providing cells that are a model of intestinal permeability (e.g., Caco-2 cells);

b. culturing the cells as a monolayer on semi-permeable plastic supports that are fitted into the wells of multi-well culture plates;

c. contacting the apical or basolateral surface of the cells with a compound (e.g., a compound as described herein) and incubating for a suitable length of time;

d. detecting or measuring the concentration of the compound on both sides of the monolayer by liquid-chromatography-mass spectrometry (LC-MS) and computing intestinal permeability of the compound.

In certain embodiments, non-systemic compounds are identified by suitable parallel artificial membrane permeability assays (PAMPA).

In certain embodiments, provided herein are assays for identifying compounds that inhibit recycling of bile acid salts by a. providing cells that are a model of intestinal cells with apical bile acid tranporters (e.g., BHK cells, CHO cells);

b. incubating the cells with a compound (e.g., a compound as described herein) and/or a radiolabeled bile acid (e.g., $^{14}C$ taurocholate) for a suitable length of time;

c. washing the cells with a suitable buffer (e.g. phosphate buffered saline);

d. detecting or measuring the residual concentration of the radiolabeled bile acid in the cells.

EXAMPLES

Example 1: Synthesis of 1-phenethyl-1-((1,4-diazabicyclo[2.2.2]octanyl)pentyl)imidodicarbonimidic diamide, Iodide Salt

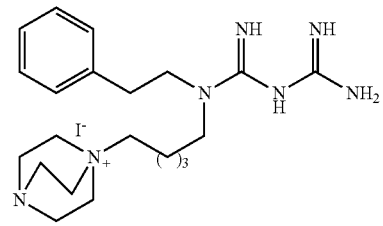

Step 1: Synthesis of 5-(1,4-diazabicyclo[2.2.2]octanyl)-1-iodo pentane, Iodide Salt

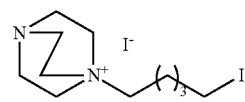

1,4-diazabicyclo[2.2.2]octane is suspended in THF. Diiodopentane is added dropwise and the mixture is refluxed overnight. The reaction mixture is filtered.

Step 2: Synthesis of N-phenethyl-5-(1,4-diazabicyclo[2.2.2]octanyl)-1-iodo pentane, Iodide Salt

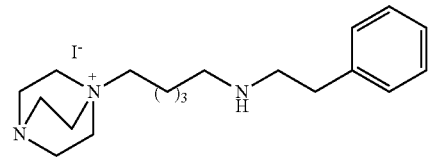

5-(1,4-diazabicyclo[2.2.2]octanyl)-1-iodide pentane, iodide salt is suspended in acetonitrile. Phenethylamine is added dropwise and the mixture is refluxed overnight. The reaction mixture is filtered.

Step 3: Synthesis of 1-phenethyl-1-((1,4-diazabicyclo[2.2.2]octanyl)pentyl)imidodicarbonimidic diamide, Iodide Salt N-phenethyl-5-(1,4-diazabicyclo[2.2.2]octanyl)-1-iodo pentane, iodide salt is heated with dicyanodiamide in n-butanol for 4 h. The reaction mixture is concentrated under reduced pressure.

The compounds in Table 1 are prepared using methods as described herein, and using appropriate starting materials.

TABLE 1
| Compound No. | Structure |
|---|---|
| 1 | 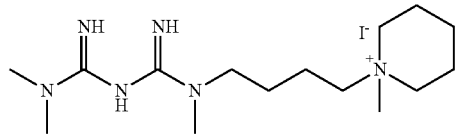 |
| 2 | 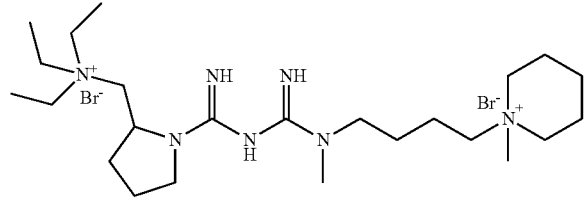 |
| 3 | 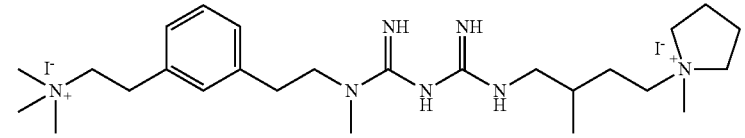 |
| 4 | 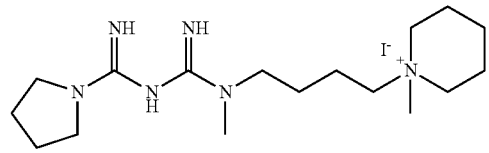 |
| 5 | 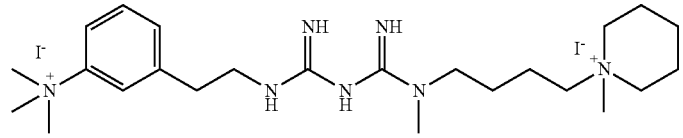 |
| 6 | 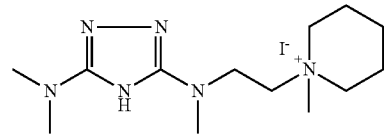 |
| 7 | 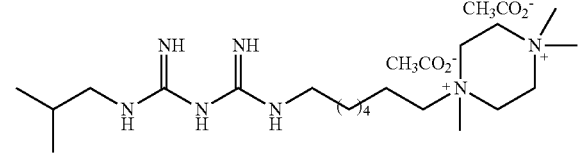 |
| 8 | 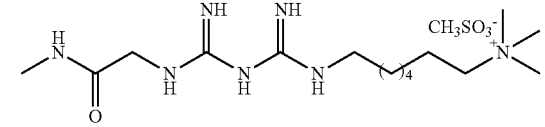 |
| 9 | 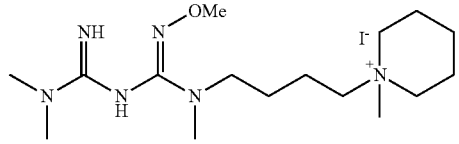 |

TABLE 1-continued

| Compound No. | Structure |
|---|---|
| 10 | [chemical structure] |
| 11 | [chemical structure] |

Example 2: In Vitro Assay for Inhibition of ASBT-mediated Bile Acid Uptake

Baby hamster kidney (BHK) cells are transfected with cDNA of human ASBT. The cells are seeded in 96-well tissue culture plates at 60,000 cells/well. Assays are run within 24 hours of seeding.

On the day of the assay the cell monolayer is washed with 100 mL of assay buffer. The test compound is added to each well along with 6 mM [$^{14}$C]taurocholate in assay buffer (final concentration of 3 mM [$^{14}$C]taurocholate in each well). The cell cultures are incubated for 2 h at 37° C. The wells are washed with PBS. Scintillation counting fluid is added to each well, the cells are shaken for 30 minutes prior to measuring amount of radioactivity in each well. A test compound that has significant ASBT inhibitory activity provides an assay wherein low levels of radioactivity are observed in the cells.

Example 3: In Vitro Assay for Secretion of GLP-1

Human NCI-H716 cells are used as a model for L-cells. Two days before each assay experiment, cells are seeded in 12-well culture plates coated with Matrigel® to induce cell adhesion. On the day of the assay, cells are washed with buffer. The cells are incubated for 2 hours with medium alone, or with test compound. The extracellular medium is assayed for the presence of GLP-1. Peptides in the medium are collected by reverse phase adsorption and the extracts are stored until assay. The presence of GLP-1 is assayed using an antiserum directed against the carboxyl terminus of GLP-1 amide (total immunoreactive GLP-1; Affinity Research Products, Nottingham, UK). The detection of increased levels of GLP-1 in a well containing a test compound identifies the test compound as a compound that can enhance GLP-1 secretions from L-cells.

Example 4: In Vivo Bioavailability Assay

The test compounds are solubilized in saline solutions. Sprague Dawley rats are dosed at 2-10 mg/kg body weight by iv and oral dosing. Peripheral blood samples are taken from the femoral artery at selected time periods up to 8 hours. Plasma concentrations of the compounds are determined by quantitative HPLC and/or mass spectrometry. Clearance and AUC values are determined for the compounds.

For oral dosing, bioavailabilty is calculated by also drawing plasma samples from the portal vein. Cannulae are inserted in the femoral artery and the hepatic portal vein to obtain estimates of total absorption of drug without first-pass clearance in the liver. The fraction absorbed (F) is calculated by $$F = AUC_{po}/AUC_{iv}$$

Example 5: In Vivo Animal Model of Obesity

A non-genetic mouse obesity model is used. Obesity is induced in a cohort of C57BL/6 (wild-type) mice, by a high-fat cafeteria diet. The mice are administered 30 mg/kg of compound 8 once daily as an oral solution in saline. The mice are weighed daily over a period of two weeks. Cafeteria dieting is continued throughout the experiment. Obese mice administered a saline solution alone (placebo) serve as negative controls. The weight gain in the control group is compared with the weight gain or loss of the test group.

Example 6: In Vivo Assay for Reduction in Blood Glucose Levels

Male db/db mice 6-7 weeks (approx 30 g) were fasted for 2 h. A combination of (−)-(3R,5R)-trans-3-butyl-3-ethyl-2,3,4,5-tetrahydro-7,8-dimethoxy-5-phenyl-1,4-benzothiazepine 1,1-dioxide (Compound 100A) at doses of 0, 0.1, 1, 10, mg/kg in 10% of DMSO-water and 30 mg/kg sitagliptin (DPP-IV inhibitor) in a mixture of valine-pyrrolidine in water was administered orally to male db/db mice (n=7-10 per group). Blood sample (~1 μl from tail for glucose level testing) was taken at t=−24 h, 0, 60, 180, 240, 300, 360 min and 24 h after administration.

Figure 9:
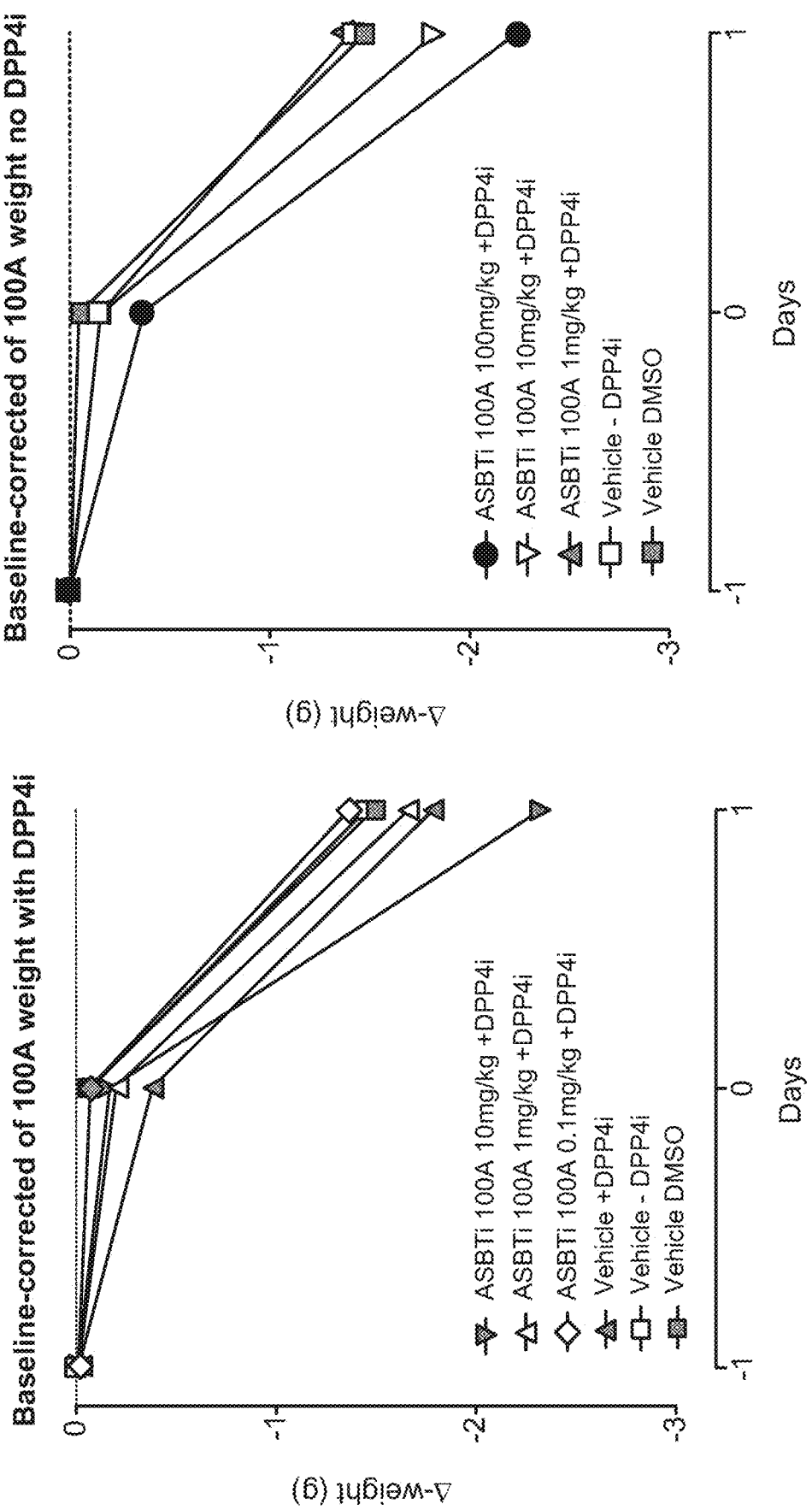
FIG. 9 illustrates the change in body weight 24 h after administration of the ASBTI (−)-(3R,5R)-trans-3-butyl-3-ethyl-2,3,4,5-tetrahydro-7,8-dimethoxy-5-phenyl-1,4-benzothiazepine1,1-dioxide (100A) at doses of 0, 0.1, 1, 10 mg/kg in combination with 30 mg/kg sitagliptin (DPP-IV inhibitor) and the ASBTI alone.

A single administration of (−)-(3R,5R)-trans-3-butyl-3-ethyl-2,3,4,5-tetrahydro-7,8-dimethoxy-5-phenyl-1,4-benzothiazepine 1,-dioxide in combination with sitagliptin produced a dose-dependent reduction of the elevated blood glucose levels compared to the control mice treated with sitagliptin alone or with vehicle solution of 10% of DMSO (FIG. 1). Reductions in plasma glucose concentrations are observed from 3 hours up to 24 hours post-dose and accompanied after 6 hours by a 5.5%, 5.6%, 15% and 42.3% reduction in plasma glucose from baseline, (doses of 0, 01, 1 and 10 mg/kg of (−)-(3R,5R)-trans-3-butyl-3-ethyl-2,3,4,5-tetrahydro-7,8-dimethoxy-5-phenyl-1,4-benzothiazepine1,1-dioxide respectively). Plasma glucose concentrations in the control mice treated with only the control vehicle (saline in 10% of DMSO) increased by 1.5% after 6 h. Administration of the ASBTI alone also lowers plasma glucose concentrations in male db/db mice as shown in FIG. 1. Weight loss is shown in FIG. 9.

Example 7: In Vivo Assay for Reduction in Blood Glucose Levels

Male db/db mice 8-9 weeks (approx 40 g) were fasted for 2 h. A combination of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Compound 100B) at doses of 0, 3, 30, 100 mg/kg in saline-water and 30 mg/kg sitagliptin (DPP-IV inhibitor) in a mixture of valine-pyrrolidine in water was administered orally to male db/db mice (n=6-11 per group). Blood sample (~1 μl from tail for glucose level testing) was taken at t=-24 h, 0, 1, 3, 4, 5, 6 h and 24 h after administration.

Figure 8:
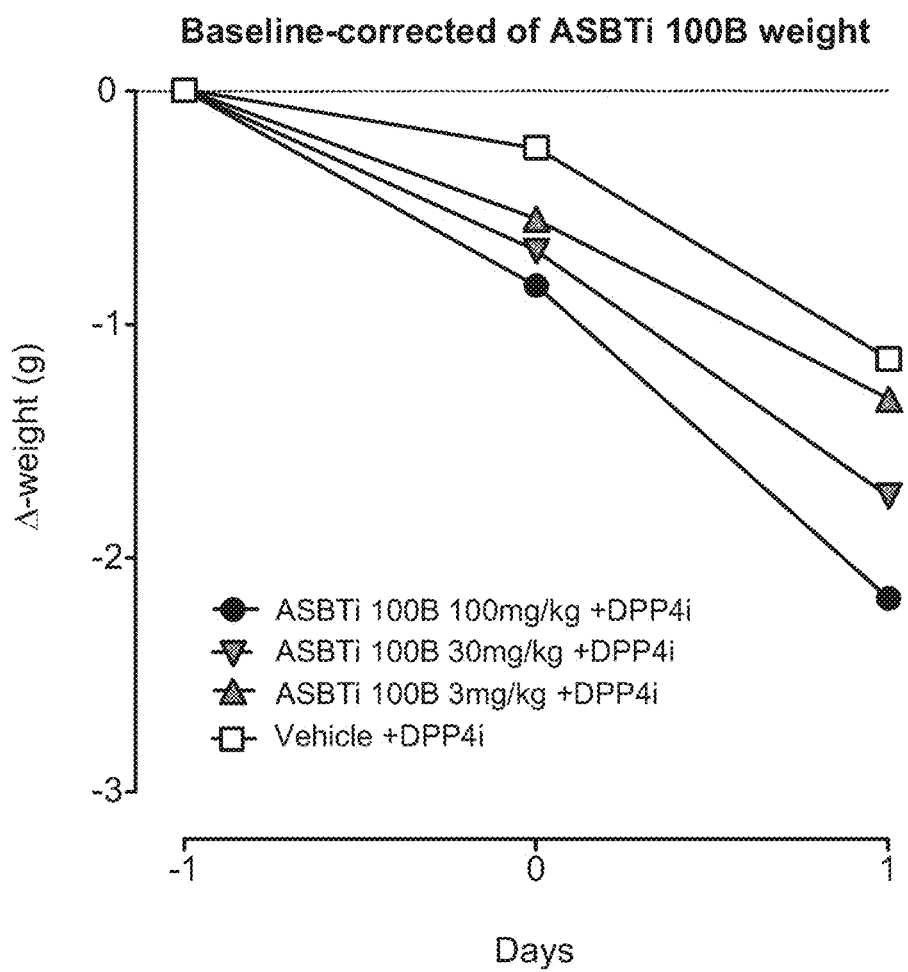
FIG. 8 illustrates the change in body weight 24 h after administration of ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (100B) at doses of 0, 3, 30, 100 mg/kg in combination with 30 mg/kg sitagliptin (DPP-IV inhibitor).

A single administration of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate in combination with sitagliptin produced a dose-dependent reduction of the elevated blood glucose levels compared to the control mice treated with sitagliptin alone or with vehicle solution of saline-water (FIG. 2). Reductions in plasma glucose concentrations are observed from 3 hours till 24 hours post-dose and accompanied after 6 hours by a 5.5%, 5.6%, 15% and 42.3% reduction in plasma glucose from baseline, (doses of 0, 3, 30 and 100 mg/kg of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate respectively). Plasma glucose concentrations in the control mice treated with only the control vehicle (saline-water) increased by 1.5% after 6 h (FIG. 2). Weight loss is shown in FIG. 8.

Figure 4:
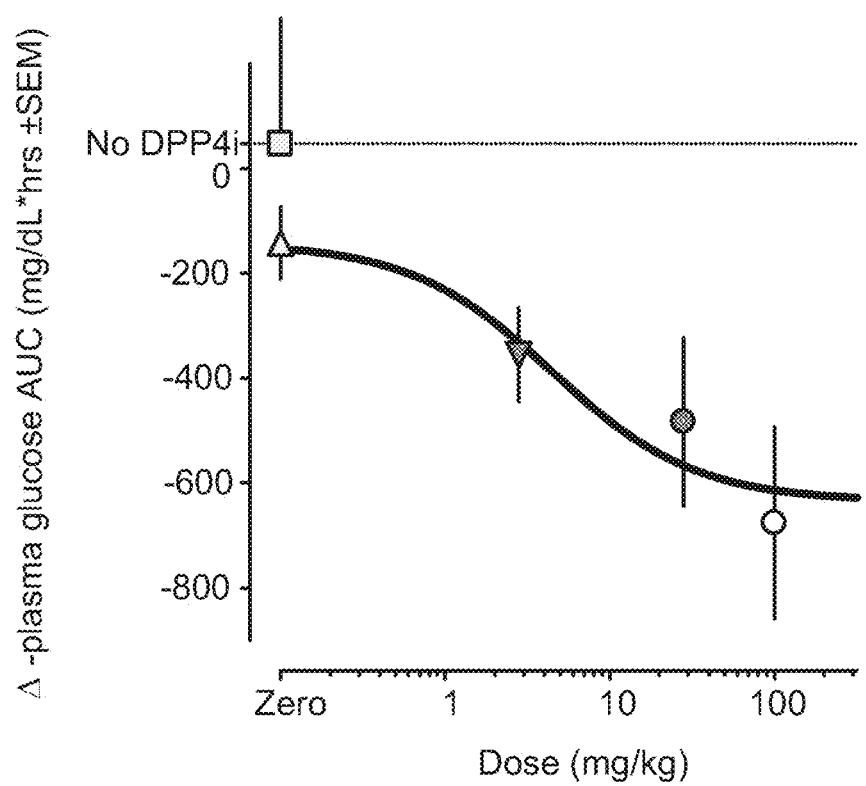
FIG. 4 illustrates the change in plasma glucose level in diabetic db/db mice after oral administration of the ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methanesulfonate salt at doses of 0, 3, 30, and 100 mg/kg.

Administration of doses of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate alone also lowers plasma glucose levels in dose dependent manner (FIG. 4).

Figure 5:
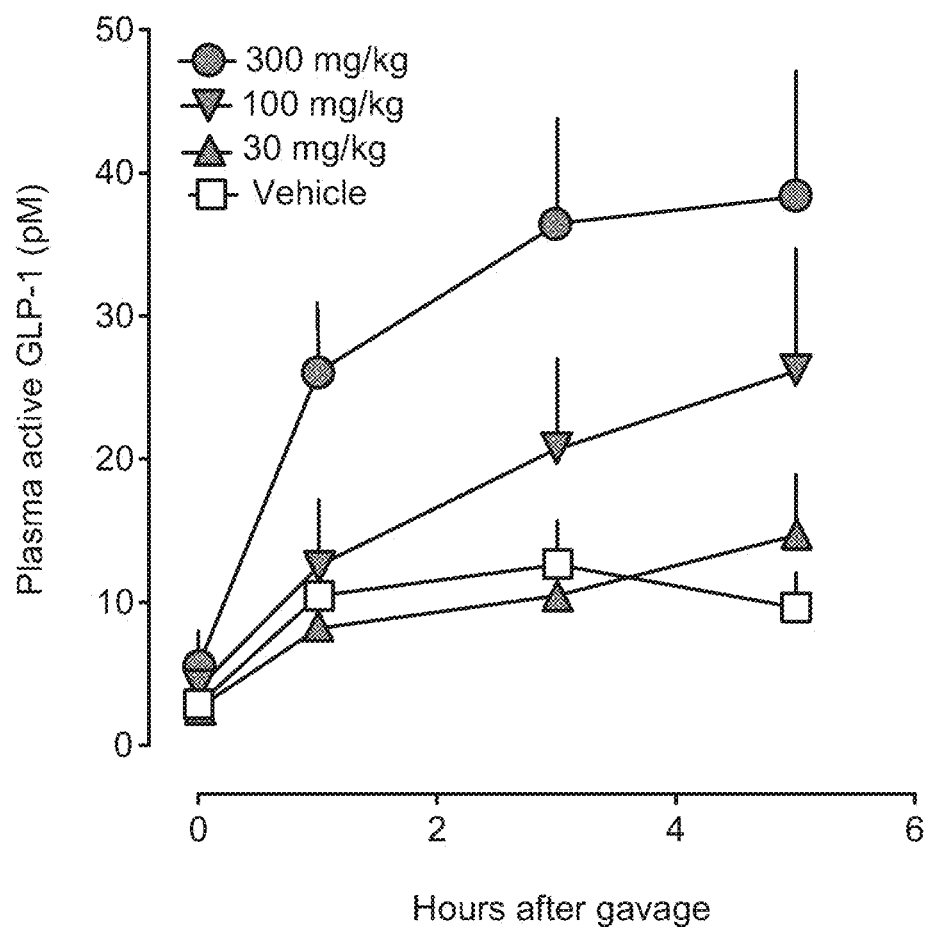
FIG. 5 illustrates a time course for dose-dependent increase in plasma GLP-1 level in normal rats upon administration of a combination of metformin (0, 30, 100, 300 mg/kg) and 30 mg/kg sitagliptin (DPP-IV inhibitor).
Figure 6:
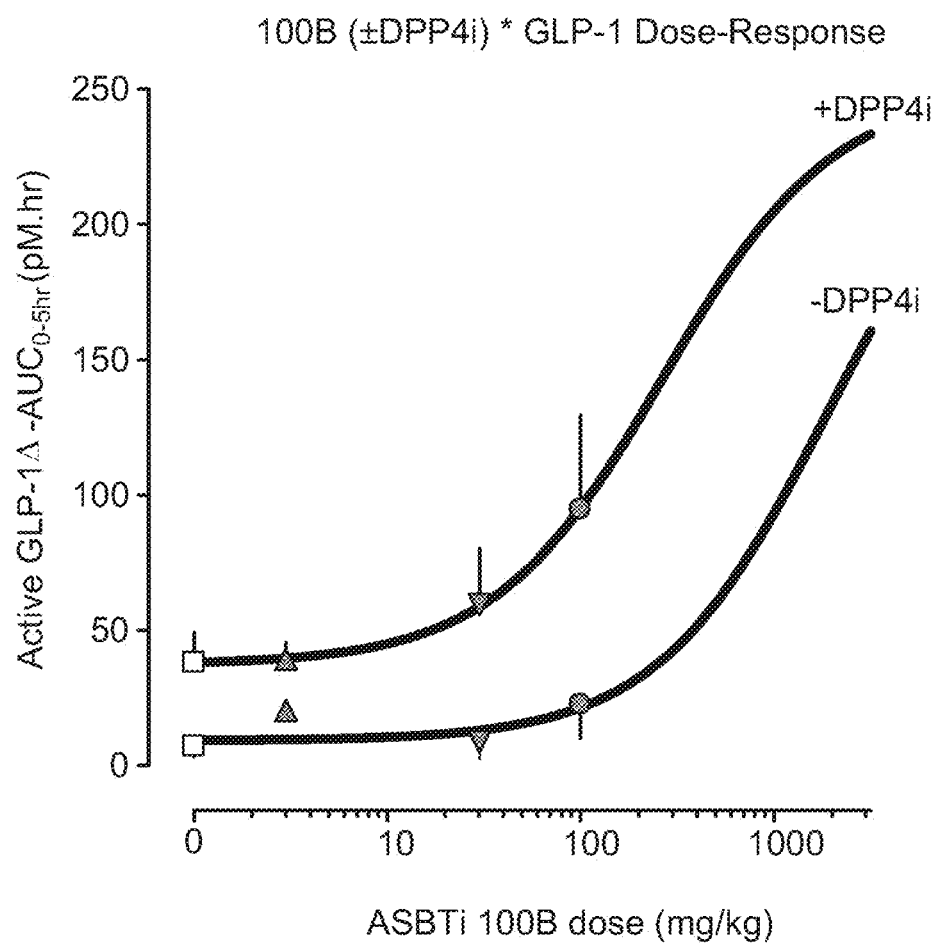
FIG. 6 illustrates a dose-dependent increase in plasma GLP-1 level in normal rats upon adminstration of a combination of the ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (100B) (0, 3, 30, 100 mg/kg) and 30 mg/kg sitagliptin (DPP-IV inhibitor) and the ASBTI alone.
Figure 7:
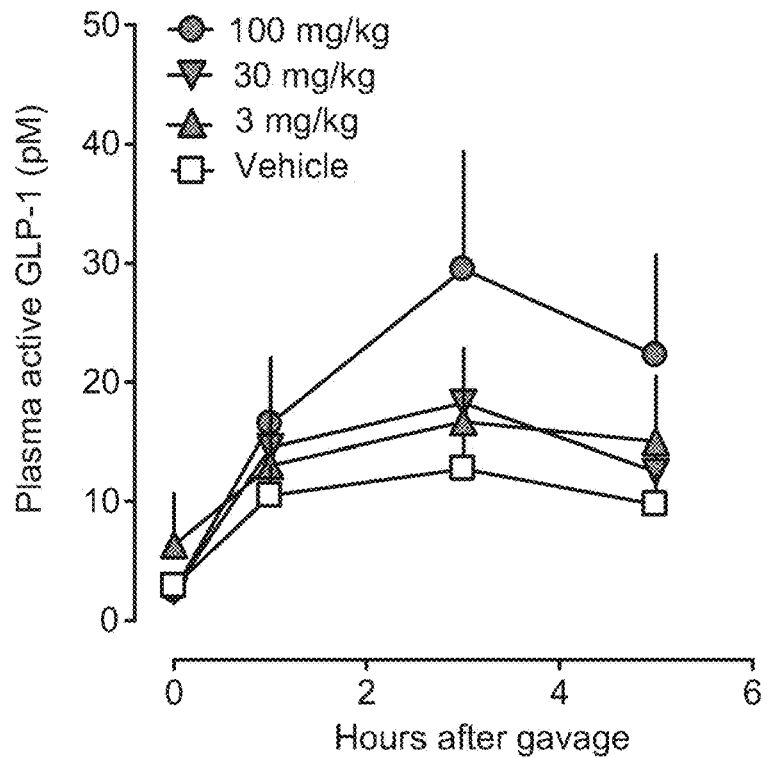
FIG. 7A and FIG. 7B illustrate a time course for dose-dependent increase in plasma GLP-1 level in normal rats upon administration of a combination of the ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (0, 3, 30, 100 mg/kg) and 30 mg/kg sitagliptin (DPP-IV inhibitor) and the ASBTI alone.
Figure 7:
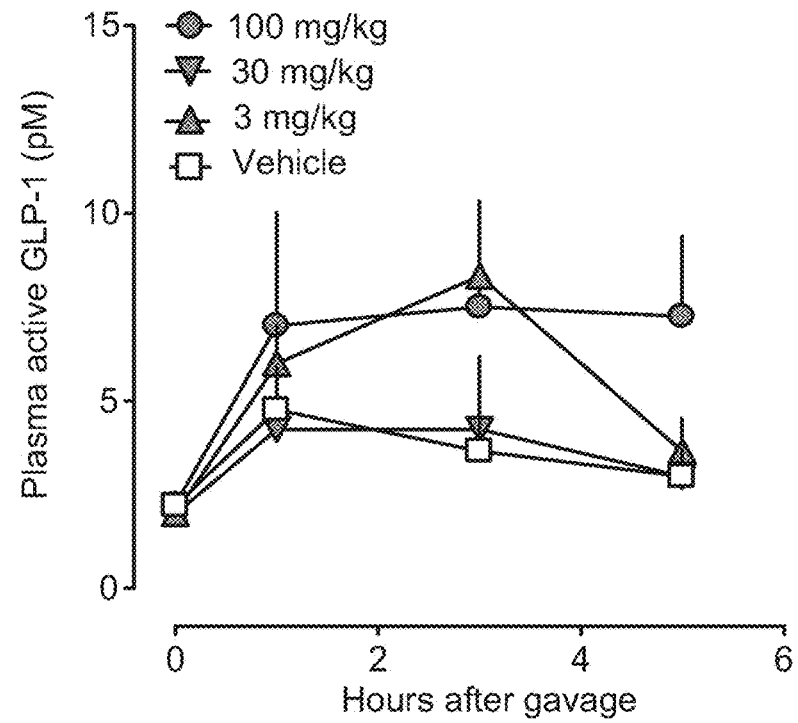

Example 8: Investigation of Orally Delivered 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2] octane methane sulfonate (Compound 100B) and Metformin in Combination with DPP-IV Inhibitor on Plasma GLP-1 Levels in Normal Rats 12-week-old male HSD rats were fasted for 16 h and given oral dose of 0, 3, 30, 100 mg/kg of the ASBTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Synthesized by Nanosyn Inc., CA, USA) or metformin (Control, 0, 3, 30, 100, 300 mg/kg) in saline and a dose of 30 mg/kg sitaglipin in a mixture of valine-pyrrolidine in water (n=5 per group). Blood samples in volume of 0.6 ml for each time point were taken from the caudal vein with a heparinized capillary tube 0, 1, 3 and 5 h after the administration of compounds and plasma GLP-1 level were determined. Aprotinin and 10 μl of DPP-IV inhibitor per ml of blood were used for blood sample preservation during 10 min centrifugation and for storage at −70° C. or below. GLP-1 (Active pM) was tested by Millipore ELISA Kits (Millipore Corporation, 290 Concord Road, Billerica, Mass.). ASBTI alone or ASBTI in combination with sitagliptin elicited an elevation in GLP-1 levels in a dose-dependent manner (FIG. 6, FIG. 7) in normal rats. FIG. 5 shows elevation in GLP-1 levels in plasma of normal rats upon administration of a combination of metformin and sitagliptin.

Figure 10:
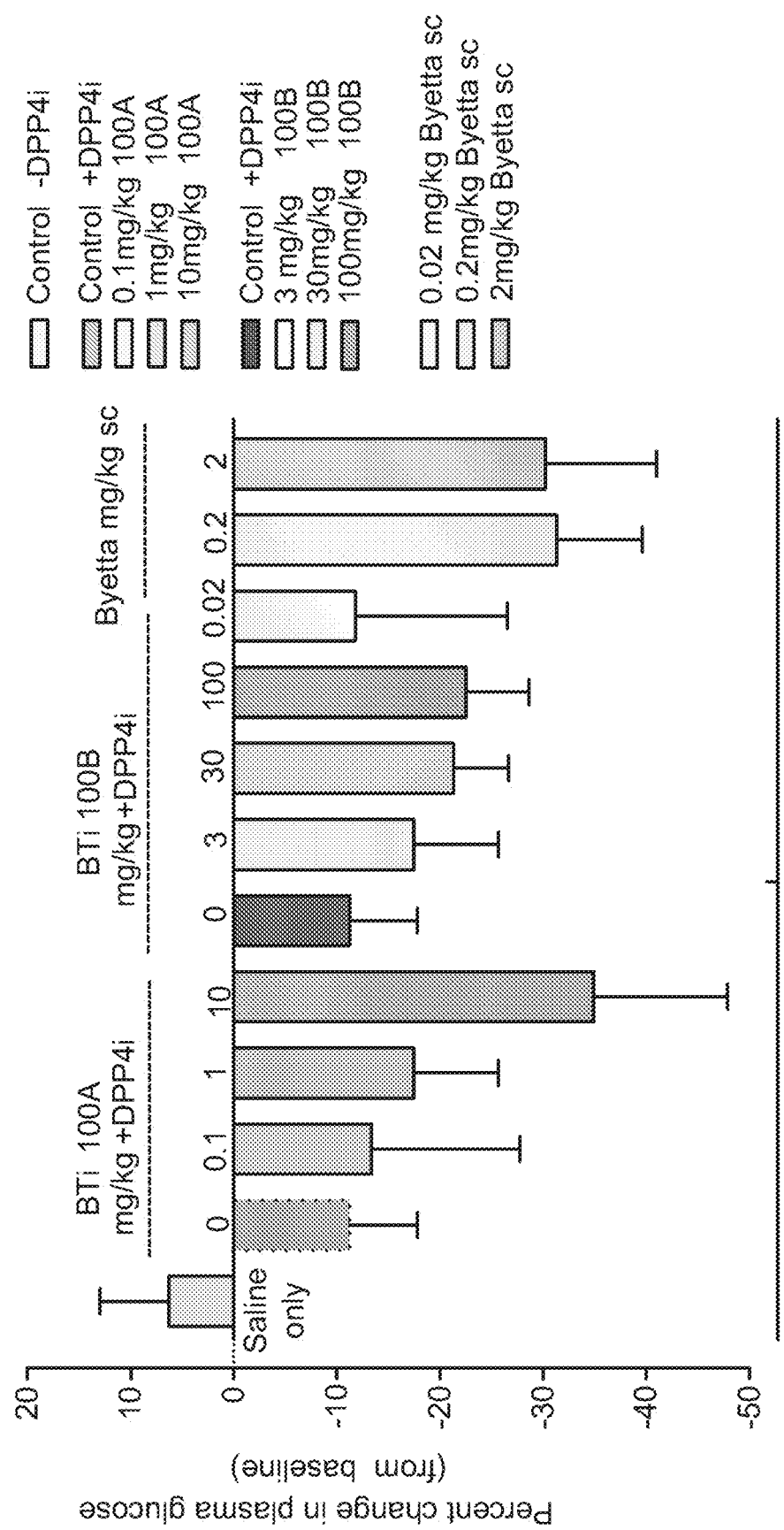
FIG. 10 illustrates (1) a comparison of orally administered combination of (−)-(3R,5R)-trans-3-butyl-3-ethyl-2,3,4,5-tetrahydro-7,8-dimethoxy-5-phenyl-1,4-benzothiazepine1,1-dioxide (100A) at doses of 0, 0.1, 1, 10 mg/kg and 30 mg/kg sitagliptin (DPP-IV inhibitor) on blood glucose levels in diabetic db/db mice at 3 hours after dose; and (2) a comparison of orally administered combination of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methanesulfonate salt (100B) at doses of 0, 3, 30, 100 mg/kg and 30 mg/kg sitagliptin (DPP-IV inhibitor) on blood glucose levels in diabetic db/db mice at 3 hours after dose; versus (3) subcutaneously injected exenatide at doses of 0.02, 0.2 and 2 mg·kg on blood glucose levels in diabetic db/db mice at 3 hours after dose.

Example 9: Investigation of Orally Delivered Compound 100A and 100B in Combination with DPP-IV Inhibitor Versus Subcutaneous Exenatide A similar experiment as described above is carried out to test doses of 0, 0.01, 1 and 10 mg/kg of the ASBTI (−)-(3R,5R)-trans-3-butyl-3-ethyl-2,3,4,5-tetrahydro-7,8-dimethoxy-5-phenyl-1,4-benzothiazepine1,1-dioxide (Compound 100A) in combination with 30 mg/kg sitagliptin and a subcutaneous injection of exenatide. An oral dose of a combination of (−)-(3R,5R)-trans-3-butyl-3-ethyl-2,3,4,5-tetrahydro-7,8-dimethoxy-5-phenyl-1,4-benzothiazepine 1,1-dioxide (10 mg/kg) in combination with 30 mg/kg sitagliptin reduces plasma glucose levels by 35% while a sub-cutaneous injection of exenatide (0.2 mg/kg) reduces plasma glucose level by 31% at 3 hours post-dose (FIG. 10).

A similar experiment as described above is carried out to compare glucose lowering effect of orally administered doses of 0, 3, 30, and 100, mg/kg of the ABTI 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Compound 100B) in combination with a 30 mg/kg dose of sitagliptin versus 0.02, 0.2 and 2 mg/kg doses of exenatide. FIG. 10 shows that an oral combination of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate in combination with a 30 mg/kg dose of sitagliptin reduces blood glucose levels more than a single subcutaneous injection of 0.02 mg/kg exenatide at 3 hours after dosing.

Example 10: Tablet Formulation 10 kg of a compound of Formula I-VI is first screened through a suitable screen (e.g. 500 micron). 25 kg Lactose monohydrate, 8 kg hydroxypropylmethyl cellulose, the screened compound of Formula I-VI and 5 kg calcium hydrogen phosphate (anhydrous) are then added to a suitable blender (e.g. a tumble mixer) and blended. The blend is screened through a suitable screen (e.g. 500 micron) and reblended. About 50% of the lubricant (2.5 kg, magnesium stearate) is screened, added to the blend and blended briefly. The remaining lubricant (2 kg, magnesium stearate) is screened, added to the blend and blended briefly. The granules are screened (e.g. 200 micron) to obtain granulation particles of the desired size. In some embodiments, the granules are optionally coated with a drug release controlling polymer such as polyvinylpyrrolidine, hydroxypropylcellulose, hydroxypropylmethyl cellulose, methyl cellulose, or a methacrylic acid copolymer, to provide an extended release formulation. The granules are filled in gelatin capsules.

Example 11: Human Clinical Trial of the Effect of (−)-(3R,5R)-trans-3-butyl-3-ethyl-2,3,4,5-tetrahydro-7,8-dimethoxy-5-phenyl-1,4-benzothiazepine 1,1-dioxide (Compound 100A) on Satiety and Reduction in Food Intake, Plasma Glucose and Insulin Levels Objective: The aim of the 8 week study is to show evidence of the efficacy (−)-(3R,5R)-trans-3-butyl-3-ethyl- 2,3,4,5-tetrahydro-7,8-dimethoxy-5-phenyl-1,4-benzothiazepine 1,1-dioxide to induce satiety and to reduce food intake. A secondary objective of the study is to determine the effect of (−)-(3R,5R)-trans-3-butyl-3-ethyl-2,3,4,5-tetrahydro-7,8-dimethoxy-5-phenyl-1,4-benzothiazepine1,1-dioxide on food consumption (amount and composition) during a free meal (dinner); wellness after one week supplementation; the intermeal interval; and body weight and waist-hip ratio (WHR).

Study Design: This is an 8 week study. A cohort of 500 patients is divided into placebo group and drug treated groups. 50 mg of (−)-(3R,5R)-trans-3-butyl-3-ethyl-2,3,4,5-tetrahydro-7,8-dimethoxy-5-phenyl-1,4-benzothiazepine1,1-dioxide will be administered 30 minutes prior to ingestion of lunch and prior to ingestion of dinner for a total of 100 mg of (−)-(3R,5R)-trans-3-butyl-3-ethyl-2,3,4,5-tetrahydro-7,8-dimethoxy-5-phenyl-1,4-benzothiazepine 1,1-dioxide per day.

Inclusion Critera are: a BMI >27, 70 years of age or less, waist circumference >102 cm for men or >88 cm for women, eating disorders, diabetes Exclusion criteria are: Stroke/MI/unstable cardiovascular disease within 6 months, clinically significant renal, hepatic or psychiatric disease, participation in a formal weight loss program or lifestyle intervention, glaucoma or intraocular pressure, use of any antidiabetic medication.

Blood Sampling Serial blood is drawn by direct vein puncture before and after administration of Compound 100 analog. Venous blood samples (5 mL) for determination of serum concentrations are obtained at about 10 minutes prior to dosing and at approximately the following times after dosing: days 1, 2, 3, 4, 5, 6, 7, and 14. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, and 14. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment.

Patient Response to (−)-(3R,5R)-trans-3-butyl-3-ethyl-2,3,4,5-tetrahydro-7,8-dimethoxy-5-phenyl-1,4-benzothiazepine1,1-dioxide Therapy: Patient response is assessed via weekly hospital visits, weight and waist measurements and routine blood tests.

Primary Outcome Measures: Satiety scores (visual analog scores), wellness after one week supplementation.

Secondary Outcome Measures: Demonstrate an improvement over placebo in absolute weight loss and waist to hip ratio. Demonstrate an improvement in quality of life.

Example 12: A Human Clinical Trial Similar to the Trial in Example 11 is Conducted to Determine the Effect of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Compound 100B) on Satiety and Reduction in Food Intake, Plasma Glucose and Insulin Level Example 13: Human Phase I Clinical Trial of (−)-(3R,5R)-trans-3-butyl-3-ethyl-2,3,4,5-tetrahydro-7,8-dimethoxy-5-phenyl-1,4-benzothiazepine 1,1-dioxide Alone or in Combination with Sitagliptin on Satiety and Reduction in Food Intake, Plasma Glucose and Insulin Levels Aim of the Study: A phase I dose-escalation study
Patient Population: Obese type II diabetic
Study Design: Randomized, double-blind, cross-over, single-dose placebo controlled Ten subjects will be administered a single dose of sitagliptin ten minutes before administration of a single dose of (−)-(3R,5R)-trans-3-butyl-3-ethyl-2,3,4,5-tetrahydro-7,8-dimethoxy-5-phenyl-1,4-benzothiazepine1,1-dioxide prior to ingestion of food. A second group of ten subjects will be administered a single dose of (−)-(3R,5R)-trans-3-butyl-3-ethyl-2,3,4,5-tetrahydro-7,8-dimethoxy-5-phenyl-1,4-benzothiazepine1,1-dioxide 30 minutes prior to ingestion of food. Rising dose levels of the ASBTI (1, 3, 10 and 30 mg/kg) will be administered at each visit. Each visit to test facility will be at least 72 hours apart.

A buffet style breakfast will be presented and ad-libitum food intake will be measured. Patients will record meal-related satiation, or hunger, and nausea on a chart. Satiogenic gut peptides will be measured post-prandially from plasma analytes. Insulin, glucose, GLP-1 and PYY levels in blood/plasma will be monitored for 24 hours. Subjects will be asked to record food intake for 72 hours after each dose.

Endpoints: Safety and tolerability, pharmacodynamics, food intake 24 hours after dosing.

Example 14: A Human Phase II Clinical Trial of (−)-(3R,5R)-trans-3-butyl-3-ethyl-2,3,4,5-tetrahydro-7,8-dimethoxy-5-phenyl-1,4-benzothiazepine 1,1-dioxide (Compound 100A) Alone or in Combination with Sitagliptin and Effect on Obesity or Diabetes Phase 2A: This will be a 16 week double-blind, parallel-group study. A single dose of sitagliptin in combination with (−)-(3R,5R)-trans-3-butyl-3-ethyl-2,3,4,5-tetrahydro-7,8-dimethoxy-5-phenyl-1,4-benzothiazepine1,1-dioxide will be administered as described above. A second group of subjects will be administered a single dose of (−)-(3R,5R)-trans-3-butyl-3-ethyl-2,3,4,5-tetrahydro-7,8-dimethoxy-5-phenyl-1,4-benzothiazepine1,1-dioxide 30 minutes prior to ingestion of food. A buffet style breakfast will be presented as described above and satiety and food intake will be measured.

Phase 2A: This will be a 6-week, single-blind, parallel-group study carried out as described above. Glucose levels in blood/plasma, body composition and a comprehensive assessment of food intake will be carried for the duration of the study.

Phase 2B: This will be a 16-week, double-blind, parallel group study dose-ranging study carried out as described above. Safety, dose-tolerance, glucose levels in blood/plasma, weight loss and HBA1c will be monitored for the duration of the study.

Example 15: A Human Phase II Clinical Trial Similar to the Trial in Example 14 is Conducted to Determine the Effect of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]Octane Methane sulfonate (Compound 100B) Alone or in Combination with Sitagliptin and Effect on Obesity or Diabetes

Example 16: A Human Phase II Clinical Trial Similar to the Trial in Example 14 is Conducted to Determine the Effect of Compound 4 Alone or in Combination with Sitagliptin and Effect on Obesity or Diabetes

Example 17: Human Phase I Clinical Trial of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Compound 100B) in combination with sitagliptin on satiety and reduction in food intake, plasma glucose and insulin level Aim of the Study: A phase I dose-escalation study Patient Population: Obese type II diabetic Study Design: Randomized, double-blind, cross-over, single-dose placebo controlled Ten subjects will be administered a single dose of sitagliptin ten minutes before administration of a single dose of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate prior to ingestion of food. A second group of ten subjects will be administered a single dose of 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate 30 minutes prior to ingestion of food. Rising dose levels of the ASBTI (1, 3, 10 and 30 mg/kg) will be administered at each visit. Each visit to test facility will be at least 72 hours apart.

A buffet style breakfast will be presented and ad-libitum food intake will be measured. Patients will record meal-related satiation, or hunger, and nausea on a chart. Satiogenic gut peptides will be measured post-prandially from plasma analytes. Insulin, glucose, GLP-1 and PYY levels in blood/plasma will be monitored for 24 hours. Subjects will be asked to record food intake for 72 hours after each dose.

Endpoints: Safety and tolerability, pharmacodynamics, food intake 24 hours after dosing.

Example 18: A Human Phase I Clinical Trial Similar to the Trial in Example 17 is Conducted to Determine the Effect of Compound 2 in Combination with Sitagliptin on Satiety and Reduction in Food Intake, Plasma Glucose and Insulin Level

Example 19: Human Clinical Trial of the Effect of Compound 4 on Satiety and Reduction in Food Intake Objective: The aim of the 8 week study is to show evidence of the efficacy of compound 4 to induce satiety and to reduce food intake. A secondary objective of the study is to determine the effect of compound 4 on food consumption (amount and composition) during a free meal (dinner); wellness after one week supplementation; the intermeal interval; and body weight and waist-hip ratio (WHR).

Study Design: This is an 8 week study. A cohort of 500 patients is divided into placebo group and drug treated groups. 50 mg of compound 4 will be administered 30 minutes prior to ingestion of lunch and prior to ingestion of dinner for a total of 100 mg of compound 4 per day.

Inclusion Critera are: a BMI >27, 70 years of age or less, waist circumference >102 cm for men or >88 cm for women.

Exclusion criteria are: Stroke/MI/unstable cardiovascular disease within 6 months, clinically significant renal, hepatic or psychiatric disease, participation in a formal weight loss program or lifestyle intervention, glaucoma or intraocular pressure, use of any antidiabetic medication, previous bariatric surgery Blood Sampling Serial blood is drawn by direct vein puncture before and after administration of Compound 100 analog. Venous blood samples (5 mL) for determination of serum concentrations are obtained at about 10 minutes prior to dosing and at approximately the following times after dosing: days 1, 2, 3, 4, 5, 6, 7, and 14. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, and 14. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment.

Patient Response to Compound 4 Therapy: Patient response is assessed via weekly hospital visits, weight and waist measurements and routine blood tests.

Primary Outcome Measures: Satiety scores (visual analog scores), wellness after one week supplementation.

Secondary Outcome Measures: Demonstrate an improvement over placebo in absolute weight loss and waist to hip ratio. Demonstrate an improvement in quality of life.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating diabetes comprising administering to the distal ileum, the colon, or the rectum of a diabetic individual, a single pharmaceutical composition consisting of a therapeutically effective amount of an Apical Sodium-dependent Bile Transporter Inhibitor (ASBTI) and one or more pharmaceutical carriers, wherein the ASBTI is

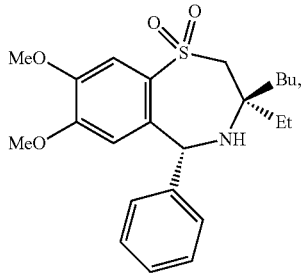

or a pharmaceutically acceptable salt thereof.

2. A method of treating diabetes comprising administering to the distal ileum, the colon, or the rectum of a diabetic individual, a single pharmaceutical composition consisting of a therapeutically effective amount of an Apical Sodium-dependent Bile Transporter Inhibitor (ASBTI) and one or more pharmaceutical carriers, wherein the ASBTI is

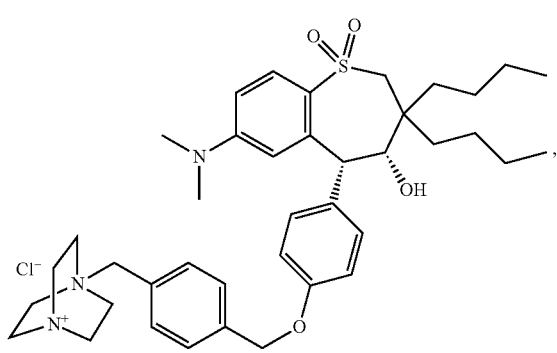

or a pharmaceutically acceptable salt thereof.

3. A method of treating diabetes comprising administering to the distal ileum, the colon, or the rectum of a diabetic individual, a single pharmaceutical composition consisting of a therapeutically effective amount of an Apical Sodium-dependent Bile Transporter Inhibitor (ASBTI) and one or more pharmaceutical carriers, wherein the ASBTI is

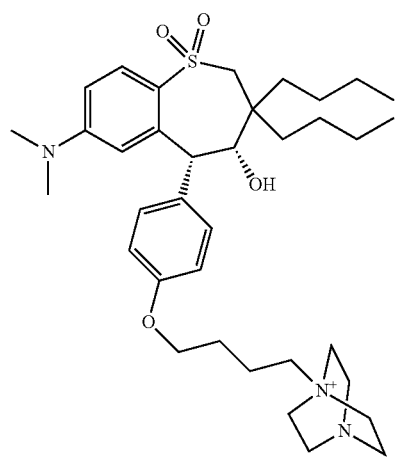 [SMILES: CCCCC1(CCCC)CS(=O)(=O)c2ccc(N(C)C)cc2[C@@H](c2ccc(OCCCC[N+]34CCN(CC3)CC4)cc2)[C@H]1O]

or a pharmaceutically acceptable salt thereof.

4. A method of treating diabetes comprising administering to the distal ileum, the colon, or the rectum of a diabetic individual, a single pharmaceutical composition consisting of a therapeutically effective amount of an Apical Sodium-dependent Bile Transporter Inhibitor (ASBTI) and one or more pharmaceutical carriers, wherein the ASBTI is

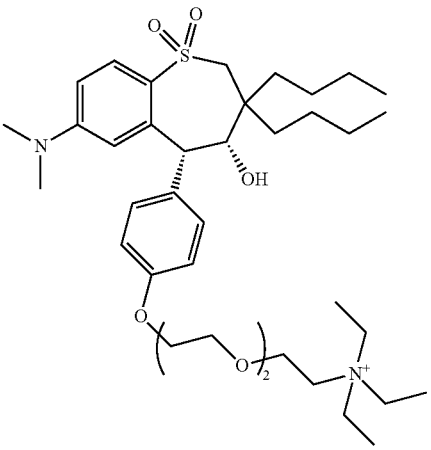

or a pharmaceutically acceptable salt thereof.

5. A method of treating diabetes comprising administering to the distal ileum, the colon, or the rectum of a diabetic individual, a single pharmaceutical composition consisting of a therapeutically effective amount of an Apical Sodium-dependent Bile Transporter Inhibitor (ASBTI) and one or more pharmaceutical carriers, wherein the ASBTI is

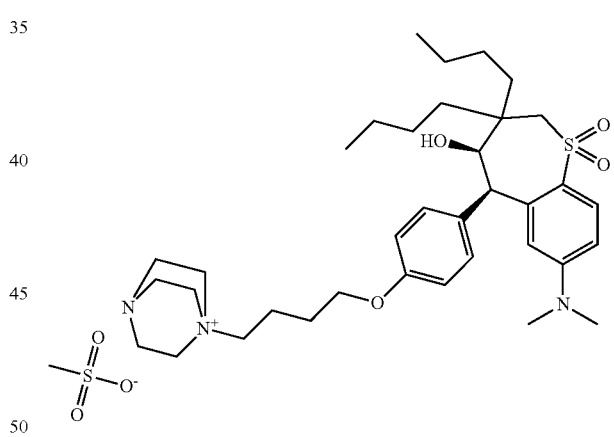

or a pharmaceutically acceptable salt thereof.

6. A method of treating diabetes comprising administering to the distal ileum, the colon, or the rectum of a diabetic individual, a single pharmaceutical composition consisting of a therapeutically effective amount of an Apical Sodium-dependent Bile Transporter Inhibitor (ASBTI) and one or more pharmaceutical carriers, wherein the ASBTI is selected from the group consisting of:
  1,1-dioxo-3,3-dibutyl-5-phenyl-7-methylthio-8-(N-{(R)-α-[N((R)-1-carboxy-2-methylthio-ethyl)carbamoyl]-4-hydroxybenzyl}carbamoylmethoxy)-2,3,4,5-tetrahydro-1,2,5-benzothiadiazepine;
  1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-[N-{(R)-α-carboxy-4-hydroxybenzyl}carbamoylmethoxy]-2,3,4,5-tetrahydro-1,2,5-benzothiadiazepine;

1,1-dioxo-3,3-dibutyl-5-phenyl-7-methylthio-8-(N-{(R)-α-[N-(carboxymethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(carboxymethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxyethyl)carbamoyl]benzyl}carbamoylmethoxy)-2,3,4,5-tetrahydro-1,5-benzothiazepine; and 1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

or a pharmaceutically acceptable salt thereof.

* * * * *